(12) United States Patent
Figueiredo et al.

(10) Patent No.: US 10,080,723 B2
(45) Date of Patent: Sep. 25, 2018

(54) THERAPEUTIC NANOPARTICLES COMPRISING A THERAPEUTIC AGENT AND METHODS OF MAKING AND USING SAME

(71) Applicant: Pfizer Inc., New York, NY (US)

(72) Inventors: Maria Figueiredo, Somerville, MA (US); Erick Peeke, Somerville, MA (US); David Dewitt, Allston, MA (US); Christina Van Geen Hoven, Cambridge, MA (US); Greg Troiano, Pembroke, MA (US); James Wright, Lexington, MA (US); Young-ho Song, Natick, MA (US); Hong Wang, Newton, MA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 15/118,737

(22) PCT Filed: Feb. 13, 2015

(86) PCT No.: PCT/US2015/015887
§ 371 (c)(1),
(2) Date: Aug. 12, 2016

(87) PCT Pub. No.: WO2015/123562
PCT Pub. Date: Aug. 20, 2015

(65) Prior Publication Data
US 2017/0042828 A1   Feb. 16, 2017

Related U.S. Application Data

(60) Provisional application No. 61/939,363, filed on Feb. 13, 2014.

(51) Int. Cl.
*B82Y 5/00* (2011.01)
*A61K 9/51* (2006.01)
(Continued)

(52) U.S. Cl.
CPC .......... *A61K 9/5192* (2013.01); *A61K 9/0019* (2013.01); *A61K 9/5123* (2013.01);
(Continued)

(58) Field of Classification Search
CPC ....... B82Y 5/00; A61K 9/5153; A61K 9/5146
See application file for complete search history.

(56) References Cited

U.S. PATENT DOCUMENTS

| | | |
|---|---|---|
| 9,877,923 B2 | 1/2018 | Figueiredo et al. |
| 9,895,378 B2 | 2/2018 | Bagrodia et al. |
| 2014/0178475 A1 | 6/2014 | Figueiredo et al. |

FOREIGN PATENT DOCUMENTS

| | | | |
|---|---|---|---|
| WO | 2005/009357 | | 2/2005 |
| WO | 2005009357 | * | 2/2005 |

(Continued)

OTHER PUBLICATIONS

Kimura et al, "Local Delivery of 1,2, Imatinib Mesylate (STI571)-Incorporated 4-26, Nanoparticle Ex Vivo Suppresses Vein Graft 28-87 Neointima Formation"; Circulation, vol. 118(14), suppl 1, Sep. 30, 2008 (Sep. 30, 2008), pp. 1-25XP055088937, US ISSN: 0009-7322, DOI: 10.1161/CIRCULATIONAHA.107.740613 abstract p. s65, left-hand column, line 1-line 23.

(Continued)

*Primary Examiner* — Carlos A Azpuru
(74) *Attorney, Agent, or Firm* — Feng Shao

(57) ABSTRACT

The present disclosure generally relates to nanoparticles comprising a substantially hydrophobic acid, a basic therapeutic agent having a protonatable nitrogen, and a polymer. Other aspects include methods of making and using such nanoparticles.

14 Claims, 10 Drawing Sheets

(51) Int. Cl.
*A61K 9/00* (2006.01)
*A61K 31/404* (2006.01)
*A61K 31/506* (2006.01)

(52) U.S. Cl.
CPC .......... *A61K 9/5146* (2013.01); *A61K 9/5153* (2013.01); *A61K 31/404* (2013.01); *A61K 31/506* (2013.01); *B82Y 5/00* (2013.01)

(56) References Cited

FOREIGN PATENT DOCUMENTS

| WO | 2010/005721 | | 1/2010 |
| WO | 2010005721 A1 | * | 1/2010 |
| WO | 2014/043625 | | 3/2014 |
| WO | 2015/036792 | | 3/2015 |

OTHER PUBLICATIONS

Li J et al: "Post-operative imatinib in patients with intermediate or high risk gastrointestinal stromal tumor", European Journal of Surgical Oncology, London, GB, vol. 37(4), Jan. 4, 2011 (Jan. 4, 2011), pp. 319-324.

* cited by examiner

THERAPEUTIC NANOPARTICLES COMPRISING A THERAPEUTIC AGENT AND METHODS OF MAKING AND USING SAME

CROSS-REFERENCE TO RELATED APPLICATION

This application is a national stage application of PCT/US2015/015887, filed Feb. 13 27, 2015, pursuant to 35 U.S.C. § 371, and claims the benefit of and priority to U.S. Provisional Patent Application No. 61/939,363, filed Feb. 13, 2014, which is hereby incorporated by reference in its entirety.

BACKGROUND

Systems that deliver certain drugs to a patient (e.g., targeted to a particular tissue or cell type or targeted to a specific diseased tissue but not normal tissue) or that control release of drugs have long been recognized as beneficial.

For example, therapeutics that include an active drug and that are, e.g., targeted to a particular tissue or cell type or targeted to a specific diseased tissue but not to normal tissue, may reduce the amount of the drug in tissues of the body that are not targeted. This is particularly important when treating a condition such as cancer where it is desirable that a cytotoxic dose of the drug is delivered to cancer cells without killing the surrounding non-cancerous tissue. Effective drug targeting may reduce the undesirable and sometimes life threatening side effects common in anticancer therapy. In addition, such therapeutics may allow drugs to reach certain tissues they would otherwise be unable to reach.

Therapeutics that offer controlled release and/or targeted therapy also must be able to deliver an effective amount of drug, which is a known limitation in other nanoparticle delivery systems. For example, it can be a challenge to prepare nanoparticle systems that have an appropriate amount of drug associated with each nanoparticle, while keeping the size of the nanoparticles small enough to have advantageous delivery properties.

Therapeutic agents containing at least one basic nitrogen atom (i.e., protonatable nitrogen-containing therapeutic agents) represent an important group of therapeutic agents. However, nanoparticle formulations of this class of drugs are often hindered by undesirable properties, e.g., burst release profiles and poor drug loading.

Accordingly, a need exists for nanoparticle therapeutics and methods of making such nanoparticles that are capable of delivering therapeutic levels of protonatable nitrogen-containing therapeutic agents to treat diseases such as cancer, while also reducing patient side effects.

SUMMARY

Described herein are polymeric nanoparticles that include a protonatable nitrogen-containing therapeutic agent, and methods of making and using such therapeutic nanoparticles.

In one aspect, a process for preparing a therapeutic nanoparticle is provided. The process comprises combining a first organic phase with a first aqueous solution to form a second phase; emulsifying the second phase to form an emulsion phase, wherein the emulsion phase comprises a first polymer, a basic therapeutic agent having a protonatable nitrogen, and pamoic acid; quenching of the emulsion phase thereby forming a quenched phase.

In some embodiments, quenching of the emulsion phase comprises mixing the emulsion phase with a second aqueous solution having a pH between about 2 and about 8.

In another aspect, a process for preparing a therapeutic nanoparticle is provided. The process comprises combining a first organic phase with a first aqueous solution to form a second phase; emulsifying the second phase to form an emulsion phase, wherein the emulsion phase comprises a first polymer, a basic therapeutic agent having a protonatable nitrogen, and a substantially hydrophobic acid; quenching of the emulsion phase thereby forming a quenched phase, wherein quenching of the emulsion phase comprises mixing the emulsion phase with a second aqueous solution having a pH between about 4 and about 7.

In some embodiments, the process further comprises filtering the quenched phase to recover the therapeutic nanoparticles.

In some embodiments, the process further comprises combining the basic therapeutic agent and the acid in the second phase prior to emulsifying the second phase. For example, in some embodiments, the basic therapeutic agent and the acid form a hydrophobic ion pair prior to emulsifying the second phase. In other embodiments, the basic therapeutic agent and the acid form a hydrophobic ion pair prior during emulsification of the second phase.

In some embodiments, the process further comprises combining the basic therapeutic agent and the acid in the second phase substantially concurrently with emulsifying the second phase. For example, in some embodiments, the first organic phase comprises the basic therapeutic agent and the first aqueous solution comprises the acid.

In some embodiments, the basic therapeutic agent, when protonated, has a first $pK_a$, the acid has a second $pK_a$, and the emulsion phase is quenched with an aqueous solution having a pH equal to a $pK_a$ unit between the first $pK_a$ and the second $pK_a$. For example, in some instances, the quenched phase has a pH equal to a $pK_a$ unit between the first $pK_a$ and the second $pK_a$. In some embodiments, the basic therapeutic agent, when protonated, has a first $pK_a$, the acid has a second $pK_a$, and the first aqueous solution has a pH equal to a $pK_a$ unit between the first $pK_a$ and the second $pK_a$. In some embodiments, the pH (e.g., of the quenched phase or first aqueous solution) is equal to a $pK_a$ unit that is about equidistant between the first $pK_a$ and the second $pK_a$.

In yet another aspect, a therapeutic nanoparticle is provided. The therapeutic nanoparticle is prepared by emulsification of a first organic phase comprising a first polymer, a basic therapeutic agent having a protonatable nitrogen, and pamoic acid, thereby forming an emulsion phase; and quenching of the emulsion phase thereby forming a quenched phase.

In some embodiments, quenching of the emulsion phase comprises mixing the emulsion phase with an aqueous solution having a pH between about 2 and about 8.

In still another aspect, a therapeutic nanoparticle is provided. The therapeutic nanoparticle is prepared by emulsification of a first organic phase comprising a first polymer, a basic therapeutic agent having a protonatable nitrogen, and a substantially hydrophobic acid, thereby forming an emulsion phase; and quenching of the emulsion phase thereby forming a quenched phase, wherein quenching of the emulsion phase comprises mixing the emulsion phase with an aqueous solution having a pH between about 4 and about 7.

In some embodiments, the pH of a contemplated aqueous solution (e.g., first or second aqueous solution is between about 4 and about 7, e.g., between about 4 and about 5 or between about 6 and about 7.

In some embodiments, a contemplated aqueous solution comprises phosphate, citrate, or a mixture of phosphate and citrate. In some embodiments, the second aqueous solution comprises a mixture of borate, phosphate, and acetate.

In some embodiments, a contemplated proves for preparing a therapeutic nanoparticle further comprises filtration of the quenched phase to recover the therapeutic nanoparticles.

In some embodiments, the quenched phase has a pH substantially the same as the emulsion phase. In some embodiments, the quenched phase has a pH between about 4 and about 7, e.g., between about 4 and about 5 or between about 6 and about 7.

In yet another aspect, a therapeutic nanoparticle is provided. The therapeutic nanoparticle comprises about 0.05 to about 30 weight percent of pamoic acid; about 0.2 to about 20 weight percent of a basic therapeutic agent having a protonatable nitrogen; and about 50 to about 99.75 weight percent of a diblock poly(lactic) acid-poly(ethylene)glycol copolymer or a diblock poly(lactic acid-co-glycolic acid)-poly(ethylene)glycol copolymer, wherein the therapeutic nanoparticle comprises about 10 to about 30 weight percent poly(ethylene)glycol.

In still another aspect, a therapeutic nanoparticle is provided. The therapeutic nanoparticle comprises about 0.2 to about 20 weight percent of a basic therapeutic agent having a protonatable nitrogen; pamoic acid, wherein the molar ratio of the pamoic acid to the basic therapeutic agent is about 0.25:1 to about 2:1; and about 50 to about 99.75 weight percent of a diblock poly(lactic) acid-poly(ethylene) glycol copolymer or a diblock poly(lactic acid-co-glycolic acid)-poly(ethylene)glycol copolymer, wherein the therapeutic nanoparticle comprises about 10 to about 30 weight percent poly(ethylene)glycol.

In some embodiments, the molar ratio of the pamoic acid to the basic therapeutic agent is about 0.5:1 to about 1.5:1, e.g., about 0.75:1 to about 1.25:1.

In some embodiments, the $pK_a$ of the basic therapeutic agent is at least about 1.0 $pK_a$ units greater than the $pK_a$ of the pamoic acid, or at least about 2.0 $pK_a$ units greater than the $pK_a$ of the pamoic acid, or at least about 4.0 $pK_a$ units greater than the $pK_a$ of the pamoic acid.

In yet another aspect, a therapeutic nanoparticle is provided. The therapeutic nanoparticle comprises a hydrophobic ion-pair comprising pamoic acid and a therapeutic agent having at least one ionizable amine moiety; and about 50 to about 99.75 weight percent of a diblock poly(lactic) acid-poly(ethylene)glycol copolymer, wherein the poly(lactic) acid-poly(ethylene)glycol copolymer has a number average molecular weight of about 15 kDa to about 20 kDa poly(lactic acid) and a number average molecular weight of about 4 kDa to about 6 kDa poly(ethylene)glycol.

In some embodiments, wherein the difference between the pKa of the basic therapeutic agent and the pamoic acid is at least about 1.0 pKa units, or at least about 2.0 pKa units, or at least about 4.0 pKa units.

In some embodiments, a contemplated therapeutic nanoparticle comprises about 0.05 to about 30 weight percent of the pamoic acid.

In some embodiments, the pamoic acid and the basic therapeutic agent form a hydrophobic ion pair in a contemplated therapeutic nanoparticle.

In some embodiments, a contemplated therapeutic nanoparticle comprises about 2 to about 20 weight percent, or about 4 to about 20 weight percent, or about 10 to about 20 weight percent, or about 4 to about 10 weight percent of the protonatable nitrogen-containing therapeutic agent.

In some embodiments, the therapeutic agent is a kinase inhibitor. For example, in some embodiments, the kinase inhibitor is a tyrosine kinase inhibitor selected from the group consisting of sunitinib, imatinib, nilotinib, dasatinib, bosutinib, ponatinib, bafetinib, and pharmaceutically acceptable salts thereof.

In some embodiments, the hydrodynamic diameter of a contemplated therapeutic nanoparticle is about 60 to about 150 nm, or about 90 to about 140 nm, or about 90 to about 120 nm.

In some embodiments, a contemplated therapeutic nanoparticle substantially retains the therapeutic agent for at least 1 minute when placed in a phosphate buffer solution at 37° C.

In some embodiments, a contemplated therapeutic nanoparticle substantially immediately releases less than about 30% of the therapeutic agent when placed in a phosphate buffer solution at 37° C.

In some embodiments, a contemplated therapeutic nanoparticle releases about 10 to about 45% of the therapeutic agent over about 1 hour when placed in a phosphate buffer solution at 37° C.

In some embodiments, a contemplated therapeutic nanoparticle has a release profile that is substantially the same as a release profile for a control nanoparticle that is substantially the same as the therapeutic nanoparticle except that it does not contain a fatty acid or bile acid.

In some embodiments, the poly(lactic) acid-poly(ethylene)glycol copolymer has a poly(lactic) acid number average molecular weight fraction of about 0.6 to about 0.95, or about 0.6 to about 0.8, or about 0.75 to about 0.85, or about 0.7 to about 0.9.

In some embodiments, a contemplated therapeutic nanoparticle comprises about 10 to about 25 weight percent poly(ethylene)glycol, or about 10 to about 20 weight percent poly(ethylene)glycol, or about 15 to about 25 weight percent poly(ethylene)glycol, or about 20 to about 30 weight percent poly(ethylene)glycol.

In some embodiments, the poly(lactic) acid-poly(ethylene)glycol copolymer has a number average molecular weight of about 15 kDa to about 20 kDa poly(lactic acid) and a number average molecular weight of about 4 kDa to about 6 kDa poly(ethylene)glycol.

In some embodiments, a contemplated therapeutic nanoparticle further comprises about 0.2 to about 30 weight percent poly(lactic) acid-poly(ethylene)glycol copolymer functionalized with a targeting ligand. In some embodiments, a contemplated therapeutic nanoparticle further comprises about 0.2 to about 30 weight percent poly(lactic) acid-co-poly(glycolic) acid-poly(ethylene)glycol copolymer functionalized with a targeting ligand. For example, in some embodiments, the targeting ligand is covalently bound to the poly(ethylene)glycol.

In some embodiments, a contemplated therapeutic nanoparticle comprises a mixture of pamoic acid and a substantially hydrophobic acid.

In yet another aspect, a pharmaceutically acceptable composition is provided. The composition comprises a plurality of contemplated therapeutic nanoparticles and a pharmaceutically acceptable excipient.

In some embodiments, a contemplated pharmaceutically acceptable composition further comprises a saccharide, e.g., sucrose, trehalose, or a mixture thereof.

In some embodiments, a contemplated pharmaceutically acceptable composition further comprises a cyclodextrin, e.g., α-cyclodextrin, β-cyclodextrin, γ-cyclodextrin, heptakis-(2,3,6-tri-O-benzyl)-β-cyclodextrin, and mixtures thereof.

In still another aspect, a method of treating cancer in a patient in need thereof is provided. The method comprises administering to the patient a therapeutically effective amount of a composition comprising a contemplated therapeutic nanoparticle.

In some embodiments, the cancer is chronic myelogenous leukemia. In some embodiments, the cancer is selected from the group consisting of chronic myelomonocytic leukemia, hypereosinophilic syndrome, renal cell carcinoma, hepatocellular carcinoma, Philadelphia chromosome positive acute lymphoblastic leukemia, non-small cell lung cancer, pancreatic cancer, breast cancer, a solid tumor, and mantle cell lymphoma.

In yet another aspect, a method of treating a gastrointestinal stromal tumor in a patient in need thereof is provided. The method comprises administering to the patient a therapeutically effective amount of a composition comprising a contemplated therapeutic nanoparticle.

DETAILED DESCRIPTION

Figure 1:
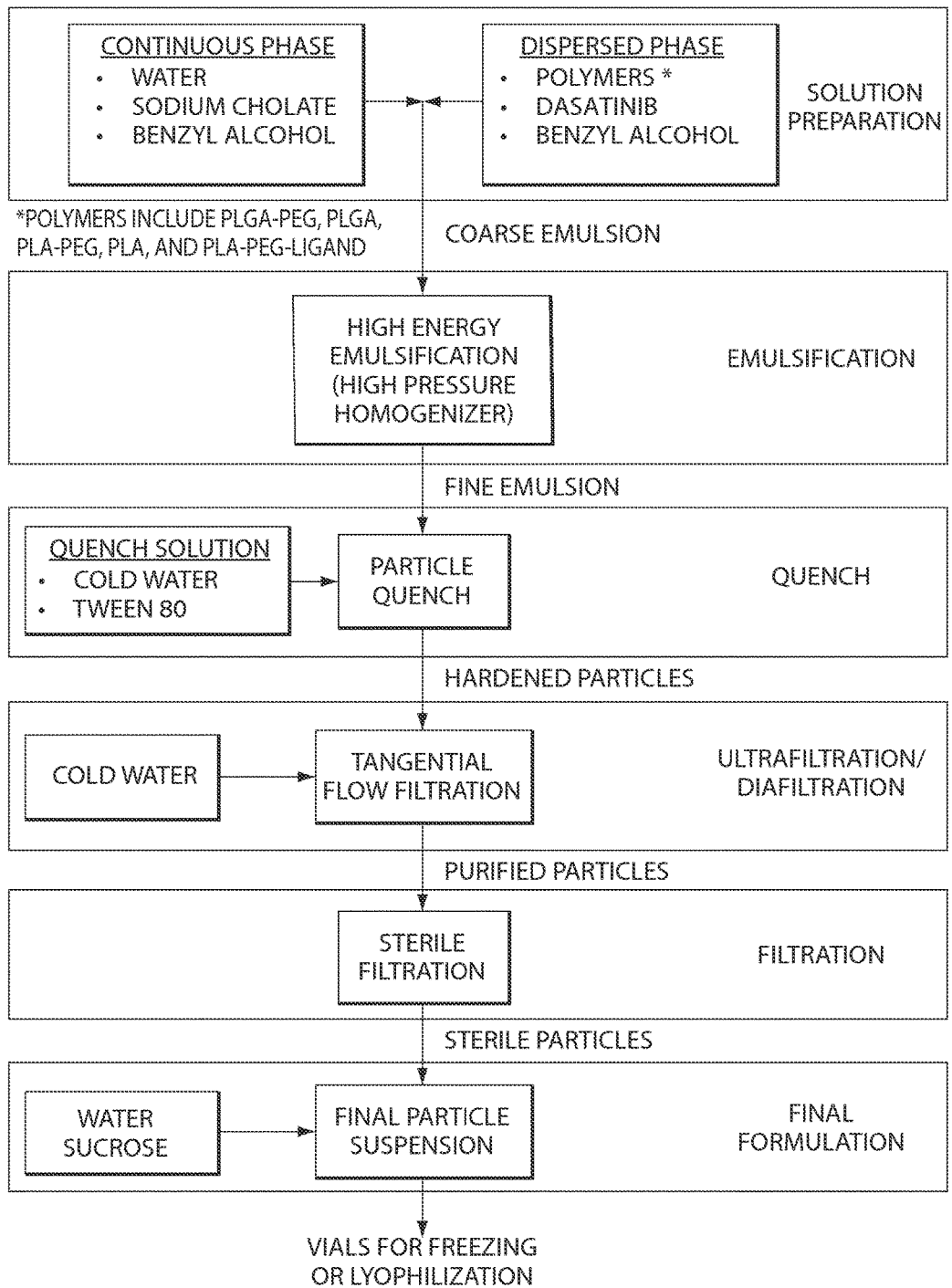
FIG. 1 is flow chart for an emulsion process for forming a disclosed nanoparticle.

Described herein are polymeric nanoparticles that include a basic therapeutic agent having a protonatable nitrogen (e.g., a protonatable nitrogen-containing therapeutic agent), and methods of making and using such therapeutic nanoparticles. In some embodiments, inclusion (i.e., doping) of a substantially hydrophobic acid (e.g., pamoic acid) in a disclosed nanoparticle and/or included in a nanoparticle preparation process may result in nanoparticles that include improved drug loading. Furthermore, in certain embodiments, nanoparticles that include and/or are prepared in the presence of the hydrophobic acid may exhibit improved controlled release properties. For example, disclosed nanoparticles may more slowly release the protonatable nitrogen-containing therapeutic agent as compared to nanoparticles prepared in the absence of the hydrophobic acid.

Without wishing to be bound by any theory, it is believed that the disclosed nanoparticle formulations that include a hydrophobic acid (e.g., fatty acid and/or bile acid) have significantly improved formulation properties (e.g., drug loading and/or release profile) through formation of a hydrophobic ion-pair (HIP), between a therapeutic agent having, e.g., amines and an acid. As used herein, a HIP is a pair of oppositely charged ions held together by Coulombic attraction. Also without wishing to be bound by any theory, in some embodiments, HIP can be used to increase the hydrophobicity of a therapeutic agent containing ionizable groups (e.g., amines). In some embodiments, a therapeutic agent with increased hydrophobicity can be beneficial for nanoparticle formulations and result in a HIP formation that may provide higher solubility of the therapeutic agent in organic solvents. HIP formation, as contemplated herein, can result in nanoparticles having for example, increased drug loading. Slower release of the therapeutic agent from the nanoparticles may also occur, for example in some embodiments, due to a decrease in the therapeutic agent's solubility in aqueous solution. Furthermore, complexing the therapeutic agent with large hydrophobic counter ions may slow diffusion of the therapeutic agent within the polymeric matrix. Advantageously, HIP formation occurs without the need for covalent conjugation of the hydrophobic group to the therapeutic agent.

Without wishing to be bound by any theory, it is believed that the strength of the HIP impacts the drug load and release rate of the contemplated nanoparticles. For example, the strength of the HIP may be increased by increasing the magnitude of the difference between the $pK_a$ of the protonatable nitrogen-containing therapeutic agent and the $pK_a$ of the hydrophobic acid, as discussed in more detail below. Also without wishing to be bound by any theory, it is believed that the conditions for ion pair formation impact the drug load and release rate of the contemplated nanoparticles.

Nanoparticles disclosed herein include one, two, three or more biocompatible and/or biodegradable polymers. For example, a contemplated nanoparticle may include about 35 to about 99.75 weight percent, in some embodiments about 50 to about 99.75 weight percent, in some embodiments about 50 to about 99.5 weight percent, in some embodiments about 50 to about 99 weight percent, in some embodiments about 50 to about 98 weight percent, in some embodiments about 50 to about 97 weight percent, in some embodiments about 50 to about 96 weight percent, in some embodiments about 50 to about 95 weight percent, in some embodiments about 50 to about 94 weight percent, in some embodiments about 50 to about 93 weight percent, in some embodiments about 50 to about 92 weight percent, in some embodiments about 50 to about 91 weight percent, in some embodiments about 50 to about 90 weight percent, in some embodiments about 50 to about 85 weight percent, in some embodiments about 60 to about 85 weight percent, in some embodiments about 65 to about 85 weight percent, and in some embodiments about 50 to about 80 weight percent of one or more block copolymers that include a biodegradable polymer and poly(ethylene glycol) (PEG), and about 0 to about 50 weight percent of a biodegradable homopolymer.

The disclosed nanoparticles may include a protonatable nitrogen-containing therapeutic agent. As used herein, a "protonatable nitrogen-containing therapeutic agent" includes any pharmaceutically active agent that contains at least one protonatable nitrogen-containing functional group. The protonatable nitrogen-containing therapeutic agent may contain one, two, three, or more protonatable nitrogen-containing functional groups. Non-limiting examples of protonatable nitrogen-containing functional groups include aliphatic amino groups (e.g., primary amines, secondary amines, and tertiary amines), nitrogen-containing heteroaryl groups (e.g., pyridine, imidazole, triazole, and tetrazole), and guanidino groups.

In some embodiments, disclosed nanoparticles may include about 0.2 to about 35 weight percent, about 0.2 to about 20 weight percent, about 0.2 to about 10 weight percent, about 0.2 to about 5 weight percent, about 0.5 to about 5 weight percent, about 0.75 to about 5 weight percent, about 1 to about 5 weight percent, about 2 to about 5 weight percent, about 3 to about 5 weight percent, about 1 to about 20 weight percent, about 2 to about 20 weight percent, about 4 to about 20 weight percent, about 5 to about 20 weight percent, about 10 to about 20 weight percent, about 1 to about 15 weight percent, about 2 to about 15 weight percent, about 3 to about 15 weight percent, about 4 to about 15 weight percent, about 5 to about 15 weight percent, about 1 to about 10 weight percent, about 2 to about 10 weight percent, about 3 to about 10 weight percent, about 4 to about 10 weight percent, about 5 to about 10 weight percent, about 10 to about 30 weight percent, or about 15 to about 25 weight percent of a protonatable nitrogen-containing therapeutic agent.

In certain embodiments, disclosed nanoparticles comprise a hydrophobic acid (e.g., a fatty acid and/or bile acid) and/or are prepared by a process that includes a hydrophobic acid. Such nanoparticles may have a higher drug loading than nanoparticles prepared by a process without a hydrophobic acid. For example, drug loading (e.g., by weight) of disclosed nanoparticles prepared by a process comprising the hydrophobic acid may be between about 2 times to about 10 times higher, or even more, than disclosed nanoparticles prepared by a process without the hydrophobic acid. In some embodiments, the drug loading (by weight) of disclosed nanoparticles prepared by a first process comprising the hydrophobic acid may be at least about 2 times higher, at least about 3 times higher, at least about 4 times higher, at least about 5 times higher, or at least about 10 times higher than disclosed nanoparticles prepared by a second process, where the second process is identical to the first process except that the second process does not include the hydrophobic acid.

Any suitable hydrophobic acid is contemplated. In some embodiments, the hydrophobic acid may be a carboxylic acid (e.g., a monocarboxylic acid, dicarboxylic acid, tricarboxylic acid, or the like), a sulfinic acid, a sulfenic acid, or a sulfonic acid. In some cases, a contemplated hydrophobic acid may include a mixture of two or more acids. For example, in certain embodiments, the hydrophobic acid may comprise a mixture of two substantially hydrophobic acids, in some embodiments a mixture of three substantially hydrophobic acids, in some embodiments a mixture of four substantially hydrophobic acids, or in some embodiments five substantially hydrophobic acids.

In some cases, a salt of a hydrophobic acid may be used in a formulation.

For example, a disclosed carboxylic acid may be an aliphatic carboxylic acid (e.g., a carboxylic acid having a cyclic or acyclic, branched or unbranched, hydrocarbon chain). Disclosed carboxylic acids may, in some embodiments, be substituted with one or more functional groups including, but not limited to, halogen (i.e., F, Cl, Br, and I), sulfonyl, nitro, and oxo. In certain embodiments, a disclosed carboxylic acid may be unsubstituted.

Exemplary carboxylic acids may include a substituted or unsubstituted fatty acid (e.g., $C_6$-$C_{50}$ fatty acid). In some instances, the fatty acid may be a $C_{10}$-$C_{20}$ fatty acid. In other instances, the fatty acid may be a $C_{15}$-$C_{20}$ fatty acid. The fatty acid may, in some cases, be saturated. In other embodiments, the fatty acid may be unsaturated. For instance, the fatty acid may be a monounsaturated fatty acid or a polyunsaturated fatty acid. In some embodiments, a double bond of an unsaturated fatty acid group can be in the cis conformation. In some embodiments, a double bond of an unsaturated fatty acid can be in the trans conformation. Unsaturated fatty acids include, but are not limited to, omega-3, omega-6, and omega-9 fatty acids.

Non-limiting examples of saturated fatty acids include caproic acid, enanthic acid, caprylic acid, pelargonic acid, capric acid, undecanoic acid, lauric acid, tridecanoic acid, myristic acid, pentadecanoic acid, palmitic acid, margaric acid, stearic acid, nonadecanoic acid, arachidic acid, heneicosanoic acid, behenic acid, tricosanoic acid, lignoceric acid, pentacosanoic acid, cerotic acid, heptacosanoic acid, montanic acid, nonacosanoic acid, melissic acid, henatriacontanoic acid, lacceroic acid, psyllic acid, geddic acid, ceroplastic acid, hexatriacontanoic acid, and combinations thereof.

Non-limiting examples of unsaturated fatty acids include hexadecatrienoic acid, alpha-linolenic acid, stearidonic acid, eicosatrienoic acid, eicosatetraenoic acid, eicosapentaenoic acid, heneicosapentaenoic acid, docosapentaenoic acid, docosahexaenoic acid, tetracosapentaenoic acid, tetracosahexaenoic acid, linoleic acid, gamma-linolenic acid, eicosadienoic acid, dihomo-gamma-linolenic acid, arachidonic acid, docosadienoic acid, adrenic acid, docosapentaenoic acid, tetracosatetraenoic acid, tetracosapentaenoic acid, oleic acid ($pK_a$=~4-5; log P=6.78), eicosenoic acid, mead acid, erucic acid, nervonic acid, rumenic acid, α-calendic acid, β-calendic acid, jacaric acid, α-eleostearic acid, β-eleostearic acid, catalpic acid, punicic acid, rumelenic acid, α-parinaric acid, β-parinaric acid, bosseopentaenoic acid, pinolenic acid, podocarpic acid, palmitoleic acid, vaccenic acid, gadoleic acid, erucic acid, and combinations thereof.

Other non-limiting examples of hydrophobic acids include aromatic acids, such as 1-hydroxy-2-naphthoic acid (i.e., xinafoic acid) ($pK_a$=~2-3; log P=2.97), naphthalene-1,5-disulfonic acid ($pK_a$=~2; log P=1.3), naphthalene-2-sulfonic acid ($pK_a$=~1.8; log P=2.1), pamoic acid ($pK_a$=2.4), cinnamic acid, phenylacetic acid, (±)-camphor-10-sulfonic acid, dodecylbenzenesulfonic acid ($pK_a$=~1.8; log P=6.6), and combinations thereof. Other non-limiting examples of hydrophobic acids include dodecylsulfuric acid ($pK_a$=~0.09; log P=4.5), dioctyl sulfosuccinic acid (i.e., docusate acid) ($pK_a$=~0.8; log P=5.2), dioleoyl phosphatidic acid ($pK_a$=~2), and Vitamin $D_3$-sulfate ($pK_a$=~1.5).

In some embodiments, the hydrophobic acid may be a bile acid. Non-limiting examples of bile acids include chenodeoxycholic acid, ursodeoxycholic acid, deoxycholic acid ($pK_a$=4.65; log P=3.79), hycholic acid, beta-muricholic acid, cholic acid ($pK_a$=~4.5; log P=2.48), taurocholic acid, cholesteryl sulfate ($pK_a$=~1.4), lithocholic acid, an amino acid-conjugated bile acid, and combinations thereof. An amino-acid conjugated bile acid may be conjugated to any suitable amino acid. In some embodiments, the amino acid-conjugated bile acid is a glycine-conjugated bile acid or a taurine-conjugated bile acid.

In certain instances, the hydrophobic acid may be a polyelectrolyte. For example, the polyelectrolyte may be a polysulfonic acid (e.g., poly(styrene sulfonic acid) or dextran sulfate) or a polycarboxylic acid (e.g., polyacrylic acid or polymethacrylic acid).

In some instances, a contemplated acid may have a molecular weight of less than about 1000 Da, in some embodiments less than about 500 Da, in some embodiments less than about 400 Da, in some embodiments less than about 300 Da, in some embodiments less than about 250 Da, in some embodiments less than about 200 Da, and in some embodiments less than about 150 Da. In some cases, the acid may have a molecular weight of between about 100 Da and about 1000 Da, in some embodiments between about 200 Da and about 800 Da, in some embodiments between about 200 Da and about 600 Da, in some embodiments between about 100 Da and about 300 Da, in some embodiments between about 200 Da and about 400 Da, in some embodiments between about 300 Da and about 500 Da, and in some embodiments between about 300 Da and about 1000 Da. In certain embodiments, a contemplated acid may have a molecular weight of greater than about 300 Da, in some embodiments greater than 400 Da, and in some embodiments greater than 500 Da. In certain embodiments, the release rate of a therapeutic agent from a nanoparticle can be slowed by increasing the molecular weight of the hydrophobic acid used in the nanoparticle formulation.

In some embodiments, a hydrophobic acid may be chosen, at least in part, on the basis of the strength of the acid. For example, the hydrophobic acid may have an acid dissociation constant in water ($pK_a$) of about −5 to about 7, in some embodiments about −3 to about 5, in some embodiments about −3 to about 4, in some embodiments about −3 to about 3.5, in some embodiments about −3 to about 3, in some embodiments about −3 to about 2, in some embodiments about −3 to about 1, in some embodiments about −3 to about 0.5, in some embodiments about −0.5 to about 0.5, in some embodiments about 1 to about 7, in some embodiments about 2 to about 7, in some embodiments about 3 to about 7, in some embodiments about 4 to about 6, in some embodiments about 4 to about 5.5, in some embodiments about 4 to about 5, and in some embodiments about 4.5 to about 5, determined at 25° C. In some embodiments, the acid may have a $pK_a$ of less than about 7, less than about 5, less than about 3.5, less than about 3, less than about 2, less than about 1, or less than about 0, determined at 25° C.

In certain embodiments, the hydrophobic acid may be chosen, at least in part, on the basis of the difference between the $pK_a$ of the hydrophobic acid and the $pK_a$ of a protonated nitrogen-containing therapeutic agent. For example, in some instances, the difference between the $pK_a$ of the hydrophobic acid and the $pK_a$ of a protonated nitrogen-containing therapeutic agent may be between about 1 $pK_a$ unit and about 15 $pK_a$ units, in some embodiments between about 1 $pK_a$ unit and about 10 $pK_a$ units, in some embodiments between about 1 $pK_a$ unit and about 5 $pK_a$ units, in some embodiments between about 1 $pK_a$ unit and about 3 $pK_a$ units, in some embodiments between about 1 $pK_a$ unit and about 2 $pK_a$ units, in some embodiments between about 2 $pK_a$ units and about 15 $pK_a$ units, in some embodiments between about 2 $pK_a$ units and about 10 $pK_a$ units, in some embodiments between about 2 $pK_a$ units and about 5 $pK_a$ units, in some embodiments between about 2 $pK_a$ units and about 3 $pK_a$ units, in some embodiments between about 3 $pK_a$ units and about 15 $pK_a$ units, in some embodiments between about 3 $pK_a$ units and about 10 $pK_a$ units, in some embodiments between about 3 $pK_a$ units and about 5 $pK_a$ units, in some embodiments between about 4 $pK_a$ units and about 15 $pK_a$ units, in some embodiments between about 4 $pK_a$ units and about 10 $pK_a$ units, in some embodiments between about 4 $pK_a$ units and about 6 $pK_a$ units, in some embodiments between about 5 $pK_a$ units and about 15 $pK_a$ units, in some embodiments between about 5 $pK_a$ units and about 10 $pK_a$ units, in some embodiments between about 5 $pK_a$ units and about 7 $pK_a$ units, in some embodiments between about 7 $pK_a$ units and about 15 $pK_a$ units, in some embodiments between about 7 $pK_a$ units and about 9 $pK_a$ units, in some embodiments between about 9 $pK_a$ units and about 15 $pK_a$ units, in some embodiments between about 9 $pK_a$ units and about 11 $pK_a$ units, in some embodiments between about 11 $pK_a$ units and about 13 $pK_a$ units, and in some embodiments between about 13 $pK_a$ units and about 15 $pK_a$ units, determined at 25° C.

In some instances, the difference between the $pK_a$ of the hydrophobic acid and the $pK_a$ of a protonated nitrogen-containing therapeutic agent may be at least about 1 $pK_a$ unit, in some embodiments at least about 2 $pK_a$ units, in some embodiments at least about 3 $pK_a$ units, in some embodiments at least about 4 $pK_a$ units, in some embodiments at least about 5 $pK_a$ units, in some embodiments at least about 6 $pK_a$ units, in some embodiments at least about 7 $pK_a$ units, in some embodiments at least about 8 $pK_a$ units, in some embodiments at least about 9 $pK_a$ units, in some embodiments at least about 10 $pK_a$ units, and in some embodiments at least about 15 $pK_a$ units, determined at 25° C.

In some embodiments, the hydrophobic acid may have a log P of between about 2 and about 15, in some embodiments between about 5 and about 15, in some embodiments between about 5 and about 10, in some embodiments between about 2 and about 8, in some embodiments between about 4 and about 8, in some embodiments between about 2 and about 7, or in some embodiments between about 4 and about 7. In some instances, the hydrophobic acid may have a log P greater than about 2, greater than about 4, greater than about 5, or greater than 6.

In some embodiments, a contemplated hydrophobic acid may have a phase transition temperature that is advantageous, for example, for improving the properties of the therapeutic nanoparticles. For instance, the acid may have a melting point of less than about 300° C., in some cases less than about 100° C., and in some cases less than about 50° C. In certain embodiments, the acid may have a melting point of between about 5° C. and about 25° C., in some cases between about 15° C. and about 50° C., in some cases between about 30° C. and about 100° C., in some cases between about 75° C. and about 150° C., in some cases between about 125° C. and about 200° C., in some cases between about 150° C. and about 250° C., and in some cases between about 200° C. and about 300° C. In some cases, the acid may have a melting point of less than about 15° C., in some cases less than about 10° C., or in some cases less than about 0° C. In certain embodiments, the acid may have a melting point of between about −30° C. and about 0° C. or in some cases between about −20° C. and about −10° C.

For example, an acid for use in methods and nanoparticles disclosed herein may be chosen, at least in part, on the basis of the solubility of the protonatable nitrogen-containing therapeutic agent in a solvent comprising the acid. For example, in some embodiments, a protonatable nitrogen-containing therapeutic agent dissolved in a solvent comprising the acid may have a solubility of between about 15 mg/mL to about 200 mg/mL, between about 20 mg/mL to about 200 mg/mL, between about 25 mg/mL to about 200 mg/mL, between about 50 mg/mL to about 200 mg/mL, between about 75 mg/mL to about 200 mg/mL, between about 100 mg/mL to about 200 mg/mL, between about 125 mg/mL to about 175 mg/mL, between about 15 mg/mL to about 50 mg/mL, between about 25 mg/mL to about 75 mg/mL. In some embodiments, a protonatable nitrogen-containing therapeutic agent dissolved in a solvent comprising the acid may have a solubility greater than about 10 mg/mL, greater than about 50 mg/mL, or greater than about 100 mg/mL. In some embodiments, a protonatable nitrogen-containing therapeutic agent dissolved in a solvent comprising the hydrophobic acid (e.g., a first solution consisting of the therapeutic agent, solvent, and hydrophobic acid) may have a solubility of at least about 2 times greater, in some embodiments at least about 5 times greater, in some embodiments at least about 10 times greater, in some embodiments at least about 20 times greater, in some embodiments about 2 times to about 20 times greater or in some embodiments about 10 times to about 20 times greater than when the protonatable nitrogen-containing therapeutic agent is dissolved in a solvent that does not contain the hydrophobic acid (e.g., a second solution consisting of the therapeutic agent and the solvent).

In some instances, the concentration of acid in a drug solution (i.e., a protonatable nitrogen-containing therapeutic agent solution) may be between about 1 weight percent and about 30 weight percent, in some embodiments between about 2 weight percent and about 30 weight percent, in some embodiments between about 3 weight percent and about 30 weight percent, in some embodiments between about 4 weight percent and about 30 weight percent, in some embodiments between about 5 weight percent and about 30 weight percent, in some embodiments between about 6 weight percent and about 30 weight percent, in some embodiments between about 8 weight percent and about 30 weight percent, in some embodiments between about 10 weight percent and about 30 weight percent, in some embodiments between about 12 weight percent and about 30 weight percent, in some embodiments between about 14 weight percent and about 30 weight percent, in some embodiments between about 16 weight percent and about 30 weight percent, in some embodiments between about 1 weight percent and about 5 weight percent, in some embodiments between about 3 weight percent and about 9 weight percent, in some embodiments between about 6 weight percent and about 12 weight percent, in some embodiments between about 9 weight percent and about 15 weight percent, in some embodiments between about 12 weight percent and about 18 weight percent, and in some embodiments between about 15 weight percent and about 21 weight percent. In certain embodiments, the concentration of hydrophobic acid in a drug solution may be at least about 1 weight percent, in some embodiments at least about 2 weight percent, in some embodiments at least about 3 weight percent, in some embodiments at least about 5 weight percent, in some embodiments at least about 10 weight percent, in some embodiments at least about 15 weight percent, and in some embodiments at least about 20 weight percent.

In certain embodiments, the molar ratio of hydrophobic acid to protonatable nitrogen-containing therapeutic agent (e.g., initially during formulation of the nanoparticles and/or in the nanoparticles) may be between about 0.25:1 to about 6:1, in some embodiments between about 0.25:1 to about 5:1, in some embodiments between about 0.25:1 to about 4:1, in some embodiments between about 0.25:1 to about 3:1, in some embodiments between about 0.25:1 to about 2:1, in some embodiments between about 0.25:1 to about 1.5:1, in some embodiments between about 0.25:1 to about 1:1, in some embodiments between about 0.25:1 to about 0.5:1, in some embodiments between about 0.5:1 to about 6:1, in some embodiments between about 0.5:1 to about 5:1, in some embodiments between about 0.5:1 to about 4:1, in some embodiments between about 0.5:1 to about 3:1, in some embodiments between about 0.5:1 to about 2:1, in some embodiments between about 0.5:1 to about 1.5:1, in some embodiments between about 0.5:1 to about 1:1, in some embodiments between about 0.5:1 to about 0.75:1, in some embodiments between about 0.75:1 to about 2:1, in some embodiments between about 0.75:1 to about 1.5:1, in some embodiments between about 0.75:1 to about 1.25:1, in some embodiments between about 0.9:1 to about 1.1:1, in some embodiments between about 0.95:1 to about 1.05:1, in some embodiments about 1:1, in some embodiments between about 0.75:1 to about 1:1, in some embodiments between about 1:1 to about 6:1, in some embodiments between about 1:1 to about 5:1, in some embodiments between about 1:1 to about 4:1, in some embodiments between about 1:1 to about 3:1, in some embodiments between about 1:1 to about 2:1, in some embodiments between about 1:1 to about 1.5:1, in some embodiments between about 1.5:1 to about 6:1, in some embodiments between about 1.5:1 to about 5:1, in some embodiments between about 1.5:1 to about 4:1, in some embodiments between about 1.5:1 to about 3:1, in some embodiments between about 2:1 to about 6:1, in some embodiments between about 2:1 to about 4:1, in some embodiments between about 3:1 to about 6:1, in some embodiments between about 3:1 to about 5:1, and in some embodiments between about 4:1 to about 6:1.

In some instances, the initial molar ratio of hydrophobic acid to protonatable nitrogen-containing therapeutic agent (i.e., during formulation of the nanoparticles) may be different from the molar ratio of hydrophobic acid to protonatable nitrogen-containing therapeutic agent in the nanoparticles (i.e., after removal of unencapsulated hydrophobic acid and protonatable nitrogen-containing therapeutic agent). In other instances, the initial molar ratio of hydrophobic acid to protonatable nitrogen-containing therapeutic agent (i.e., during formulation of the nanoparticles) may be essentially the same as the molar ratio of hydrophobic acid to protonatable nitrogen-containing therapeutic agent in the nanoparticles (i.e., after removal of unencapsulated hydrophobic acid and protonatable nitrogen-containing therapeutic agent).

In some cases, a solution containing the protonatable nitrogen-containing therapeutic agent may be prepared separately from a solution containing the polymer, and the two solutions may then be combined prior to nanoparticle formulation. For instance, in one embodiment, a first solution contains the protonatable nitrogen-containing therapeutic agent and the hydrophobic acid, and a second solution contains the polymer and optionally the hydrophobic acid. Formulations where the second solution does not contain the hydrophobic acid may be advantageous, for example, for minimizing the amount of hydrophobic acid used in a process or, in some cases, for minimizing contact time between the hydrophobic acid and, e.g., a polymer that can degrade in the presence of the hydrophobic acid. In other cases, a single solution may be prepared containing the protonatable nitrogen-containing therapeutic agent, polymer, and hydrophobic acid.

In some embodiments, the hydrophobic ion pair may be formed prior to formulation of the nanoparticles. For example, a solution containing the hydrophobic ion pair may be prepared prior to formulating the contemplated nanoparticles (e.g., by preparing a solution containing suitable amounts of the protonatable nitrogen-containing therapeutic agent and the hydrophobic acid). In other embodiments, the hydrophobic ion pair may be formed during formulation of the nanoparticles. For example, a first solution containing the protonatable nitrogen-containing therapeutic agent and a second solution containing the hydrophobic acid may be combined during a process step for preparing the nanoparticles (e.g., prior to emulsion formation and/or during emulsion formation). In certain embodiments, the hydrophobic ion pair may form prior to encapsulation of the protonatable nitrogen-containing therapeutic agent and hydrophobic acid in a contemplated nanoparticle. In other embodiments, the hydrophobic ion pair may form in the nanoparticle, e.g., after encapsulation of the protonatable nitrogen-containing therapeutic agent and hydrophobic acid.

In certain embodiments, the hydrophobic acid may have a solubility of less than about 2 g per 100 mL of water, in some embodiments less than about 1 g per 100 mL of water, in some embodiments less than about 100 mg per 100 mL of water, in some embodiments less than about 10 mg per 100 mL of water, and in some embodiments less than about 1 mg per 100 mL of water, determined at 25° C. In other embodiments, the acid may have a solubility of between about 1 mg per 100 mL of water to about 2 g per 100 mL of water, in some embodiments between about 1 mg per 100 mL of water to about 1 g per 100 mL of water, in some embodiments between about 1 mg per 100 mL of water to about 500 mg per 100 mL of water, and in some embodiments between about 1 mg per 100 mL of water to about 100 mg per 100 mL of water, determined at 25° C. In some embodiments, the hydrophobic acid may be essentially insoluble in water at 25° C.

In some embodiments, disclosed nanoparticles may be essentially free of the hydrophobic acid used during the preparation of the nanoparticles. In other embodiments, disclosed nanoparticles may comprise the hydrophobic acid. For instance, in some embodiments, the acid content in disclosed nanoparticles may be between about 0.05 weight percent to about 35 weight percent, in some embodiments between about 0.05 weight percent to about 30 weight percent, in some embodiments between about 0.5 weight percent to about 30 weight percent, in some embodiments between about 1 weight percent to about 30 weight percent, in some embodiments between about 2 weight percent to about 30 weight percent, in some embodiments between about 3 weight percent to about 30 weight percent, in some embodiments between about 5 weight percent to about 30 weight percent, in some embodiments between about 7 weight percent to about 30 weight percent, in some embodiments between about 10 weight percent to about 30 weight percent, in some embodiments between about 15 weight percent to about 30 weight percent, in some embodiments between about 20 weight percent to about 30 weight percent, in some embodiments between about 0.05 weight percent to about 0.5 weight percent, in some embodiments between about 0.05 weight percent to about 5 weight percent, in some embodiments between about 1 weight percent to about 5 weight percent, in some embodiments between about 3 weight percent to about 10 weight percent, in some embodiments between about 5 weight percent to about 15 weight percent, and in some embodiments between about 10 weight percent to about 20 weight percent.

In some embodiments, disclosed nanoparticles substantially immediately release (e.g., over about 1 minute to about 30 minutes, about 1 minute to about 25 minutes, about 5 minutes to about 30 minutes, about 5 minutes to about 1 hour, about 1 hour, or about 24 hours) less than about 2%, less than about 5%, less than about 10%, less than about 15%, less than about 20%, less than about 25%, less than about 30%, or less than 40% of the protonatable nitrogen-containing therapeutic agent, for example when placed in a phosphate buffer solution at room temperature (e.g., 25° C.) and/or at 37° C. In certain embodiments, nanoparticles comprising a protonatable nitrogen-containing therapeutic agent may release the protonatable nitrogen-containing therapeutic agent when placed in an aqueous solution (e.g., a phosphate buffer solution), e.g., at 25° C. and/or at 37° C., at a rate substantially corresponding to about 0.01 to about 50%, in some embodiments about 0.01 to about 25%, in some embodiments about 0.01 to about 15%, in some embodiments about 0.01 to about 10%, in some embodiments about 1 to about 40%, in some embodiments about 5 to about 40%, and in some embodiments about 10 to about 40% of the protonatable nitrogen-containing therapeutic agent released over about 1 hour. In some embodiments, nanoparticles comprising a protonatable nitrogen-containing therapeutic agent may release the protonatable nitrogen-containing therapeutic agent when placed in an aqueous solution (e.g., a phosphate buffer solution), e.g., at 25° C. and/or at 37° C., at a rate substantially corresponding to about 10 to about 70%, in some embodiments about 10 to about 45%, in some embodiments about 10 to about 35%, or in some embodiments about 10 to about 25%, of the protonatable nitrogen-containing therapeutic agent released over about 4 hours.

In some embodiments, disclosed nanoparticles may substantially retain the protonatable nitrogen-containing therapeutic agent, e.g., for at least about 1 minute, at least about 1 hour, or more, when placed in a phosphate buffer solution at 37° C.

In one embodiment, disclosed therapeutic nanoparticles may include a targeting ligand, e.g., a low-molecular weight ligand. In certain embodiments, the low-molecular weight ligand is conjugated to a polymer, and the nanoparticle comprises a certain ratio of ligand-conjugated polymer (e.g., PLA-PEG-Ligand) to non-functionalized polymer (e.g., PLA-PEG or PLGA-PEG). The nanoparticle can have an optimized ratio of these two polymers such that an effective amount of ligand is associated with the nanoparticle for treatment of a disease or disorder, such as cancer. For example, an increased ligand density may increase target binding (cell binding/target uptake), making the nanoparticle "target specific." Alternatively, a certain concentration of non-functionalized polymer (e.g., non-functionalized PLGA-PEG copolymer) in the nanoparticle can control inflammation and/or immunogenicity (i.e., the ability to provoke an immune response), and allow the nanoparticle to have a circulation half-life that is adequate for the treatment of a disease or disorder. Furthermore, the non-functionalized polymer may, in some embodiments, lower the rate of clearance from the circulatory system via the reticuloendothelial system (RES). Thus, the non-functionalized polymer may provide the nanoparticle with characteristics that may allow the particle to travel through the body upon administration. In some embodiments, a non-functionalized polymer may balance an otherwise high concentration of ligands, which can otherwise accelerate clearance by the subject, resulting in less delivery to the target cells.

In some embodiments, nanoparticles disclosed herein may include functionalized polymers conjugated to a ligand that constitute approximately 0.1-50, e.g., 0.1-30, e.g., 0.1-20, e.g., 0.1-10 mole percent of the entire polymer composition of the nanoparticle (i.e., functionalized+non-functionalized polymer). Also disclosed herein, in another embodiment, are nanoparticles that include a polymer conjugated (e.g., covalently with (i.e., through a linker (e.g., an alkylene linker)) or a bond) with one or more low-molecular weight ligands, wherein the weight percent low-molecular weight ligand with respect to total polymer is between about 0.001 and 5, e.g., between about 0.001 and 2, e.g., between about 0.001 and 1.

In some embodiments, disclosed nanoparticles may be able to bind efficiently to or otherwise associate with a biological entity, for example, a particular membrane component or cell surface receptor. Targeting of a therapeutic agent (e.g., to a particular tissue or cell type, to a specific diseased tissue but not to normal tissue, etc.) is desirable for the treatment of tissue specific diseases such as solid tumor cancers (e.g., prostate cancer). For example, in contrast to systemic delivery of a cytotoxic anti-cancer agent, the nanoparticles disclosed herein may substantially prevent the agent from killing healthy cells. Additionally, disclosed nanoparticles may allow for the administration of a lower dose of the agent (as compared to an effective amount of agent administered without disclosed nanoparticles or formulations) which may reduce the undesirable side effects commonly associated with traditional chemotherapy.

In general, a "nanoparticle" refers to any particle having a diameter of less than 1000 nm, e.g., about 10 nm to about 200 nm. Disclosed therapeutic nanoparticles may include nanoparticles having a diameter of about 60 to about 120 nm, or about 70 to about 120 nm, or about 80 to about 120 nm, or about 90 to about 120 nm, or about 100 to about 120 nm, or about 60 to about 130 nm, or about 70 to about 130 nm, or about 80 to about 130 nm, or about 90 to about 130 nm, or about 100 to about 130 nm, or about 110 to about 130 nm, or about 60 to about 140 nm, or about 70 to about 140 nm, or about 80 to about 140 nm, or about 90 to about 140 nm, or about 100 to about 140 nm, or about 110 to about 140 nm, or about 60 to about 150 nm, or about 70 to about 150 nm, or about 80 to about 150 nm, or about 90 to about 150 nm, or about 100 to about 150 nm, or about 110 to about 150 nm, or about 120 to about 150 nm.

Polymers

In some embodiments, the nanoparticles may comprise a matrix of polymers and a therapeutic agent. In some embodiments, a therapeutic agent and/or targeting moiety (i.e., a low-molecular weight ligand) can be associated with at least part of the polymeric matrix. For example, in some embodiments, a targeting moiety (e.g., ligand) can be covalently to associated with the surface of a polymeric matrix. In some embodiments, covalent association is mediated by a linker. The therapeutic agent can be associated with the surface of, encapsulated within, surrounded by, and/or dispersed throughout the polymeric matrix.

A wide variety of polymers and methods for forming particles therefrom are known in the art of drug delivery. In some embodiments, the disclosure is directed toward nanoparticles with at least two macromolecules, wherein the first macromolecule comprises a first polymer bound to a low-molecular weight ligand (e.g., targeting moiety); and the second macromolecule comprising a second polymer that is not bound to a targeting moiety. The nanoparticle can optionally include one or more additional, unfunctionalized, polymers.

Any suitable polymer can be used in the disclosed nanoparticles. Polymers can be natural or unnatural (synthetic) polymers. Polymers can be homopolymers or copolymers comprising two or more monomers. In terms of sequence, copolymers can be random, block, or comprise a combination of random and block sequences. Typically, polymers are organic polymers.

The term "polymer," as used herein, is given its ordinary meaning as used in the art, i.e., a molecular structure comprising one or more repeat units (monomers), connected by covalent bonds. The repeat units may all be identical, or in some cases, there may be more than one type of repeat unit present within the polymer. In some cases, the polymer can be biologically derived, i.e., a biopolymer. Non-limiting examples include peptides or proteins. In some cases, additional moieties may also be present in the polymer, for example biological moieties such as those described below. If more than one type of repeat unit is present within the polymer, then the polymer is said to be a "copolymer." It is to be understood that in any embodiment employing a polymer, the polymer being employed may be a copolymer in some cases. The repeat units forming the copolymer may be arranged in any fashion. For example, the repeat units may be arranged in a random order, in an alternating order, or as a block copolymer, i.e., comprising one or more regions each comprising a first repeat unit (e.g., a first block), and one or more regions each comprising a second repeat unit (e.g., a second block), etc. Block copolymers may have two (a diblock copolymer), three (a triblock copolymer), or more numbers of distinct blocks.

Disclosed particles can include copolymers, which, in some embodiments, describes two or more polymers (such as those described herein) that have been associated with each other, usually by covalent bonding of the two or more polymers together. Thus, a copolymer may comprise a first polymer and a second polymer, which have been conjugated together to form a block copolymer where the first polymer can be a first block of the block copolymer and the second polymer can be a second block of the block copolymer. Of course, those of ordinary skill in the art will understand that a block copolymer may, in some cases, contain multiple blocks of polymer, and that a "block copolymer," as used herein, is not limited to only block copolymers having only a single first block and a single second block. For instance, a block copolymer may comprise a first block comprising a first polymer, a second block comprising a second polymer, and a third block comprising a third polymer or the first polymer, etc. In some cases, block copolymers can contain any number of first blocks of a first polymer and second blocks of a second polymer (and in certain cases, third blocks, fourth blocks, etc.). In addition, it should be noted that block copolymers can also be formed, in some instances, from other block copolymers. For example, a first block copolymer may be conjugated to another polymer (which may be a homopolymer, a biopolymer, another block copolymer, etc.), to form a new block copolymer containing multiple types of blocks, and/or to other moieties (e.g., to non-polymeric moieties).

In some embodiments, the polymer (e.g., copolymer, e.g., block copolymer) can be amphiphilic, i.e., having a hydrophilic portion and a hydrophobic portion, or a relatively hydrophilic portion and a relatively hydrophobic portion. A hydrophilic polymer can be one generally that attracts water and a hydrophobic polymer can be one that generally repels water. A hydrophilic or a hydrophobic polymer can be identified, for example, by preparing a sample of the polymer and measuring its contact angle with water (typically, the polymer will have a contact angle of less than 60°, while a hydrophobic polymer will have a contact angle of greater than about 60°). In some cases, the hydrophilicity of two or more polymers may be measured relative to each other, i.e., a first polymer may be more hydrophilic than a second polymer. For instance, the first polymer may have a smaller contact angle than the second polymer.

In one set of embodiments, a polymer (e.g., copolymer, e.g., block copolymer) contemplated herein includes a biocompatible polymer, i.e., the polymer that does not typically induce an adverse response when inserted or injected into a living subject, for example, without significant inflammation and/or acute rejection of the polymer by the immune system, for instance, via a T-cell response. Accordingly, the therapeutic particles contemplated herein can be non-immunogenic. The term non-immunogenic as used herein refers to endogenous growth factor in its native state which normally elicits no, or only minimal levels of, circulating antibodies, T-cells, or reactive immune cells, and which normally does not elicit in the individual an immune response against itself.

Biocompatibility typically refers to the acute rejection of material by at least a portion of the immune system, i.e., a nonbiocompatible material implanted into a subject provokes an immune response in the subject that can be severe enough such that the rejection of the material by the immune system cannot be adequately controlled, and often is of a degree such that the material must be removed from the subject. One simple test to determine biocompatibility can be to expose a polymer to cells in vitro; biocompatible polymers are polymers that typically will not result in significant cell death at moderate concentrations, e.g., at concentrations of 50 micrograms/$10^6$ cells. For instance, a biocompatible polymer may cause less than about 20% cell death when exposed to cells such as fibroblasts or epithelial cells, even if phagocytosed or otherwise uptaken by such cells. Non-limiting examples of biocompatible polymers that may be useful in various embodiments include polydioxanone (PDO), polyhydroxyalkanoate, polyhydroxybutyrate, poly(glycerol sebacate), polyglycolide (i.e., poly(glycolic) acid) (PGA), polylactide (i.e., poly(lactic) acid) (PLA), poly(lactic) acid-co-poly(glycolic) acid (PLGA), polycaprolactone, or copolymers or derivatives including these and/or other polymers.

In certain embodiments, contemplated biocompatible polymers may be biodegradable, i.e., the polymer is able to degrade, chemically and/or biologically, within a physiological environment, such as within the body. As used herein, "biodegradable" polymers are those that, when introduced into cells, are broken down by the cellular machinery (biologically degradable) and/or by a chemical process, such as hydrolysis, (chemically degradable) into components that the cells can either reuse or dispose of without significant toxic effect on the cells. In one embodiment, the biodegradable polymer and their degradation byproducts can be biocompatible.

Particles disclosed herein may or may not contain PEG. In addition, certain embodiments can be directed towards copolymers containing poly(ester-ether)s, e.g., polymers having repeat units joined by ester bonds (e.g., R—C(O)—O—R' bonds) and ether bonds (e.g., R—O—R' bonds). In some embodiments, a biodegradable polymer, such as a hydrolyzable polymer, containing carboxylic acid groups, may be conjugated with poly(ethylene glycol) repeat units to form a poly(ester-ether). A polymer (e.g., copolymer, e.g., block copolymer) containing poly(ethylene glycol) repeat units can also be referred to as a "PEGylated" polymer.

For instance, a contemplated polymer may be one that hydrolyzes spontaneously upon exposure to water (e.g., within a subject), or the polymer may degrade upon exposure to heat (e.g., at temperatures of about 37° C.). Degradation of a polymer may occur at varying rates, depending on the polymer or copolymer used. For example, the half-life of the polymer (the time at which 50% of the polymer can be degraded into monomers and/or other nonpolymeric moieties) may be on the order of days, weeks, months, or years, depending on the polymer. The polymers may be biologically degraded, e.g., by enzymatic activity or cellular machinery, in some cases, for example, through exposure to a lysozyme (e.g., having relatively low pH). In some cases, the polymers may be broken down into monomers and/or other nonpolymeric moieties that cells can either reuse or dispose of without significant toxic effect on the cells (for example, polylactide may be hydrolyzed to form lactic acid, polyglycolide may be hydrolyzed to form glycolic acid, etc.).

In some embodiments, polymers may be polyesters, including copolymers comprising lactic acid and glycolic acid units, such as poly(lactic acid-co-glycolic acid) and poly(lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; PEGylated polymers and copolymers of lactide and glycolide (e.g., PEGylated PLA, PEGylated PGA, PEGylated PLGA, and derivatives thereof). In some embodiments, polyesters include, for example, polyanhydrides, poly(ortho ester) PEGylated poly(ortho ester), poly(caprolactone), PEGylated poly(caprolactone), polylysine, PEGylated polylysine, poly(ethylene imine), PEGylated poly(ethylene imine), poly(L-lactide-co-L-lysine), poly(serine ester), poly(4-hydroxy-L-proline ester), poly[α-(4-aminobutyl)-L-glycolic acid], and derivatives thereof.

In some embodiments, a polymer may be PLGA. PLGA is a biocompatible and biodegradable co-polymer of lactic acid and glycolic acid, and various forms of PLGA can be characterized by the ratio of lactic acid:glycolic acid. Lactic acid can be L-lactic acid, D-lactic acid, or D,L-lactic acid. The degradation rate of PLGA can be adjusted by altering the lactic acid-glycolic acid ratio. In some embodiments, PLGA can be characterized by a lactic acid:glycolic acid ratio of approximately 85:15, approximately 75:25, approximately 60:40, approximately 50:50, approximately 40:60, approximately 25:75, or approximately 15:85. In some embodiments, the ratio of lactic acid to glycolic acid monomers in the polymer of the particle (e.g., the PLGA block copolymer or PLGA-PEG block copolymer), may be selected to optimize for various parameters such as water uptake, therapeutic agent release and/or polymer degradation kinetics can be optimized.

In some embodiments, polymers may be one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, amino alkyl methacrylate copolymer, poly(acrylic acid), poly(methacrylic acid), methacrylic acid alkylamide copolymer, poly(methyl methacrylate), poly(methacrylic acid polyacrylamide, amino alkyl methacrylate copolymer, glycidyl methacrylate copolymers, polycyanoacrylates, and combinations comprising one or more of the foregoing polymers. The acrylic polymer may comprise fully-polymerized copolymers of acrylic and methacrylic acid esters with a low content of quaternary ammonium groups.

In some embodiments, polymers can be cationic polymers. In general, cationic polymers are able to condense and/or protect negatively charged strands of nucleic acids (e.g., DNA, RNA, or derivatives thereof). Amine-containing polymers such as poly(lysine), polyethylene imine (PEI), and poly(amidoamine) dendrimers are contemplated for use, in some embodiments, in a disclosed particle.

In some embodiments, polymers can be degradable polyesters bearing cationic side chains. Examples of these polyesters include poly(L-lactide-co-L-lysine), poly(serine ester), poly(4-hydroxy-L-proline ester).

It is contemplated that PEG may be terminated and include an end group, for example, when PEG is not conjugated to a ligand. For example, PEG may terminate in a hydroxyl, a methoxy or other alkoxyl group, a methyl or other alkyl group, an aryl group, a carboxylic acid, an amine, an amide, an acetyl group, a guanidino group, or an imidazole. Other contemplated end groups include azide, alkyne, maleimide, aldehyde, hydrazide, hydroxylamine, alkoxyamine, or thiol moieties.

Those of ordinary skill in the art will know of methods and techniques for PEGylating a polymer, for example, by using EDC (1-ethyl-3-(3-dimethylaminopropyl) carbodiimide hydrochloride) and NHS (N-hydroxysuccinimide) to react a polymer to a PEG group terminating in an amine, by ring opening polymerization techniques (ROMP), or the like.

In one embodiment, the molecular weight (or e.g., the ratio of molecular weights of, e.g., different blocks of a copolymer) of the polymers can be optimized for effective treatment as disclosed herein. For example, the molecular weight of a polymer may influence particle degradation rate (such as when the molecular weight of a biodegradable polymer can be adjusted), solubility, water uptake, and drug release kinetics. For example, the molecular weight of the polymer (or e.g., the ratio of molecular weights of, e.g., different blocks of a copolymer) can be adjusted such that the particle biodegrades in the subject being treated within a reasonable period of time (ranging from a few hours to 1-2 weeks, 3-4 weeks, 5-6 weeks, 7-8 weeks, etc.).

A disclosed particle can for example comprise a diblock copolymer of PEG and PL(G)A, wherein for example, the PEG portion may have a number average molecular weight of about 1,000-20,000, e.g., about 2,000-20,000, e.g., about 2 to about 10,000, and the PL(G)A portion may have a number average molecular weight of about 5,000 to about 20,000, or about 5,000-100,000, e.g., about 20,000-70,000, e.g., about 15,000-50,000.

For example, disclosed here is an exemplary therapeutic nanoparticle that includes about 10 to about 99 weight percent poly(lactic) acid-poly(ethylene)glycol copolymer or poly(lactic)-co-poly (glycolic) acid-poly(ethylene)glycol copolymer, or about 20 to about 80 weight percent, about 40 to about 80 weight percent, or about 30 to about 50 weight percent, or about 70 to about 90 weight percent poly(lactic) acid-poly(ethylene)glycol copolymer or poly(lactic)-co-poly (glycolic) acid-poly(ethylene)glycol copolymer. Exemplary poly(lactic) acid-poly(ethylene)glycol copolymers can include a number average molecular weight of about 15 to about 20 kDa, or about 10 to about 25 kDa of poly(lactic) acid and a number average molecular weight of about 4 to about 6, or about 2 kDa to about 10 kDa of poly(ethylene) glycol.

In some embodiments, the poly(lactic) acid-poly(ethylene)glycol copolymer may have a poly(lactic) acid number average molecular weight fraction of about 0.6 to about 0.95, in some embodiments between about 0.7 to about 0.9, in some embodiments between about 0.6 to about 0.8, in some embodiments between about 0.7 to about 0.8, in some embodiments between about 0.75 to about 0.85, in some embodiments between about 0.8 to about 0.9, and in some embodiments between about 0.85 to about 0.95. It should be understood that the poly(lactic) acid number average molecular weight fraction may be calculated by dividing the number average molecular weight of the poly(lactic) acid component of the copolymer by the sum of the number average molecular weight of the poly(lactic) acid component and the number average molecular weight of the poly (ethylene)glycol component.

Disclosed nanoparticles may optionally include about 1 to about 50 weight percent poly(lactic) acid or poly(lactic) acid-co-poly (glycolic) acid (which does not include PEG), or may optionally include about 1 to about 50 weight percent, or about 10 to about 50 weight percent or about 30 to about 50 weight percent poly(lactic) acid or poly(lactic) acid-co-poly (glycolic) acid. For example, poly(lactic) or poly(lactic)-co-poly(glycolic) acid may have a number average molecule weight of about 5 to about 15 kDa, or about 5 to about 12 kDa. Exemplary PLA may have a number average molecular weight of about 5 to about 10 kDa. Exemplary PLGA may have a number average molecular weight of about 8 to about 12 kDa.

A therapeutic nanoparticle may, in some embodiments, contain about 10 to about 30 weight percent, in some embodiments about 10 to about 25 weight percent, in some embodiments about 10 to about 20 weight percent, in some embodiments about 10 to about 15 weight percent, in some embodiments about 15 to about 20 weight percent, in some embodiments about 15 to about 25 weight percent, in some embodiments about 20 to about 25 weight percent, in some embodiments about 20 to about 30 weight percent, or in some embodiments about 25 to about 30 weight percent of poly(ethylene)glycol, where the poly(ethylene)glycol may be present as a poly(lactic) acid-poly(ethylene)glycol copolymer, poly(lactic)-co-poly (glycolic) acid-poly(ethylene) glycol copolymer, or poly(ethylene)glycol homopolymer. In certain embodiments, the polymers of the nanoparticles can be conjugated to a lipid. The polymer can be, for example, a lipid-terminated PEG.

Targeting Moieties

Provided herein, in some embodiments, are nanoparticles that may include an optional targeting moiety, i.e., a moiety able to bind to or otherwise associate with a biological entity, for example, a membrane component, a cell surface receptor, an antigen, or the like. A targeting moiety present on the surface of the particle may allow the particle to become localized at a particular targeting site, for instance, a tumor, a disease site, a tissue, an organ, a type of cell, etc. As such, the nanoparticle may then be "target specific." The drug or other payload may then, in some cases, be released from the particle and allowed to interact locally with the particular targeting site.

In one embodiment, a disclosed nanoparticle includes a targeting moiety that is a low-molecular weight ligand. The term "bind" or "binding," as used herein, refers to the interaction between a corresponding pair of molecules or portions thereof that exhibit mutual affinity or binding capacity, typically due to specific or non-specific binding or interaction, including, but not limited to, biochemical, physiological, and/or chemical interactions. "Biological binding" defines a type of interaction that occurs between pairs of molecules including proteins, nucleic acids, glycoproteins, carbohydrates, hormones, or the like. The term "binding partner" refers to a molecule that can undergo binding with a particular molecule. "Specific binding" refers to molecules, such as polynucleotides, that are able to bind to or recognize a binding partner (or a limited number of binding partners) to a substantially higher degree than to other, similar biological entities. In one set of embodiments, the targeting moiety has an affinity (as measured via a disassociation constant) of less than about 1 micromolar, at least about 10 micromolar, or at least about 100 micromolar.

For example, a targeting portion may cause the particles to become localized to a tumor (e.g., a solid tumor), a disease site, a tissue, an organ, a type of cell, etc. within the body of a subject, depending on the targeting moiety used.

For example, a low-molecular weight ligand may become localized to a solid tumor, e.g., breast or prostate tumors or cancer cells. The subject may be a human or non-human animal. Examples of subjects include, but are not limited to, a mammal such as a dog, a cat, a horse, a donkey, a rabbit, a cow, a pig, a sheep, a goat, a rat, a mouse, a guinea pig, a hamster, a primate, a human or the like.

Contemplated targeting moieties may include small molecules. In certain embodiments, the term "small molecule" refers to organic compounds, whether naturally-occurring or artificially created (e.g., via chemical synthesis) that have relatively low molecular weight and that are not proteins, polypeptides, or nucleic acids. Small molecules typically have multiple carbon-carbon bonds. In certain embodiments, small molecules are less than about 2000 g/mol in size. In some embodiments, small molecules are less than about 1500 g/mol or less than about 1000 g/mol. In some embodiments, small molecules are less than about 800 g/mol or less than about 500 g/mol, for example about 100 g/mol to about 600 g/mol, or about 200 g/mol to about 500 g/mol.

In some embodiments, the low-molecular weight ligand is of the Formulae I, II, III or IV:

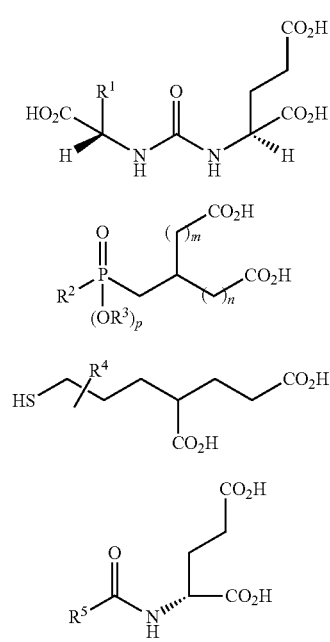

and enantiomers, stereoisomers, rotamers, tautomers, diastereomers, or racemates thereof;

wherein m and n are each, independently, 0, 1, 2 or 3; p is 0 or 1;

$R^1$, $R^2$, $R^4$, and $R^5$ are each, independently, selected from the group consisting of substituted or unsubstituted alkyl (e.g., $C_{1-10}$-alkyl, $C_{1-6}$-alkyl, or $C_{1-4}$-alkyl), substituted or unsubstituted aryl (e.g., phenyl or pyridinyl), and any combination thereof; and $R^3$ is H or $C_{1-6}$-alkyl (e.g., $CH_3$).

For compounds of Formulae I, II, III and IV, $R^1$, $R^2$, $R^4$ or $R^5$ comprise points of attachment to the nanoparticle, e.g., a point of attachment to a polymer that forms part of a disclosed nanoparticle, e.g., PEG. The point of attachment may be formed by a covalent bond, ionic bond, hydrogen bond, a bond formed by adsorption including chemical adsorption and physical adsorption, a bond formed from van der Waals bonds, or dispersion forces. For example, if $R^1$, $R^2$, $R^4$, or $R^5$ are defined as an aniline or $C_{1-6}$-alkyl-$NH_2$ group, any hydrogen (e.g., an amino hydrogen) of these functional groups could be removed such that the low-molecular weight ligand is covalently bound to the polymeric matrix (e.g., the PEG-block of the polymeric matrix) of the nanoparticle. As used herein, the term "covalent bond" refers to a bond between two atoms formed by sharing at least one pair of electrons.

In particular embodiments of the Formulae I, II, III or IV, $R^1$, $R^2$, $R^4$, and $R^5$ are each, independently, $C_{1-6}$-alkyl or phenyl, or any combination of $C_{1-6}$-alkyl or phenyl, which are independently substituted one or more times with OH, SH, $NH_2$, or $CO_2H$, and wherein the alkyl group may be interrupted by N(H), S, or O. In another embodiment, $R^1$, $R^2$, $R^4$, and $R^5$ are each, independently, $CH_2$-Ph, $(CH_2)_2$—SH, $CH_2$—SH, $(CH_2)_2C(H)(NH_2)CO_2H$, $CH_2C(H)(NH_2)CO_2H$, $CH(NH_2)CH_2CO_2H$, $(CH_2)_2C(H)(SH)CO_2H$, $CH_2$—N(H)-Ph, O—$CH_2$-Ph, or O—$(CH_2)_2$-Ph, wherein each Ph may be independently substituted one or more times with OH, $NH_2$, $CO_2H$, or SH. For these formulae, the $NH_2$, OH or SH groups serve as the point of covalent attachment to the nanoparticle (e.g., —N(H)—PEG, —O-PEG, or —S-PEG).

Exemplary ligands include:

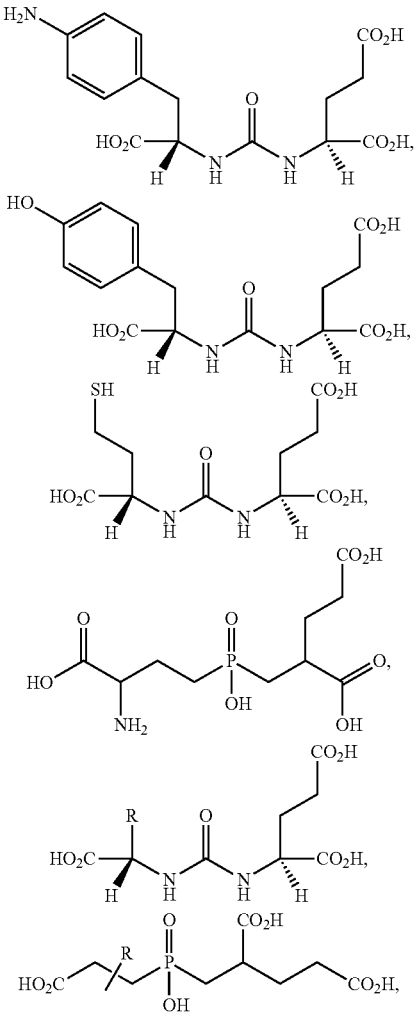

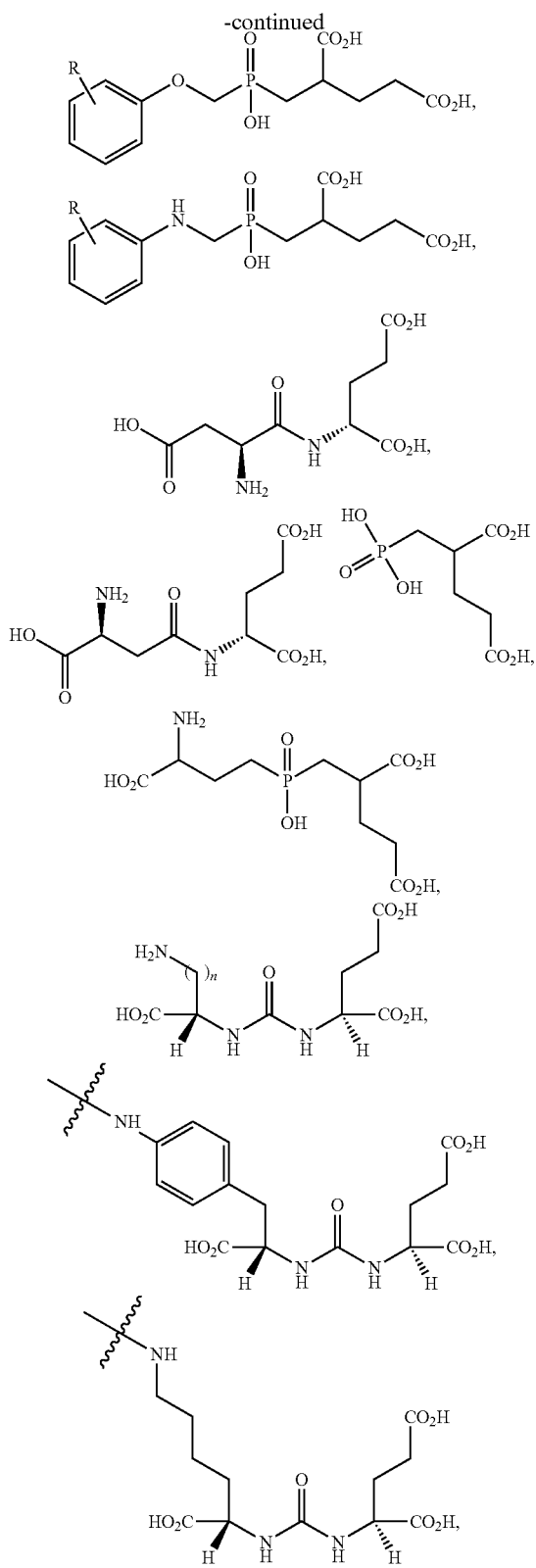

and enantiomers, stereoisomers, rotamers, tautomers, diastereomers, or racemates thereof, wherein the $NH_2$, OH, or SH groups serve as the point of covalent attachment to the nanoparticle (e.g., —N(H)—PEG, —O-PEG, or —S-PEG) or indicates the point of attachment to the nanoparticle, wherein n is 1, 2, 3, 4, 5, or 6, and wherein R is independently selected from the group consisting of $NH_2$, SH, OH, $CO_2H$, $C_{1-6}$-alkyl that is substituted with $NH_2$, SH, OH, or $CO_2H$, and phenyl that is substituted with $NH_2$, SH, OH, or $CO_2H$, and wherein R serves as the point of covalent attachment to the nanoparticle (e.g., —N(H)—PEG, —S-PEG, —O-PEG, or $CO_2$—PEG). These compounds may be further substituted with $NH_2$, SH, OH, $CO_2H$, $C_{1-6}$-alkyl that is substituted with $NH_2$, SH, OH, or $CO_2H$, or phenyl that is substituted with $NH_2$, SH, OH or $CO_2H$, wherein these functional groups can also serve as the point of covalent attachment to the nanoparticle.

In some embodiments, small molecule targeting moieties that may be used to target cells associated with solid tumors such as prostate or breast cancer tumors include PSMA peptidase inhibitors such as 2-PMPA, GPI5232, VA-033, phenylalkylphosphonamidates and/or analogs and derivatives thereof. In some embodiments, small molecule targeting moieties that may be used to target cells associated with prostate cancer tumors include thiol and indole thiol derivatives, such as 2-MPPA and 3-(2-mercaptoethyl)-1H-indole-2-carboxylic acid derivatives. In some embodiments, small molecule targeting moieties that may be used to target cells associated with prostate cancer tumors include hydroxamate derivatives. In some embodiments, small molecule targeting moieties that may be used to target cells associated with prostate cancer tumors include PBDA- and urea-based inhibitors, such as ZJ 43, ZJ 11, ZJ 17, ZJ 38 and/or and analogs and derivatives thereof, androgen receptor targeting agents (ARTAs), polyamines, such as putrescine, spermine, and spermidine, inhibitors of the enzyme glutamate carboxylase II (GCPII), also known as NAAG Peptidase or NAALADase.

In another embodiment, the targeting moiety can be a ligand that targets Her2, EGFR, folate receptor or toll receptors. In another embodiment, the targeting moiety is folate, folic acid, or an EGFR binding molecule.

For example, contemplated the targeting moieties may include a nucleic acid, polypeptide, glycoprotein, carbohydrate, or lipid. For example, a targeting moiety can be a nucleic acid targeting moiety (e.g. an aptamer, e.g., the A10 aptamer) that binds to a cell type specific marker. In general, an aptamer is an oligonucleotide (e.g., DNA, RNA, or an analog or derivative thereof) that binds to a particular target, such as a polypeptide. In some embodiments, a targeting moiety may be a naturally occurring or synthetic ligand for a cell surface receptor, e.g., a growth factor, hormone, LDL, transferrin, etc. A targeting moiety can be an antibody, which term is intended to include antibody fragments. Characteristic portions of antibodies, single chain targeting moieties can be identified, e.g., using procedures such as phage display.

Targeting moieties may be a targeting peptide or targeting peptidomimetic that has a length of up to about 50 residues. For example, a targeting moiety may include the amino acid sequence AKERC, CREKA, ARYLQKLN, or AXYLZZLN, wherein X and Z are variable amino acids, or conservative variants or peptidomimetics thereof. In particular embodiments, the targeting moiety is a peptide that includes the amino acid sequence AKERC, CREKA, ARYLQKLN, or AXYLZZLN, wherein X and Z are variable amino acids, and has a length of less than 20, 50 or 100 residues. The CREKA (Cys Arg Glu Lys Ala) peptide or a peptidomimetic thereof or the octapeptide AXYLZZLN are also contemplated as targeting moieties, as well as peptides, or conservative variants or peptidomimetics thereof, that bind or form a complex with collagen IV, or that target tissue basement membrane (e.g., the basement membrane of a blood vessel). Exemplary targeting moieties include peptides that target ICAM (intercellular adhesion molecule, e.g., ICAM-1).

Targeting moieties disclosed herein can be, in some embodiments, conjugated to a disclosed polymer or copolymer (e.g., PLA-PEG), and such a polymer conjugate may form part of a disclosed nanoparticle.

In some embodiments, a therapeutic nanoparticle may include a polymer-drug conjugate. For example, a drug may be conjugated to a disclosed polymer or copolymer (e.g., PLA-PEG), and such a polymer-drug conjugate may form part of a disclosed nanoparticle. For example, a disclosed therapeutic nanoparticle may optionally include about 0.2 to about 30 weight percent of a PLA-PEG or PLGA-PEG, wherein the PEG is functionalized with a drug (e.g., PLA-PEG-Drug).

A disclosed polymeric conjugate (e.g., a polymer-ligand conjugate) may be formed using any suitable conjugation technique. For instance, two compounds such as a targeting moiety or drug and a biocompatible polymer (e.g., a biocompatible polymer and a poly(ethylene glycol)) may be conjugated together using techniques such as EDC-NHS chemistry (1-ethyl-3-(3-dimethylaminopropyl) carbodiimide hydrochloride and N-hydroxysuccinimide) or a reaction involving a maleimide or a carboxylic acid, which can be conjugated to one end of a thiol, an amine, or a similarly functionalized polyether. The conjugation of a targeting moiety or drug and a polymer to form a polymer-targeting moiety conjugate or a polymer-drug conjugate can be performed in an organic solvent, such as, but not limited to, dichloromethane, acetonitrile, chloroform, dimethylformamide, tetrahydrofuran, acetone, or the like. Specific reaction conditions can be determined by those of ordinary skill in the art using no more than routine experimentation.

In another set of embodiments, a conjugation reaction may be performed by reacting a polymer that comprises a carboxylic acid functional group (e.g., a poly(ester-ether) compound) with a polymer or other moiety (such as a targeting moiety or drug) comprising an amine. For instance, a targeting moiety, such as a low-molecular weight ligand, or a drug, such as dasatinib, may be reacted with an amine to form an amine-containing moiety, which can then be conjugated to the carboxylic acid of the polymer. Such a reaction may occur as a single-step reaction, i.e., the conjugation is performed without using intermediates such as N-hydroxysuccinimide or a maleimide. In some embodiments, a drug may be reacted with an amine-containing linker to form an amine-containing drug, which can then be conjugated to the carboxylic acid of the polymer as described above. The conjugation reaction between the amine-containing moiety and the carboxylic acid-terminated polymer (such as a poly(ester-ether) compound) may be achieved, in one set of embodiments, by adding the amine-containing moiety, solubilized in an organic solvent such as (but not limited to) dichloromethane, acetonitrile, chloroform, tetrahydrofuran, acetone, formamide, dimethylformamide, pyridines, dioxane, or dimethylsulfoxide, to a solution containing the carboxylic acid-terminated polymer. The carboxylic acid-terminated polymer may be contained within an organic solvent such as, but not limited to, dichloromethane, acetonitrile, chloroform, dimethylformamide, tetrahydrofuran, or acetone. Reaction between the amine-containing moiety and the carboxylic acid-terminated polymer may occur spontaneously, in some cases. Unconjugated reactants may be washed away after such reactions, and the polymer may be precipitated in solvents such as, for instance, ethyl ether, hexane, methanol, or ethanol. In certain embodiments, a conjugate may be formed between an alcohol-containing moiety and carboxylic acid functional group of a polymer, which can be achieved similarly as described above for conjugates of amines and carboxylic acids.

Preparation of Nanoparticles

Another aspect of this disclosure is directed to systems and methods of making disclosed nanoparticles. In some embodiments, using two or more different polymers (e.g., copolymers, e.g., block copolymers) in different ratios and producing particles from the polymers (e.g., copolymers, e.g., block copolymers), properties of the particles be controlled. For example, one polymer (e.g., copolymer, e.g., block copolymer) may include a low-molecular weight ligand, while another polymer (e.g., copolymer, e.g., block copolymer) may be chosen for its biocompatibility and/or its ability to control immunogenicity of the resultant particle.

In some embodiments, a solvent used in a nanoparticle preparation process (e.g., a nanoprecipitation process or a nanoemulsion process as discussed below) may include a hydrophobic acid, which may confer advantageous properties to the nanoparticles prepared using the process. As discussed above, in some cases, the hydrophobic acid may improve drug loading of disclosed nanoparticles. Furthermore, in some instances, the controlled release properties of disclosed nanoparticles may be improved by the use of the hydrophobic acid. In some cases, the hydrophobic acid may be included in, for example, an organic solution or an aqueous solution used in the process. In one embodiment, the drug is combined with an organic solution and the hydrophobic acid and optionally one or more polymers. The hydrophobic acid concentration in a solution used to dissolve the drug is discussed above and may be, for example, between about 1 weight percent and about 30 weight percent, etc.

In one set of embodiments, the particles are formed by providing a solution comprising one or more polymers, and contacting the solution with a polymer nonsolvent to produce the particle. The solution may be miscible or immiscible with the polymer nonsolvent. For example, a water-miscible liquid such as acetonitrile may contain the polymers, and particles are formed as the acetonitrile is contacted with water, a polymer nonsolvent, e.g., by pouring the acetonitrile into the water at a controlled rate. The polymer contained within the solution, upon contact with the polymer nonsolvent, may then precipitate to form particles such as nanoparticles. Two liquids are said to be "immiscible" or not miscible, with each other when one is not soluble in the other to a level of at least 10% by weight at ambient temperature and pressure. Typically, an organic solution (e.g., dichloromethane, acetonitrile, chloroform, tetrahydrofuran, acetone, formamide, dimethylformamide, pyridines, dioxane, dimethylsulfoxide, etc.) and an aqueous liquid (e.g., water, or water containing dissolved salts or other species, cell or biological media, ethanol, etc.) are immiscible with respect to each other. For example, the first solution may be poured into the second solution (at a suitable rate or speed). In some cases, particles such as nanoparticles may be formed as the first solution contacts the immiscible second liquid, e.g., precipitation of the polymer upon contact causes the polymer to form nanoparticles while the first solution is poured into the second liquid, and in some cases, for example, when the rate of introduction is carefully controlled and kept at a relatively slow rate, nanoparticles may form. The control of such particle formation can be readily optimized by one of ordinary skill in the art using only routine experimentation.

Properties such as surface functionality, surface charge, size, zeta (ξ) potential, hydrophobicity, ability to control immunogenicity, and the like, may be highly controlled using a disclosed process. For instance, a library of particles may be synthesized, and screened to identify the particles having a particular ratio of polymers that allows the particles to have a specific density of moieties (e.g., low-molecular weight ligands) present on the surface of the particle. This allows particles having one or more specific properties to be prepared, for example, a specific size and a specific surface density of moieties, without an undue degree of effort. Accordingly, certain embodiments are directed to screening techniques using such libraries, as well as any particles identified using such libraries. In addition, identification may occur by any suitable method. For instance, the identification may be direct or indirect, or proceed quantitatively or qualitatively.

In some embodiments, already-formed nanoparticles are functionalized with a targeting moiety using procedures analogous to those described for producing ligand-functionalized polymeric conjugates. For example, a first copolymer (PLGA-PEG, poly(lactide-co-glycolide) and poly(ethylene glycol)) is mixed with the protonatable nitrogen-containing therapeutic agent to form particles. The particles are then associated with a low-molecular weight ligand to form nanoparticles that can be used for the treatment of cancer. The particles can be associated with varying amounts of low-molecular weight ligands in order to control the ligand surface density of the nanoparticle, thereby altering the therapeutic characteristics of the nanoparticle. Furthermore, for example, by controlling parameters such as molecular weight, the molecular weight of PEG, and the nanoparticle surface charge, very precisely controlled particles may be obtained.

Figure 2A:
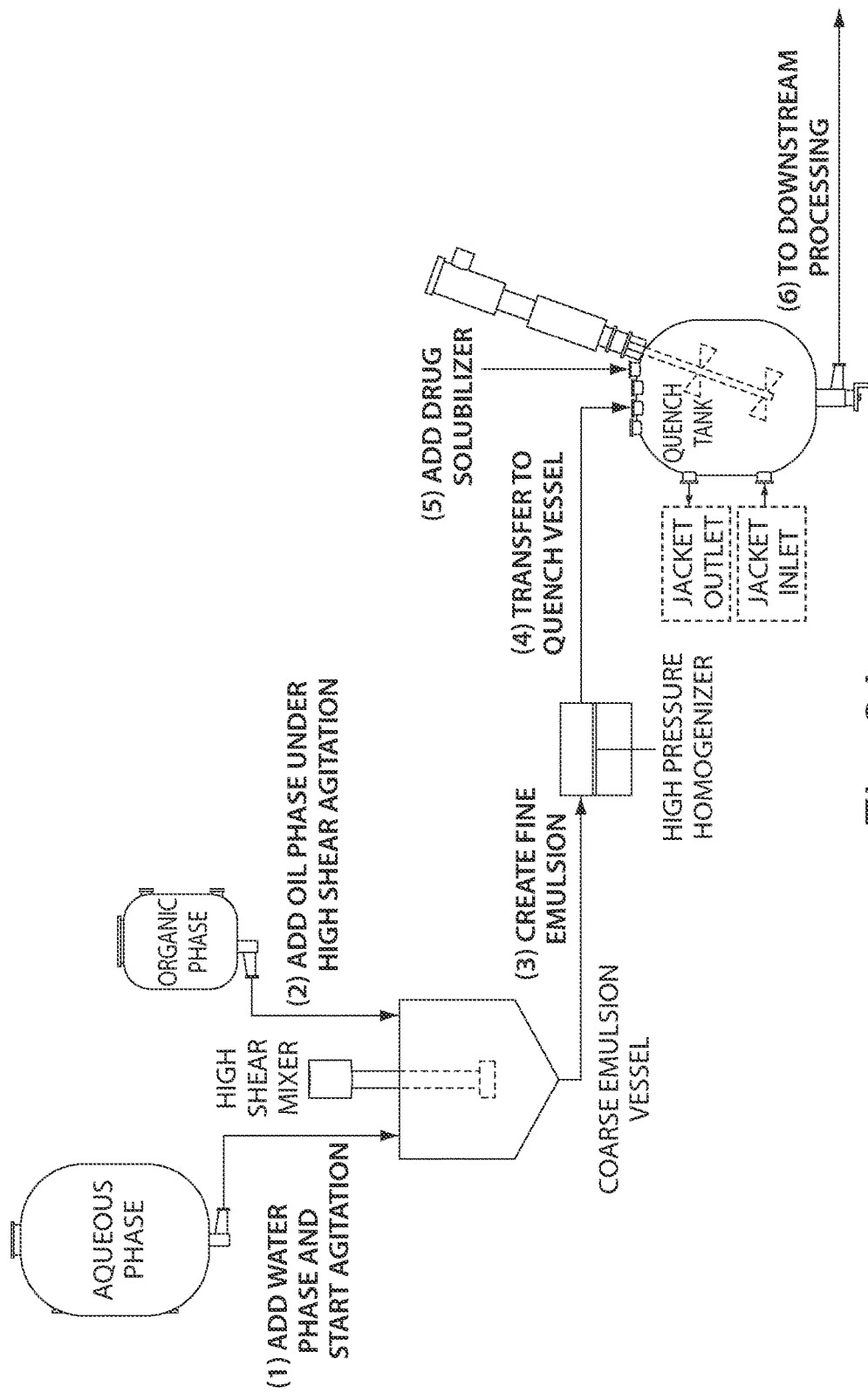
FIGS. 2A and 2B show flow diagrams for a disclosed emulsion process.
Figure 2B:
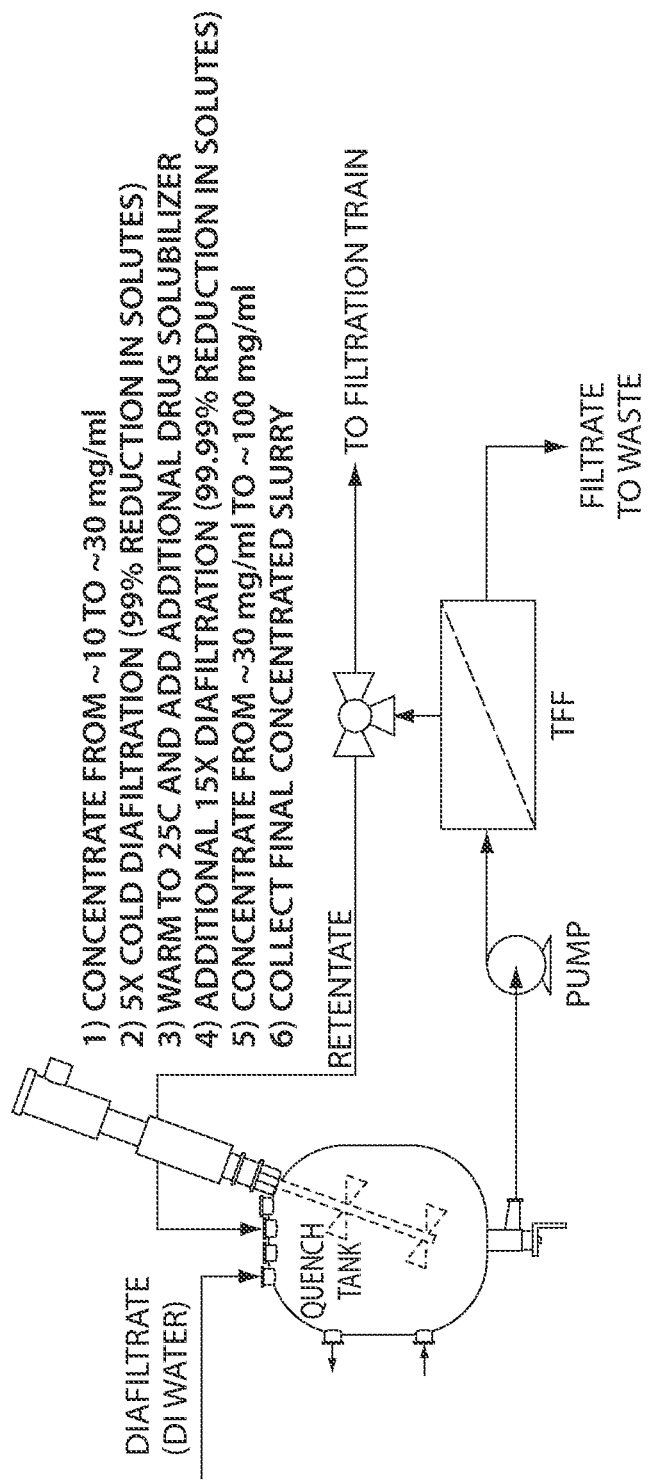

In another embodiment, a nanoemulsion process is provided, such as the process represented in FIGS. 1, 2A, and 2B. For example, a protonatable nitrogen-containing therapeutic agent (e.g., dasatinib), a hydrophobic acid, a first polymer (for example, a diblock co-polymer such as PLA-PEG or PLGA-PEG, either of which may be optionally bound to a ligand) and an optional second polymer (e.g., (PL(G)A-PEG or PLA), may be combined with an organic solution to form a first organic phase. Such first phase may include about 1 to about 50% weight solids, about 5 to about 50% weight solids, about 5 to about 40% weight solids, about 1 to about 15% weight solids, or about 10 to about 30% weight solids. The first organic phase may be combined with a first aqueous solution to form a second phase. The organic solution can include, for example, toluene, methyl ethyl ketone, acetonitrile, tetrahydrofuran, ethyl acetate, isopropyl alcohol, isopropyl acetate, dimethylformamide, methylene chloride, dichloromethane, chloroform, acetone, benzyl alcohol, Tween 80, Span 80, or the like, and combinations thereof. In an embodiment, the organic phase may include benzyl alcohol, ethyl acetate, and combinations thereof. The second phase can be between about 0.1 and 50 weight %, between about 1 and 50 weight %, between about 5 and 40 weight %, or between about 1 and 15 weight %, solids. The aqueous solution can be water, optionally in combination with one or more of sodium cholate, ethyl acetate, polyvinyl acetate and benzyl alcohol. In some embodiments, the pH of the aqueous phase may be selected based on the $pK_a$ of the protonated basic therapeutic agent and/or the $pK_a$ of the hydrophobic acid. For example, in certain embodiments, the basic therapeutic agent, when protonated, may have a first $pK_a$, the hydrophobic acid may have a second $pK_a$, and the aqueous phase may have a pH equal to a $pK_a$ unit between the first $pK_a$ and the second $pK_a$. In a particular embodiment, the pH of the aqueous phase may be equal to a $pK_a$ unit that is about equidistant between the first $pK_a$ and the second $pK_a$.

For example, the oil or organic phase may use a solvent that is only partially miscible with the nonsolvent (water). Therefore, when mixed at a low enough ratio and/or when using water pre-saturated with the organic solvents, the oil phase remains liquid. The oil phase may be emulsified into an aqueous solution and, as liquid droplets, sheared into nanoparticles using, for example, high energy dispersion systems, such as homogenizers or sonicators. The aqueous portion of the emulsion, otherwise known as the "water phase", may be surfactant solution consisting of sodium cholate and pre-saturated with ethyl acetate and benzyl alcohol. In some instances, the organic phase (e.g., first organic phase) may include the basic therapeutic agent. Additionally, in certain embodiments, the aqueous solution (e.g., first aqueous solution) may include the substantially hydrophobic acid. In other embodiments, both the basic therapeutic agent and the substantially hydrophobic acid may be dissolved in the organic phase.

Emulsifying the second phase to form an emulsion phase may be performed, for example, in one or two emulsification steps. For example, a primary emulsion may be prepared, and then emulsified to form a fine emulsion. The primary emulsion can be formed, for example, using simple mixing, a high pressure homogenizer, probe sonicator, stir bar, or a rotor stator homogenizer. The primary emulsion may be formed into a fine emulsion through the use of e.g., probe sonicator or a high pressure homogenizer, e.g., by using 1, 2, 3, or more passes through a homogenizer. For example, when a high pressure homogenizer is used, the pressure used may be about 30 to about 60 psi, about 40 to about 50 psi, about 1000 to about 8000 psi, about 2000 to about 4000 psi, about 4000 to about 8000 psi, or about 4000 to about 5000 psi, e.g., about 2000, 2500, 4000 or 5000 psi.

In some cases, fine emulsion conditions, which can be characterized by a very high surface to volume ratio of the droplets in the emulsion, can be chosen to maximize the solubility of the protonatable nitrogen-containing therapeutic agent and hydrophobic acid and form the desired HIP. In certain embodiments, under fine emulsion conditions, equilibration of dissolved components can occur very quickly, i.e., faster than solidification of the nanoparticles. Thus, selecting a HIP based on, e.g., the $pK_a$ difference between the protonatable nitrogen-containing therapeutic agent and the hydrophobic acid, or adjusting other parameters such as the pH of the fine emulsion and/or the pH of the quench solution, can have a significant impact on the drug loading and release properties of the nanoparticles by dictating, for example, the formation of a HIP in the nanoparticle as opposed to diffusion of the protonatable nitrogen-containing therapeutic agent and/or hydrophobic acid out of the nanoparticle.

In some embodiments, the basic therapeutic agent (e.g., protonatable nitrogen-containing therapeutic agent) and the substantially hydrophobic acid may be combined in the second phase prior to emulsifying the second phase. In some instances, the basic therapeutic agent and the substantially hydrophobic acid may form a hydrophobic ion pair prior to emulsifying the second phase. In other embodiments, the basic therapeutic agent and the substantially hydrophobic acid may form a hydrophobic ion pair during emulsification of the second phase. For example, the basic therapeutic agent and the substantially hydrophobic acid may be combined in the second phase substantially concurrently with emulsifying the second phase, e.g., the basic therapeutic agent and the substantially hydrophobic acid may be dissolved in separate solutions (e.g., two substantially immiscible solutions), which are then combined during emulsification. In another example, the basic therapeutic agent and the substantially hydrophobic acid may be dissolved in separate miscible solutions that are then fed into second phase during emulsification.

Either solvent evaporation or dilution may be needed to complete the extraction of the solvent and solidify the particles. For better control over the kinetics of extraction and a more scalable process, a solvent dilution via aqueous quench may be used. For example, the emulsion can be diluted into cold water to a concentration sufficient to dissolve all of the organic solvent to form a quenched phase. In some embodiments, quenching may be performed at least partially at a temperature of about 5° C. or less. For example, water used in the quenching may be at a temperature that is less than room temperature (e.g., about 0 to about 10° C., or about 0 to about 5° C.).

In certain embodiments, the quench may be chosen having a pH that is advantageous for quenching the emulsion phase, e.g., by improving the properties of the nanoparticles, such as the release profile, or improving a nanoparticle parameter, such as the drug loading. The pH of the quench may be adjusted by acid or base titration, for example, or by appropriate selection of a buffer.

In some embodiments, the pH of the quench may be selected based on the $pK_a$ of the protonoated basic therapeutic agent and/or the $pK_a$ of the hydrophobic acid. For example, in certain embodiments, the basic therapeutic agent, when protonated, may have a first $pK_a$, the hydrophobic acid may have a second $pK_a$, and the emulsion phase may be quenched with an aqueous solution having a pH equal to a $pK_a$ unit between the first $pK_a$ and the second $pK_a$. In some embodiments, the resultant quenched phase may also have a pH equal to a $pK_a$ unit between the first $pK_a$ and the second $pK_a$. In a particular embodiment, the pH may be equal to a $pK_a$ unit that is about equidistant between the first $pK_a$ and the second $pK_a$.

In some embodiments, the quench may have a pH between about 2 and about 12, in some embodiments between about 3 and about 10, in some embodiments between about 3 and about 9, in some embodiments between about 3 and about 8, in some embodiments between about 3 and about 7, in some embodiments between about 4 and about 8, in some embodiments between about 4 and about 7, in some embodiments between about 4 and about 6, in some embodiments between about 4 and about 5, in some embodiments between about 4.2 and about 4.8, in some embodiments between about 6 and about 10, in some embodiments between about 6 and about 9, in some embodiments between about 6 and about 8, in some embodiments between about 6 and about 7. In certain embodiments, the quench may have a pH of about 4.5. It should be understood that the pH of a buffer solution may vary as a function of temperature. Unless otherwise specified, the pH of a buffer solution referred to herein is the pH at 23° C.

In some embodiments, the quench may be an aqueous solution comprising a buffering agent (i.e., a buffer solution). Any suitable buffering agent may be used. Non-limiting examples of buffering agents include phosphate, citrate, acetate, borate, imidazole, MES (4-morpholineethanesulfonic acid), bis-tris (Bis(2-hydroxyethyl)amino-tris(hydroxymethyl)methane), ADA (N-(2-Acetamido)iminodiacetic acid), ACES (N-(2-Acetamido)-2-aminoethanesulfonic acid), PIPES (1,4-Piperazinediethanesulfonic acid), MOPSO (3-Morpholino-2-hydroxypropanesulfonic acid), bis-tris propane (1,3-Bis[tris(hydroxymethyl)methylamino]propane), BES (N,N-Bis(2-hydroxyethyl)-2-aminoethanesulfonic acid), MOPS (3-(N-Morpholino)propanesulfonic acid), TES (2-[(2-Hydroxy-1,1-bis(hydroxymethyl)ethyl)amino]ethanesulfonic acid), HEPES (4-(2-Hydroxyethyl)piperazine-1-ethanesulfonic acid), DIPSO (3-(N,N-Bis[2-hydroxyethyl]amino)-2-hydroxypropanesulfonic acid), MOBS (4-(N-Morpholino)butanesulfonic acid), TAPSO (2-Hydroxy-3-[tris(hydroxymethyl)methylamino]-1-propanesulfonic acid), Trizma (2-Amino-2-(hydroxymethyl)-1,3-propanediol), HEPPSO (4-(2-Hydroxyethyl)piperazine-1-(2-hydroxypropanesulfonic acid)), POPSO (Piperazine-N,N'-bis(2-hydroxypropanesulfonic acid)), TEA (triethylamine), EPPS (4-(2-Hydroxyethyl)-1-piperazinepropanesulfonic acid), tricine (N-[Tris(hydroxymethyl)methyl]glycine), Gly-Gly (Diglycine), bicine (N,N-Bis(2-hydroxyethyl) glycine), HEPBS (N-(2-Hydroxyethyl)piperazine-N'-(4-butanesulfonic acid)), TAPS (N-[Tris(hydroxymethyl)methyl]-3-aminopropanesulfonic acid), AMPD (2-Amino-2-methyl-1,3-propanediol), TABS (N-tris(Hydroxymethyl)methyl-4-aminobutanesulfonic acid), AMPSO (N-(1,1-Dimethyl-2-hydroxyethyl)-3-amino-2-hydroxypropanesulfonic acid), CHES (2-(Cyclohexylamino)ethanesulfonic acid), CAPSO (3-(Cyclohexylamino)-2-hydroxy-1-propanesulfonic acid), AMP (β-Aminoisobutyl alcohol), CAPS (3-(Cyclohexylamino)-1-propanesulfonic acid), CABS (4-(Cyclohexylamino)-1-butanesulfonic acid), and combinations thereof. It should be understood that a buffer comprises an acid and a base in equilibrium (e.g., an acid and a conjugate base and/or a base and a conjugate acid). Thus, it should further be understood that, for brevity, a buffer solution or buffering agent may be referred to herein by the name of a free acid (e.g., phosphoric acid) or its conjugate base (e.g., phosphate), or the name of a free base (e.g., imidazole) or its conjugate acid (e.g., imidazolium), but that one of ordinary skill in the art would understand that an equilibrium exists between two or more different protonation species of the buffering agent (e.g., $H_3PO_4$, $H_2PO_4^-$, $HPO_4^{2-}$, and $PO_4^{3-}$). In some embodiments, the quench may comprise two or more buffering agents. For example, the quench may comprise two, three, four, or five buffering agents. In some embodiments, the quench may comprise a mixture of phosphate and citrate. In other embodiments, the quench may comprise a mixture of borate, phosphate, and acetate (e.g., Britton-Robbinson buffer, which comprises 0.04 M $H_3BO_3$, 0.04 M $H_3PO_4$, and 0.04 M $CH_3COOH$ titrated to a desired pH).

In some embodiments, a buffer solution (i.e., a quench) may have a suitable buffering capacity within a particular pH range. Non-limiting pH ranges for exemplary buffer solutions are provided in Table A below. In certain embodiments, a buffer solution may have a buffering agent concentration between about 0.001M and about 1M, in some embodiments between about 0.001M and about 0.5M, in some embodiments between about 0.01M and about 0.5M, in some embodiments between about 0.05M and about 0.5M, in some embodiments between about 0.1M and about 0.5M, in some embodiments between about 0.01M and about 0.2M, in some embodiments between about 0.05M and about 0.15M, and in some embodiments between about 0.075M and about 0.125M.

TABLE A

Non-limiting pH ranges for exemplary buffers.

| Buffering agent | pH range |
|---|---|
| Phosphate | 5.7-8.0 |
| Citrate | 3.0-6.2 |
| Phosphate-Citrate | 2.6-7.6 |
| Acetate | 3.7-5.6 |
| Imidazole | 6.2-7.8 |
| Britton-Robbinson | 2-12 |
| ADA | 6.0-7.2 |
| ACES | 6.1-7.5 |
| PIPES | 6.1-7.5 |
| MOPSO | 6.2-7.6 |
| Bis-tris Propane | 6.3-9.5 |
| BES | 6.4-7.8 |
| MOPS | 6.5-7.9 |
| TES | 6.8-8.2 |
| HEPES | 6.8-8.2 |
| DIPSO | 7.0-8.2 |
| MOBS | 6.9-8.3 |

In some embodiments, a quench may have a buffering agent concentration sufficient to resist a substantial pH change. For example, a quenched phase may have a pH that differs from the pH of the emulsion phase by less than 1 pH unit, in some embodiments less than 0.5 pH units, in some embodiments, less than 0.2 pH units, in some embodiments less than 0.1 pH units, and in some embodiments less than 0.05 pH units. In some embodiments, the pH of the quenched phase may be substantially the same as the pH of the emulsion phase (i.e., prior to quenching).

In some embodiments, the quenched phase may have a pH between about 2 and about 12, in some embodiments between about 3 and about 10, in some embodiments between about 3 and about 9, in some embodiments between about 3 and about 8, in some embodiments between about 3 and about 7, in some embodiments between about 4 and about 8, in some embodiments between about 4 and about 7, in some embodiments between about 4 and about 6, in some embodiments between about 4 and about 5, in some embodiments between about 4 and about 6, in some embodiments between about 4.2 and about 4.8, in some embodiments between about 6 and about 10, in some embodiments between about 6 and about 9, in some embodiments between about 6 and about 8, in some embodiments between about 6 and about 7. In certain embodiments, the quenched phase may have a pH of about 4.6.

A buffering solution (e.g., a quench) at a desired pH can be readily prepared by one of ordinary skill in the art. For example, a buffering solution at a desired pH can prepared by titrating a solution containing a buffering agent with a strong acid (e.g., HCl) or strong base (e.g., NaOH). Alternatively, a buffering solution at a desired pH can prepared by combining a weak acid (e.g., citric acid) with its conjugate base (e.g., sodium citrate) or by combining a weak base (e.g., imidazole) with its conjugate acid (e.g., imidazolium chloride). One of ordinary skill in the art could determine the amounts of the weak acid or weak base and corresponding conjugate to use in preparing a buffering solution by using the Henderson-Hasselbalch equation.

In certain embodiments, HIP formation can occur during or after emulsification, e.g., as a result of equilibrium conditions in the fine emulsion. Without wishing to be bound by any theory, it is believed that organic-soluble counter ions (i.e., the hydrophobic acid) can facilitate diffusion of a hydrophilic therapeutic agent into a nanoparticle of an emulsion as a result of HIP formation. Without wishing to be bound by any theory, the HIP may remain in the nanoparticle before solidification of the nanoparticle since the solubility of the HIP in the nanoparticle is higher than the solubility of the HIP in the aqueous phase of the emulsion and/or in the quench. For example, by selecting a pH for the quench that is between the $pK_a$ of the basic therapeutic agent and the $pK_a$ of the hydrophobic acid, formation of ionized basic therapeutic agent and hydrophobic acid can be optimized. However, selecting a pH that is too high may tend to cause the hydrophobic acid to diffuse out of the nanoparticle, whereas selecting a pH that is too low may tend to cause the basic therapeutic agent to diffuse out of the nanoparticle.

In some embodiments, the pH of an aqueous solution used in a nanoparticle formulation process (e.g., including, but not limited to, the aqueous phase, the emulsion phase, the quench, and the quenched phase) may be independently selected and may be between about 1 and about 3, in some embodiments between about 2 and about 4, in some embodiments between about 3 and about 5, in some embodiments between about 4 and about 6, in some embodiments between about 5 and about 7, in some embodiments between about 6 and about 8, in some embodiments between about 7 and about 9, and in some embodiments between about 8 and about 10. In certain embodiments, the pH of an aqueous solution used in a nanoparticle formulation process may be between about 3 and about 4, in some embodiments between about 4 and about 5, in some embodiments between about 5 and about 6, in some embodiments between about 6 and about 7, in some embodiments between about 7 and about 8, and in some embodiments between about 8 and about 9.

In some embodiments, not all of the protonatable nitrogen-containing therapeutic agent is encapsulated in the particles at this stage, and a drug solubilizer is added to the quenched phase to form a solubilized phase. The drug solubilizer may be for example, Tween 80, Tween 20, polyvinyl pyrrolidone, cyclodextran, sodium dodecyl sulfate, sodium cholate, diethylnitrosamine, sodium acetate, urea, glycerin, propylene glycol, glycofurol, poly(ethylene) glycol, bris(polyoxyethyleneglycolddodecyl ether, sodium benzoate, sodium salicylate, or combinations thereof. For example, Tween-80 may be added to the quenched nanoparticle suspension to solubilize the free drug and prevent the formation of drug crystals. In some embodiments, a ratio of drug solubilizer to the protonatable nitrogen-containing therapeutic agent is about 200:1 to about 10:1, or in some embodiments about 100:1 to about 10:1.

The solubilized phase may be filtered to recover the nanoparticles. For example, ultrafiltration membranes may be used to concentrate the nanoparticle suspension and substantially eliminate organic solvent, free drug (i.e., unencapsulated therapeutic agent), drug solubilizer, and other processing aids (surfactants). Exemplary filtration may be performed using a tangential flow filtration system. For example, by using a membrane with a pore size suitable to retain nanoparticles while allowing solutes, micelles, and organic solvent to pass, nanoparticles can be selectively separated. Exemplary membranes with molecular weight cut-offs of about 300-500 kDa (~5-25 nm) may be used.

Diafiltration may be performed using a constant volume approach, meaning the diafiltrate (cold deionized water, e.g., about 0 to about 5° C., or 0 to about 10° C.) may added to the feed suspension at the same rate as the filtrate is removed from the suspension. In some embodiments, filtering may include a first filtering using a first temperature of about 0 to about 5° C., or 0 to about 10° C., and a second temperature of about 20 to about 30° C., or 15 to about 35° C. In some embodiments, filtering may include processing about 1 to about 30, in some cases about 1 to about 15, or in some cases 1 to about 6 diavolumes. For example, filtering may include processing about 1 to about 30, or in some cases about 1 to about 6 diavolumes, at about 0 to about 5° C., and processing at least one diavolume (e.g., about 1 to about 15, about 1 to about 3, or about 1 to about 2 diavolumes) at about 20 to about 30° C. In some embodiments, filtering comprises processing different diavolumes at different distinct temperatures.

After purifying and concentrating the nanoparticle suspension, the particles may be passed through one, two or more sterilizing and/or depth filters, for example, using ~0.2 µm depth pre-filter. For example, a sterile filtration step may involve filtering the therapeutic nanoparticles using a filtration train at a controlled rate. In some embodiments, the filtration train may include a depth filter and a sterile filter.

In another embodiment of preparing nanoparticles, an organic phase is formed composed of a mixture of a protonatable nitrogen-containing therapeutic agent, and polymer (homopolymer, co-polymer, and co-polymer with ligand). The organic phase is mixed with an aqueous phase at approximately a 1:5 ratio (oil phase:aqueous phase) where the aqueous phase is composed of a surfactant and some dissolved solvent. The primary emulsion is formed by the combination of the two phases under simple mixing or through the use of a rotor stator homogenizer. The primary emulsion is then formed into a fine emulsion through the use of a high pressure homogenizer. The fine emulsion is then quenched by addition to deionized water under mixing. In some embodiments, the quench:emulsion ratio may be about 2:1 to about 40:1, or in some embodiments about 5:1 to about 15:1. In some embodiments, the quench:emulsion ratio is approximately 8.5:1. Then a solution of Tween (e.g., Tween 80) is added to the quench to achieve approximately 2% Tween overall. This serves to dissolve free, unencapsulated protonatable nitrogen-containing therapeutic agent. The nanoparticles are then isolated through either centrifugation or ultrafiltration/diafiltration.

It will be appreciated that the amounts of polymer, protonatable nitrogen-containing therapeutic agent, and hydrophobic acid that are used in the preparation of the formulation may differ from a final formulation. For example, some of the protonatable nitrogen-containing therapeutic agent may not become completely incorporated in a nanoparticle and such free protonatable nitrogen-containing therapeutic agent may be e.g., filtered away. For example, in an embodiment, a first organic solution containing about 11 weight percent theoretical loading of protonatable nitrogen-containing therapeutic agent in a first organic solution containing about 9% of a first hydrophobic acid (e.g., a fatty acid), a second organic solution containing about 89 weight percent polymer (e.g., the polymer may include about 2.5 mol percent of a targeting moiety conjugated to a polymer and about 97.5 mol percent PLA-PEG), and an aqueous solution containing about 0.12% of a second hydrophobic acid (e.g., a bile acid) may be used in the preparation of a formulation that results in, e.g., a final nanoparticle comprising about 2 weight percent protonatable nitrogen-containing therapeutic agent, about 97.5 weight percent polymer (where the polymer may include about 1.25 mol percent of a targeting moiety conjugated to a polymer and about 98.75 mol percent PLA-PEG), and about 0.5% total hydrophobic acid. Such processes may provide final nanoparticles suitable for administration to a patient that includes about 1 to about 20 percent by weight therapeutic agent, e.g., about 1, about 2, about 3, about 4, about 5, about 8, about 10, or about 15 percent protonatable nitrogen-containing therapeutic agent by weight.

Therapeutic Agents

The protonatable nitrogen-containing therapeutic agent may include alternative forms such as pharmaceutically acceptable salt forms, free base forms, hydrates, isomers, and prodrugs thereof. In some embodiments, the protonatable nitrogen-containing therapeutic agent may be selected from a list of known agents, for example, a list of agents previously synthesized; a list of agents previously administered to a subject, for example, a human subject or a mammalian subject; a list of FDA approved agents; or a historical list of agents, for example, a historical list of a pharmaceutical company, etc. Suitable lists of known agents are well known to those of ordinary skill in the art and include, but are not limited to, the Merck Index and the FDA Orange Book, each of which is incorporated herein by reference. In some instances, combinations of two or more protonatable nitrogen-containing therapeutic agents (e.g., two, three, or more protonatable nitrogen-containing therapeutic agents) may be used in a disclosed nanoparticle formulation.

In some embodiments, the protonatable nitrogen-containing therapeutic agent may be tyrosine kinase inhibitor. For example, the tyrosine kinase may be a multi-targeted receptor tyrosine kinase inhibitor (e.g., sunitinib ($pK_a$=7.07)). In another example, the protonatable nitrogen-containing therapeutic agent may be a Bcr-Abl tyrosine-kinase inhibitor (e.g., imatinib ($pK_a$=8.38), nilotinib, dasatinib ($pK_a$=7.07), bosutinib, ponatinib, and bafetinib). In some embodiments, a Bcr-Abl tyrosine-kinase inhibitor may also inhibit an Src tyrosine kinase. Thus, in some embodiments, the protonatable nitrogen-containing therapeutic agent may be a Bcr-Abl and Src tyrosine-kinase inhibitor. A non-limiting example of a Bcr-Abl and Src tyrosine-kinase inhibitor is dasatinib.

Other non-limiting examples of protonatable nitrogen-containing therapeutic agents include chemotherapeutic agents such as doxorubicin (adriamycin), gemcitabine (gemzar), daunorubicin, procarbazine, mitomycin, cytarabine, vinorelbine, vinca alkaloids such as vinblastine or vincristine ($pK_a$=7.08); bleomycin, cladribine, camptothecin, CPT-11, 10-hydroxy-7-ethylcamptothecin (5N38), dacarbazine, S-I capecitabine, UFT, deoxycytidine, 5-azacytosine, 5-azadeoxycytosine, allopurinol, 2-chloroadenosine, trimetrexate, aminopterin, methylene-10-deazaaminopterin (MDAM), epirubicin, 9-aminocamptothecin, 10,11-methylenedioxycamptothecin, karenitecin, 9-nitrocamptothecin, TAS 103, vindesine, L-phenylalanine mustard, epothilones A-E, tomudex, 6-mercaptopurine, 6-thioguanine, amsacrine, karenitecin, acyclovir, valacyclovir, ganciclovir, amantadine, rimantadine, lamivudine, and combinations thereof.

In one set of embodiments, the payload is a drug or a combination of more than one drug. Such particles may be useful, for example, in embodiments where a targeting moiety may be used to direct a particle containing a drug to a particular localized location within a subject, e.g., to allow localized delivery of the drug to occur.

Pharmaceutical Formulations

Nanoparticles disclosed herein may be combined with pharmaceutically acceptable carriers to form a pharmaceutical composition, according to another aspect. As would be appreciated by one of skill in this art, the carriers may be chosen based on the route of administration as described below, the location of the target issue, the drug being delivered, the time course of delivery of the drug, etc.

The pharmaceutical compositions can be administered to a patient by any means known in the art including oral and parenteral routes. The term "patient," as used herein, refers to humans as well as non-humans, including, for example, mammals, birds, reptiles, amphibians, and fish. For instance, the non-humans may be mammals (e.g., a rodent, a mouse, a rat, a rabbit, a monkey, a dog, a cat, a primate, or a pig). In certain embodiments parenteral routes are desirable since they avoid contact with the digestive enzymes that are found in the alimentary canal. According to such embodiments, inventive compositions may be administered by injection (e.g., intravenous, subcutaneous or intramuscular, intraperitoneal injection), rectally, vaginally, topically (as by powders, creams, ointments, or drops), or by inhalation (as by sprays).

In a particular embodiment, the nanoparticles are administered to a subject in need thereof systemically, e.g., by IV infusion or injection.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In one embodiment, the inventive conjugate is suspended in a carrier fluid comprising 1% (w/v) sodium carboxymethyl cellulose and 0.1% (v/v) TWEEN™ 80. The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Solid dosage forms for oral administration include capsules, tablets, pills, powders, and granules. In such solid dosage forms, the encapsulated or unencapsulated conjugate is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

It will be appreciated that the exact dosage of a nanoparticle containing a protonatable nitrogen-containing therapeutic agent is chosen by the individual physician in view of the patient to be treated, in general, dosage and administration are adjusted to provide an effective amount of the protonatable nitrogen-containing therapeutic agent nanoparticle to the patient being treated. As used herein, the "effective amount" of a nanoparticle containing a protonatable nitrogen-containing therapeutic agent refers to the amount necessary to elicit the desired biological response. As will be appreciated by those of ordinary skill in this art, the effective amount of a nanoparticle containing a protonatable nitrogen-containing therapeutic agent may vary depending on such factors as the desired biological endpoint, the drug to be delivered, the target tissue, the route of administration, etc. For example, the effective amount of a nanoparticle containing a protonatable nitrogen-containing therapeutic agent might be the amount that results in a reduction in tumor size by a desired amount over a desired period of time. Additional factors which may be taken into account include the severity of the disease state; age, weight and gender of the patient being treated; diet, time and frequency of administration; drug combinations; reaction sensitivities; and tolerance/response to therapy.

The nanoparticles may be formulated in dosage unit form for ease of administration and uniformity of dosage. The expression "dosage unit form" as used herein refers to a physically discrete unit of nanoparticle appropriate for the patient to be treated. It will be understood, however, that the total daily usage of the compositions will be decided by the attending physician within the scope of sound medical judgment. For any nanoparticle, the therapeutically effective dose can be estimated initially either in cell culture assays or in animal models, usually mice, rabbits, dogs, or pigs. The animal model is also used to achieve a desirable concentration range and route of administration. Such information can then be used to determine useful doses and routes for administration in humans. Therapeutic efficacy and toxicity of nanoparticles can be determined by standard pharmaceutical procedures in cell cultures or experimental animals, e.g., $ED_{50}$ (the dose is therapeutically effective in 50% of the population) and $LD_{50}$ (the dose is lethal to 50% of the population). The dose ratio of toxic to therapeutic effects is the therapeutic index, and it can be expressed as the ratio, $LD_{50}/ED_{50}$. Pharmaceutical compositions which exhibit large therapeutic indices may be useful in some embodiments. The data obtained from cell culture assays and animal studies can be used in formulating a range of dosage for human use.

In an embodiment, compositions disclosed herein may include less than about 10 ppm of palladium, or less than about 8 ppm, or less than about 6 ppm of palladium. For example, provided here is a composition that includes nanoparticles having a polymeric conjugate wherein the composition has less than about 10 ppm of palladium.

In some embodiments, a composition suitable for freezing is contemplated, including nanoparticles disclosed herein and a solution suitable for freezing, e.g., a sugar such as a mono, di, or poly saccharide, e.g., sucrose and/or a trehalose, and/or a salt and/or a cyclodextrin solution is added to the nanoparticle suspension. The sugar (e.g., sucrose or trehalose) may act, e.g., as a cryoprotectant to prevent the particles from aggregating upon freezing. For example, provided herein is a nanoparticle formulation comprising a plurality of disclosed nanoparticles, sucrose, an ionic halide, and water; wherein the nanoparticles/sucrose/water/ionic halide is about 3-40%/10-40%/20-95%/0.1-10% (w/w/w/w) or about 5-10%/10-15%/80-90%/1-10% (w/w/w/w). For example, such solution may include nanoparticles as disclosed herein, about 5% to about 20% by weight sucrose and an ionic halide such as sodium chloride, in a concentration of about 10-100 mM. In another example, provided herein is a nanoparticle formulation comprising a plurality of disclosed nanoparticles, trehalose, cyclodextrin, and water; wherein the nanoparticles/trehalose/water/cyclodextrin is about 3-40%/1-25%/20-95%/1-25% (w/w/w/w) or about 5-10%/1-25%/80-90%/10-15% (w/w/w/w).

For example, a contemplated solution may include nanoparticles as disclosed herein, about 1% to about 25% by weight of a disaccharide such as trehalose or sucrose (e.g., about 5% to about 25% trehalose or sucrose, e.g. about 10% trehalose or sucrose, or about 15% trehalose or sucrose, e.g. about 5% sucrose) by weight) and a cyclodextrin such as β-cyclodextrin, in a concentration of about 1% to about 25% by weight (e.g. about 5% to about 20%, e.g. 10% or about 20% by weight, or about 15% to about 20% by weight cyclodextrin). Contemplated formulations may include a plurality of disclosed nanoparticles (e.g. nanoparticles having PLA-PEG and an active agent), and about 2% to about 15 wt % (or about 4% to about 6 wt %, e.g. about 5 wt %) sucrose and about 5 wt % to about 20% (e.g. about 7% wt percent to about 12 wt %, e.g. about 10 wt %) of a cyclodextrin, e.g., HPbCD).

The present disclosure relates in part to lyophilized pharmaceutical compositions that, when reconstituted, have a minimal amount of large aggregates. Such large aggregates may have a size greater than about 0.5 µm, greater than about 1 µm, or greater than about 10 µm, and can be undesirable in a reconstituted solution. Aggregate sizes can be measured using a variety of techniques including those indicated in the U.S. Pharmacopeia at 32 <788>, hereby incorporated by reference. The tests outlined in USP 32 <788> include a light obscuration particle count test, microscopic particle count test, laser diffraction, and single particle optical sensing. In one embodiment, the particle size in a given sample is measured using laser diffraction and/or single particle optical sensing.

The USP 32 <788> by light obscuration particle count test sets forth guidelines for sampling particle sizes in a suspension. For solutions with less than or equal to 100 mL, the preparation complies with the test if the average number of particles present does not exceed 6000 per container that are ≥10 µm and 600 per container that are ≥25 µm.

As outlined in USP 32 <788>, the microscopic particle count test sets forth guidelines for determining particle amounts using a binocular microscope adjusted to 100±10× magnification having an ocular micrometer. An ocular micrometer is a circular diameter graticule that consists of a circle divided into quadrants with black reference circles denoting 10 nm and 25 nm when viewed at 100× magnification. A linear scale is provided below the graticule. The number of particles with reference to 10 µm and 25 µm are visually tallied. For solutions with less than or equal to 100 mL, the preparation complies with the test if the average number of particles present does not exceed 3000 per container that are ≥10 µm and 300 per container that are ≥25 µm.

In some embodiments, a 10 mL aqueous sample of a disclosed composition upon reconstitution comprises less than 600 particles per ml having a size greater than or equal to 10 microns; and/or less than 60 particles per ml having a size greater than or equal to 25 microns.

Dynamic light scattering (DLS) may be used to measure particle size, but it relies on Brownian motion so the technique may not detect some larger particles. Laser diffraction relies on differences in the index of refraction between the particle and the suspension media. The technique is capable of detecting particles at the sub-micron to millimeter range. Relatively small (e.g., about 1-5 weight %) amounts of larger particles can be determined in nanoparticle suspensions. Single particle optical sensing (SPOS) uses light obscuration of dilute suspensions to count individual particles of about 0.5 nm. By knowing the particle concentration of the measured sample, the weight percentage of aggregates or the aggregate concentration (particles/mL) can be calculated.

Formation of aggregates can occur during lyophilization due to the dehydration of the surface of the particles. This dehydration can be avoided by using lyoprotectants, such as disaccharides, in the suspension before lyophilization. Suitable disaccharides include sucrose, lactulose, lactose, maltose, trehalose, or cellobiose, and/or mixtures thereof. Other contemplated disaccharides include kojibiose, nigerose, isomaltose, β,β-trehalose, α,β-trehalose, sophorose, laminaribiose, gentiobiose, turanose, maltulose, palatinose, gentiobiulose, mannobiase, melibiose, melibiulose, rutinose, rutinulose, and xylobiose. Reconstitution shows equivalent DLS size distributions when compared to the starting suspension. However, laser diffraction can detect particles of >10 µm in size in some reconstituted solutions. Further, SPOS also may detect >10 µm sized particles at a concentration above that of the FDA guidelines ($10^4$-$10^5$ particles/mL for >10 µm particles).

In some embodiments, one or more ionic halide salts may be used as an additional lyoprotectant to a sugar, such as sucrose, trehalose or mixtures thereof. Sugars may include disaccharides, monosaccharides, trisaccharides, and/or polysaccharides, and may include other excipients, e.g. glycerol and/or surfactants. Optionally, a cyclodextrin may be included as an additional lyoprotectant. The cyclodextrin may be added in place of the ionic halide salt. Alternatively, the cyclodextrin may be added in addition to the ionic halide salt.

Suitable ionic halide salts may include sodium chloride, calcium chloride, zinc chloride, or mixtures thereof. Additional suitable ionic halide salts include potassium chloride, magnesium chloride, ammonium chloride, sodium bromide, calcium bromide, zinc bromide, potassium bromide, magnesium bromide, ammonium bromide, sodium iodide, calcium iodide, zinc iodide, potassium iodide, magnesium iodide, or ammonium iodide, and/or mixtures thereof. In one embodiment, about 1 to about 15 weight percent sucrose may be used with an ionic halide salt. In one embodiment, the lyophilized pharmaceutical composition may comprise about 10 to about 100 mM sodium chloride. In another embodiment, the lyophilized pharmaceutical composition may comprise about 100 to about 500 mM of divalent ionic chloride salt, such as calcium chloride or zinc chloride. In yet another embodiment, the suspension to be lyophilized may further comprise a cyclodextrin, for example, about 1 to about 25 weight percent of cyclodextrin may be used.

A suitable cyclodextrin may include α-cyclodextrin, β-cyclodextrin, γ-cyclodextrin, or mixtures thereof. Exemplary cyclodextrins contemplated for use in the compositions disclosed herein include hydroxypropyl-β-cyclodextrin (HPbCD), hydroxyethyl-β-cyclodextrin, sulfobutylether-β-cyclodextrin, methyl-β-cyclodextrin, dimethyl-β-cyclodextrin, carboxymethyl-β-cyclodextrin, carboxymethyl ethyl-β-cyclodextrin, diethyl-β-cyclodextrin, tri-O-alkyl-β-cyclodextrin, glocosyl-β-cyclodextrin, and maltosyl-β-cyclodextrin. In one embodiment, about 1 to about 25 weight percent trehalose (e.g. about 10% to about 15%, e.g. 5 to about 20% by weight) may be used with cyclodextrin. In one embodiment, the lyophilized pharmaceutical composition may comprise about 1 to about 25 weight percent β-cyclodextrin. An exemplary composition may comprise nanoparticles comprising PLA-PEG, an active/therapeutic agent, about 4% to about 6% (e.g. about 5% wt percent) sucrose, and about 8 to about 12 weight percent (e.g. about 10 wt. %) HPbCD.

In one aspect, a lyophilized pharmaceutical composition is provided comprising disclosed nanoparticles, wherein upon reconstitution of the lyophilized pharmaceutical composition at a nanoparticle concentration of about 50 mg/mL, in less than or about 100 mL of an aqueous medium, the reconstituted composition suitable for parenteral administration comprises less than 6000, such as less than 3000, microparticles of greater than or equal to 10 microns; and/or less than 600, such as less than 300, microparticles of greater than or equal to 25 microns.

The number of microparticles can be determined by means such as the USP 32 <788> by light obscuration particle count test, the USP 32 <788> by microscopic particle count test, laser diffraction, and single particle optical sensing.

In an aspect, a pharmaceutical composition suitable for parenteral use upon reconstitution is provided comprising a plurality of therapeutic particles each comprising a copolymer having a hydrophobic polymer segment and a hydrophilic polymer segment; an active agent; a sugar; and a cyclodextrin.

For example, the copolymer may be poly(lactic) acid-block-poly(ethylene)glycol copolymer. Upon reconstitution, a 100 mL aqueous sample may comprise less than 6000 particles having a size greater than or equal to 10 microns; and less than 600 particles having a size greater than or equal to 25 microns.

The step of adding a disaccharide and an ionic halide salt may comprise adding about 5 to about 15 weight percent sucrose or about 5 to about 20 weight percent trehalose (e.g., about 10 to about 20 weight percent trehalose), and about 10 to about 500 mM ionic halide salt. The ionic halide salt may be selected from sodium chloride, calcium chloride, and zinc chloride, or mixtures thereof. In an embodiment, about 1 to about 25 weight percent cyclodextrin is also added.

In another embodiment, the step of adding a disaccharide and a cyclodextrin may comprise adding about 5 to about 15 weight percent sucrose or about 5 to about 20 weight percent trehalose (e.g., about 10 to about 20 weight percent trehalose), and about 1 to about 25 weight percent cyclodextrin. In an embodiment, about 10 to about 15 weight percent cyclodextrin is added. The cyclodextrin may be selected from α-cyclodextrin, β-cyclodextrin, γ-cyclodextrin, or mixtures thereof.

In another aspect, a method of preventing substantial aggregation of particles in a pharmaceutical nanoparticle composition is provided comprising adding a sugar and a salt to the lyophilized formulation to prevent aggregation of the nanoparticles upon reconstitution. In an embodiment, a cyclodextrin is also added to the lyophilized formulation. In yet another aspect, a method of preventing substantial aggregation of particles in a pharmaceutical nanoparticle composition is provided comprising adding a sugar and a cyclodextrin to the lyophilized formulation to prevent aggregation of the nanoparticles upon reconstitution. A contemplated lyophilized composition may have a therapeutic particle concentration of greater than about 40 mg/mL. The formulation suitable for parenteral administration may have less than about 600 particles having a size greater than 10 microns in a 10 mL dose. Lyophilizing may comprise freezing the composition at a temperature of greater than about −40° C., or e.g. less than about −30° C., forming a frozen composition; and drying the frozen composition to form the lyophilized composition. The step of drying may occur at about 50 mTorr at a temperature of about −25 to about −34° C., or about −30 to about −34° C.

Methods of Treatment

In some embodiments, targeted nanoparticles may be used to treat, alleviate, ameliorate, relieve, delay onset of, inhibit progression of, reduce severity of, and/or reduce incidence of one or more symptoms or features of a disease, disorder, and/or condition. In some embodiments, targeted nanoparticles may be used to treat solid tumors, e.g., cancer and/or cancer cells. In certain embodiments, targeted nanoparticles may be used to treat any cancer wherein PSMA is expressed on the surface of cancer cells or in the tumor neovasculature in a subject in need thereof, including the neovasculature of prostate or non-prostate solid tumors. Examples of the PSMA-related indication include, but are not limited to, prostate cancer, breast cancer, non-small cell lung cancer, colorectal carcinoma, and glioblastoma.

The term "cancer" includes pre-malignant as well as malignant cancers. Cancers include, but are not limited to, blood (e.g., chronic myelogenous leukemia, chronic myelomonocytic leukemia, Philadelphia chromosome positive acute lymphoblastic leukemia, mantle cell lymphoma), prostate, gastric cancer, colorectal cancer, skin cancer, e.g., melanomas or basal cell carcinomas, lung cancer (e.g., non-small cell lung cancer), breast cancer, cancers of the head and neck, bronchus cancer, pancreatic cancer, urinary bladder cancer, brain or central nervous system cancer, peripheral nervous system cancer, esophageal cancer, cancer of the oral cavity or pharynx, liver cancer (e.g., hepatocellular carcinoma), kidney cancer (e.g., renal cell carcinoma), testicular cancer, biliary tract cancer, small bowel or appendix cancer, gastrointestinal stromal tumor, salivary gland cancer, thyroid gland cancer, adrenal gland cancer, osteosarcoma, chondrosarcoma, cancer of hematological tissues, and the like. "Cancer cells" can be in the form of a tumor (i.e., a solid tumor), exist alone within a subject (e.g., leukemia cells), or be cell lines derived from a cancer.

Cancer can be associated with a variety of physical symptoms. Symptoms of cancer generally depend on the type and location of the tumor. For example, lung cancer can cause coughing, shortness of breath, and chest pain, while colon cancer often causes diarrhea, constipation, and blood in the stool. However, to give but a few examples, the following symptoms are often generally associated with many cancers: fever, chills, night sweats, cough, dyspnea, weight loss, loss of appetite, anorexia, nausea, vomiting, diarrhea, anemia, jaundice, hepatomegaly, hemoptysis, fatigue, malaise, cognitive dysfunction, depression, hormonal disturbances, neutropenia, pain, non-healing sores, enlarged lymph nodes, peripheral neuropathy, and sexual dysfunction.

In one aspect, a method for the treatment of cancer (e.g., leukemia) is provided. In some embodiments, the treatment of cancer comprises administering a therapeutically effective amount of inventive targeted particles to a subject in need thereof, in such amounts and for such time as is necessary to achieve the desired result. In certain embodiments, a "therapeutically effective amount" of an inventive targeted particle is that amount effective for treating, alleviating, ameliorating, relieving, delaying onset of, inhibiting progression of, reducing severity of, and/or reducing incidence of one or more symptoms or features of cancer.

In one aspect, a method for administering inventive compositions to a subject suffering from cancer (e.g., leukemia) is provided. In some embodiments, particles may be administered to a subject in such amounts and for such time as is necessary to achieve the desired result (i.e., treatment of cancer). In certain embodiments, a "therapeutically effective amount" of an inventive targeted particle is that amount effective for treating, alleviating, ameliorating, relieving, delaying onset of, inhibiting progression of, reducing severity of, and/or reducing incidence of one or more symptoms or features of cancer.

Inventive therapeutic protocols involve administering a therapeutically effective amount of an inventive targeted particle to a healthy individual (i.e., a subject who does not display any symptoms of cancer and/or who has not been diagnosed with cancer). For example, healthy individuals may be "immunized" with an inventive targeted particle prior to development of cancer and/or onset of symptoms of cancer; at risk individuals (e.g., patients who have a family history of cancer; patients carrying one or more genetic mutations associated with development of cancer; patients having a genetic polymorphism associated with development of cancer; patients infected by a virus associated with development of cancer; patients with habits and/or lifestyles associated with development of cancer; etc.) can be treated substantially contemporaneously with (e.g., within 48 hours, within 24 hours, or within 12 hours of) the onset of symptoms of cancer. Of course individuals known to have cancer may receive inventive treatment at any time.

In other embodiments, disclosed nanoparticles can be used to inhibit the growth of cancer cells, e.g., myelogenous leukemia cancer cells. As used herein, the term "inhibits growth of cancer cells" or "inhibiting growth of cancer cells" refers to any slowing of the rate of cancer cell proliferation and/or migration, arrest of cancer cell proliferation and/or migration, or killing of cancer cells, such that the rate of cancer cell growth is reduced in comparison with the observed or predicted rate of growth of an untreated control cancer cell. The term "inhibits growth" can also refer to a reduction in size or disappearance of a cancer cell or tumor, as well as to a reduction in its metastatic potential. Preferably, such an inhibition at the cellular level may reduce the size, deter the growth, reduce the aggressiveness, or prevent or inhibit metastasis of a cancer in a patient. Those skilled in the art can readily determine, by any of a variety of suitable indicia, whether cancer cell growth is inhibited.

Inhibition of cancer cell growth may be evidenced, for example, by arrest of cancer cells in a particular phase of the cell cycle, e.g., arrest at the G2/M phase of the cell cycle. Inhibition of cancer cell growth can also be evidenced by direct or indirect measurement of cancer cell or tumor size. In human cancer patients, such measurements generally are made using well known imaging methods such as magnetic resonance imaging, computerized axial tomography and X-rays. Cancer cell growth can also be determined indirectly, such as by determining the levels of circulating carcinoembryonic antigen, prostate specific antigen or other cancer-specific antigens that are correlated with cancer cell growth. Inhibition of cancer growth is also generally correlated with prolonged survival and/or increased health and well-being of the subject.

Also provided herein are methods of administering to a patient a nanoparticle disclosed herein including an active agent, wherein, upon administration to a patient, such nanoparticles substantially reduces the volume of distribution and/or substantially reduces free $C_{max}$, as compared to administration of the agent alone (i.e., not as a disclosed nanoparticle).

U.S. Pat. No. 8,206,747, issued Jun. 26, 2012, entitled "Drug Loaded Polymeric Nanoparticles and Methods of Making and Using Same" is hereby incorporated by reference in its entirety.

EXAMPLES

The invention now being generally described, it will be more readily understood by reference to the following examples which are included merely for purposes of illustration of certain aspects and embodiments, and are not intended to limit the invention in any way.

Example 1: Preparation of Sunitinib-Containing Nanoparticles

Preparation of organic phase. (Step 1, preparation of polymer solution) To a first 7 mL glass vial are added poly(lactic acid)-poly(ethylene glycol) diblock copolymer (PLA-PEG) and ethyl acetate. The mixture is vortexed until the polymer is dissolved. (Step 2, preparation of drug solution) An appropriate amount of benzyl alcohol is added to a second 7 mL glass vial containing sunitinib, and the mixture is vortexed until the sunitinib is dissolved. Alternatively, an appropriate amount of oleic acid is added to benzyl alcohol to make a 3-15% (w/w) solution, which is then added to a second 7 mL glass vial containing sunitinib and the mixture vortexed until the sunitinib is dissolved. (Step 3) The polymer solution and drug solution are combined and vortexed for a few minutes prior to formulation of the nanoparticles.

Preparation of aqueous phase. (For a 0.07% sodium cholate solution) To a 1 L bottle are added sodium cholate (SC) (0.7 g) and DI water (959.3 g). The mixture is stirred on a stir plate until dissolved. To the sodium cholate/water was added benzyl alcohol (40 g) and the mixture stirred on a stir plate until dissolved. (For a 0.25% sodium cholate solution) To a 1 L bottle are added sodium cholate (SC) (2.5 g) and DI water (957.5 g). The mixture is stirred on a stir plate until dissolved. To the sodium cholate/water was added benzyl alcohol (40 g) and the mixture stirred on a stir plate until dissolved.

Formation of emulsion. The ratio of aqueous phase to organic phase is 5:1. The organic phase is poured into the aqueous phase and the mixture homogenized using a hand homogenizer for 10 seconds at room temperature to form a course emulsion. The course emulsion is fed through a high pressure homogenizer (110S) with pressure set at 40-45 psi on gauge for 1 discreet pass to form a nanoemulsion (fine emulsion).

Formation of nanoparticles. The nanoemulsion is poured into a quench (D.I. water) at less than 5° C. while stirring on stir plate to form a quenched phase. The ratio of quench to emulsion is 8:1. To the quenched phase is added Tween 80 in water (35% (w/w)) at a ratio of 150:1 Tween 80 to drug.

Concentration of nanoparticles through tangential flow filtration (TFF). The quenched phase is concentrated using TFF with 300 kDa Pall cassette (2 membrane) to form a nanoparticle concentrate of ~100 mL. The nanoparticle concentrate is diafiltered with ~20 diavolumes (2 L) of cold DI water. The volume of the diafiltered nanoparticle concentrate is reduced to a minimal volume. Cold water (100 mL) is added to the vessel and pumped through the membrane to rinse and form a slurry. The slurry (100-180 mL) is collected in a glass vial. The slurry is further concentrated using a smaller TFF apparatus to a final volume of 10-20 mL of final slurry.

Determination of solids concentration of unfiltered final slurry. To a tared 20 mL scintillation vial is added a volume of final slurry, which is dried under vacuum on a lyophilizer/oven. The weight of nanoparticles in the volume of dried slurry is determined. To the final slurry is added concentrated sucrose (0.666 g/g) to attain 10% sucrose.

Determination of solids concentration of 0.45 μm filtered final slurry. A portion of the final slurry sample is filtered through a 0.45 μm syringe filter before addition of sucrose. To a tared 20 mL scintillation vial is added a volume of filtered sample, which is dried under vacuum using a lyophilizer/oven. The remaining sample of unfiltered final slurry with sucrose is frozen.

Eleven sunitinib formulations were made, with or without oleic acid doping. The theoretical loading, solids concentration, observed loading, and particle size for formulations made without oleic acid doping are listed in Table 1:

TABLE 1

Sunitinib formulations without oleic acid.

| Lot # | Description | Sunitinib Theoretical Loading | Solids Concentration | Loading % | size (nm) |
|---|---|---|---|---|---|
| 140-10-1 | 16/5 PLA/PEG, 7.5% water in BA | 35% | 6% | 2.78 | 136.20 |
| 140-10-2 | 16/5 PLA/PEG, 7.5% water in BA | 35% | 6% | 2.91 | 120.70 |
| 140-10-3 | 16/5 PLA/PEG, no water, 100% BA | 35% | 6% | 1.63 | 151.60 |
| 140-10-4 | 16/5 PLA/PEG, no water, 100% BA | 35% | 6% | 2.60 | 111.10 |

As can be seen from Table 1, in the case of 16/5 PLA/PEG formulation with or without water (plain 16/5 PLA/PEG), drug loading within nanoparticles was less than 3%. The oleic acid concentration used to dissolve sunitinib, theoretical loading, solid concentration, observed loading, and particle size for formulations made with oleic acid doping are listed in Table 2:

TABLE 2

Sunitinib formulations with oleic acid.

| Lot # | Description | Oleic Acid Concentration (% in BA) | Sunitinib Theoretical Loading | Solids Concentration | Loading % | size (nm) |
|---|---|---|---|---|---|---|
| 140-60-1 | 16/5 PLA/PEG | 3 | 40% | 4.7% | 5.01 | 86.6 |
| 140-20-1 | 16/5 PLA/PEG | 6 | 40% | 4.7% | 5.87 | 119.1 |
| 140-20-2 | 16/5 PLA/PEG | 9 | 40% | 4.7% | 8.81 | 120.4 |
| 140-30-2 | 16/5 PLA/PEG | 9 | 40% | 4.7% | 9.52 | 122.4 |
| 140-20-3 | 16/5 PLA/PEG | 12 | 40% | 4.7% | 8.06 | 138.8 |
| 140-30-3 | 16/5 PLA/PEG | 12 | 40% | 4.7% | 10.36 | 134.6 |
| 140-30-1 | 16/5 PLA/PEG | 15 | 40% | 4.7% | 9.47 | 119.8 |

As can be seen from Table 2, when oleic acid was added to sunitinib in organic solvent, sunitinib loading in the nanoparticles increased significantly up to over 10%, depending on the concentration of oleic acid used in the formulation. As compared to formulations made without oleic acid, which had a drug loading of less than 3% (see Table 1), the increase in drug loading observed for formulations containing oleic acid was significant.

Figure 3:
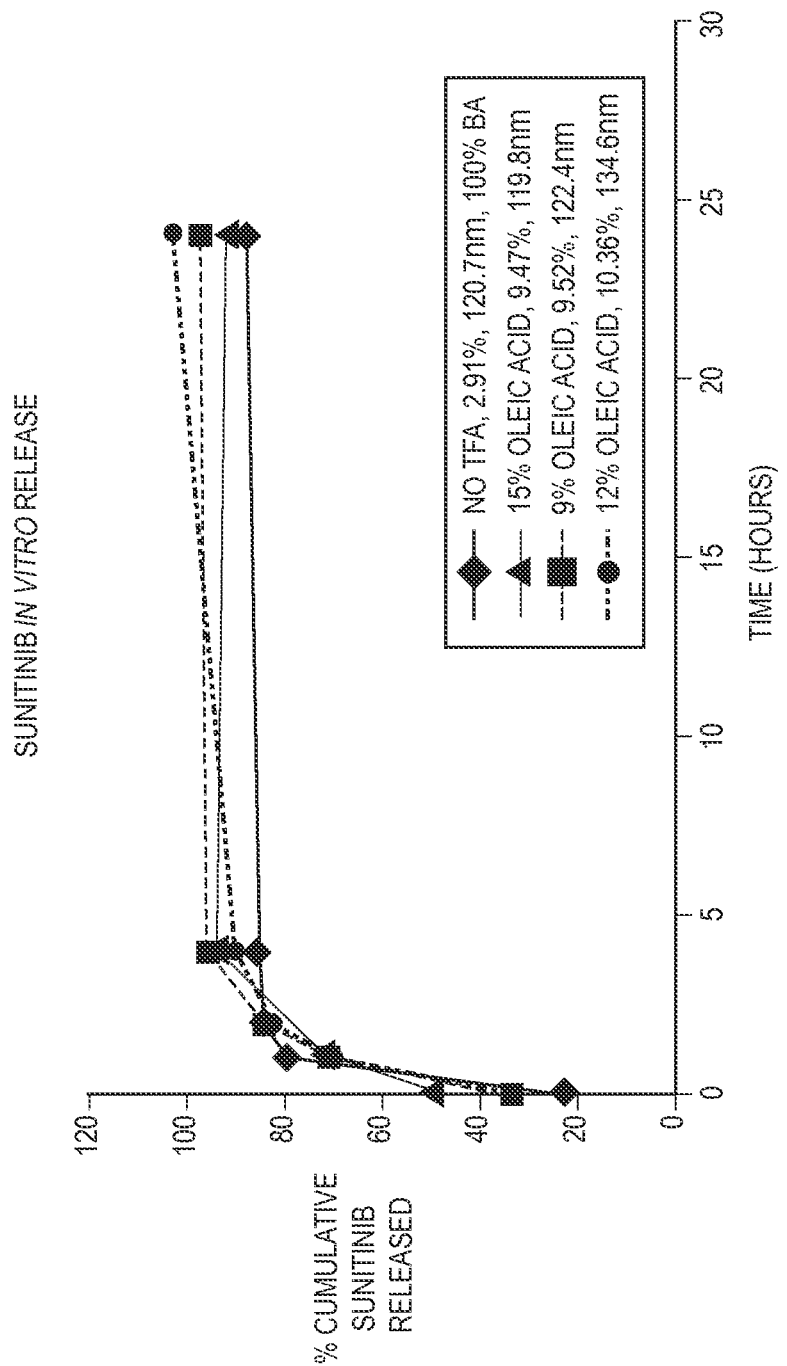
FIG. 3 depicts in vitro release profiles for sunitinib-containing nanoparticle formulations.

FIG. 3 shows in vitro release profiles for sunitinib-containing nanoparticles, with or without oleic acid doping. Nanoparticles with oleic acid doping showed similar release profiles to that of sunitinib nanoparticles made without oleic acid. Thus, at a particular solid concentration, oleic acid does not significantly impact the release profile of sunitinib nanoparticles relative to formulations made without oleic acid.

Example 2: Preparation of Imatinib-Containing Nanoparticles

Preparation of organic phase. (Step 1, preparation of polymer solution) To a first 7 mL glass vial are added poly(lactic acid)-poly(ethylene glycol) diblock copolymer (PLA-PEG) and ethyl acetate. The mixture is vortexed until the polymer is dissolved. (Step 2, preparation of drug solution) An appropriate amount of benzyl alcohol is added to a second 7 mL glass vial containing imatinib, and the mixture is vortexed until the imatinib is dissolved. Alternatively, an appropriate amount of oleic acid is added to benzyl alcohol to make a 9% (w/w) solution, which is then added to a second 7 mL glass vial containing imatinib and the mixture vortexed until the imatinib is dissolved. (Step 3) The polymer solution and drug solution are combined and vortexed for about 10-30 seconds prior to formulation of the nanoparticles.

Preparation of aqueous phase. A 0.05-0.5% sodium cholate/4% benzyl alcohol solution in water (w/w) is prepared by dissolving sodium cholate in DI water and then dissolving benzyl alcohol in the aqueous sodium cholate solution.

Formation of emulsion. The ratio of aqueous phase to organic phase is 5:1. The organic phase is poured into the aqueous phase and the mixture homogenized using a hand homogenizer for 5-10 seconds at room temperature to form a course emulsion. The course emulsion is fed through a high pressure homogenizer (M-110S) with pressure set at 44-50 psi on gauge for 1 discreet pass to form a nanoemulsion (fine emulsion).

Formation of nanoparticles. The nanoemulsion is poured into a quench (D.I. water) at less than 5° C. while stirring on stir plate to form a quenched phase. The ratio of quench to emulsion is 10:1. To the quenched phase is added Tween 80 in water (35% (w/w)) at a ratio of 150:1 Tween 80 to drug for oleic acid-containing formulation and at a ratio of 50:1 Tween 80 to drug for formulations without oleic acid.

Concentration of nanoparticles through tangential flow filtration (TFF). The quenched phase is concentrated using TFF with 300 kDa Pall cassette (2 membrane) to form a nanoparticle concentrate of ~200 mL. The nanoparticle concentrate is diafiltered with ~20 diavolumes (4 L) of cold DI water (less than 5° C.). The volume of the diafiltered nanoparticle concentrate is reduced to a minimal volume. Cold water (30-75 mL) is added to the vessel and pumped through the membrane to rinse and form a final slurry. The final slurry (50-100 mL) is collected in a glass vial.

To the final slurry is added concentrated sucrose (0.666 g/g) to attain 10% sucrose, which is then frozen and stored at −20° C.

Eleven imatinib formulations were made, with or without oleic acid doping. The theoretical loading, solids concentration, observed loading, particle size, concentration of sodium cholate (SC), number of homogenizer passes and corresponding pressure for formulations made without oleic acid doping are listed in Table 3:

TABLE 3

Imatinib formulations without oleic acid.

| Lot # | Description | Imatinib Theoretical Loading | Solids Concentration | Loading % | size (nm) | % SC, pass# @ psi# |
|---|---|---|---|---|---|---|
| 168-29-1 | 16/5 PLA/PEG | 30% | 4.7% | 1.0 | 134 | 0.2% SC, 2@50 psi |
| 168-29-2 | 16/5 PLA/PEG | 30% | 4.7% | 0.4 | 106 | 0.5% SC, 2@44 psi |
| 168-49-1 | 16/5 PLA/PEG | 30% | 4.7% | 0.43 | 120 | 0.35% SC, 1@50 psi |
| 168-81-2 | 16/5 PLA/PEG | 30% | 15% | 6.8 | 110 | 0.25% SC, 1@50 psi |
| 168-103-1 | 16/5 PLA/PEG | 30% | 15% | 8.1 | 108 | 0.25% SC, 1@50 psi |

As can be seen from Table 3, the formulations prepared without oleic acid at 4.7% and 15% solids resulted in a drug loading of about 0.4-1% and about 7-8% respectively. Increased solids concentration resulted in increased drug load.

The theoretical loading, solids concentration, observed loading, particle size, concentration of sodium cholate (SC), number of homogenizer passes and corresponding pressure for formulations made with oleic acid doping are listed in Table 4:

TABLE 4

Imatinib formulations with oleic acid.

| Lot # | Description | Oleic Acid Concentration (% in BA) | Imatinib Theoretical Loading | Solids Concentration | Loading % | size (nm) | % SC, pass# @ psi# |
|---|---|---|---|---|---|---|---|
| 168-29-5 | 16/5 PLA-PEG, 2:1 molar ratio oleic acid:drug | 9 | 30% | 4.7% | 8.2 | 118 | 0.1% SC, 1@50 psi |
| 168-29-6 | 16/5 PLA-PEG, 2:1 molar ratio oleic acid:drug | 9 | 30% | 4.7% | 7.8 | 116 | 0.1% SC, 1@50 psi |
| 168-103-6 | 16/5 PLA-PEG, 1.1:1 molar ratio oleic acid:drug | 9 | 30% | 9.0% | 6.4 | 120 | 0.05% SC, 1@50 psi |
| 168-103-7 | 16/5 PLA-PEG, 1.1:1 molar ratio oleic acid:drug | 9 | 30% | 9.0% | 8.2 | 121 | 0.05% SC, 1@50 psi |
| 168-49-3 | 16/5 PLA-PEG, 0.6:1 molar ratio oleic acid:drug | 9 | 30% | 15.0% | 8.07 | 102 | 0.1% SC, 1@50 psi |
| 168-103-5 | 16/5 PLA-PEG, 0.6:1 molar ratio oleic acid:drug | 9 | 30% | 15.0% | 8.9 | 108 | 0.05% SC, 1@50 psi |

As can be seen from Table 4, formulations prepared with oleic acid resulted in drug loads of about 6-9% at all tested solids concentrations and molar ratios of oleic acid to drug.

Figure 4:
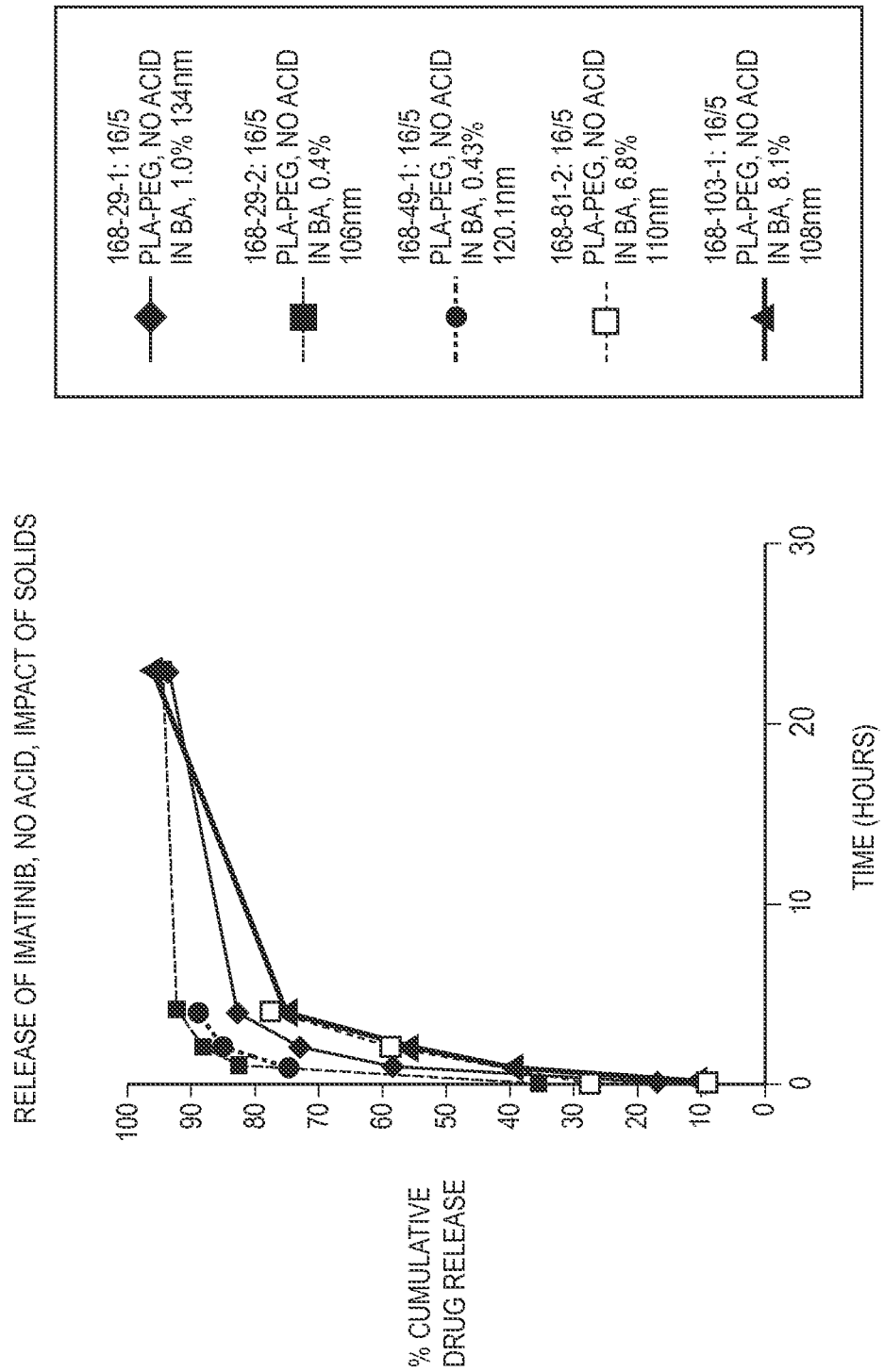
FIG. 4 depicts in vitro release profiles for imatinib-containing nanoparticle formulations.

FIG. 4 shows in vitro release profiles for imatinib-containing nanoparticles having different solids concentration and without oleic acid doping. The in vitro release is slower at higher solids concentration (solid lines on graph), while larger particle size at lower solids (dotted lines on graph) also slows down release.

Figure 5:
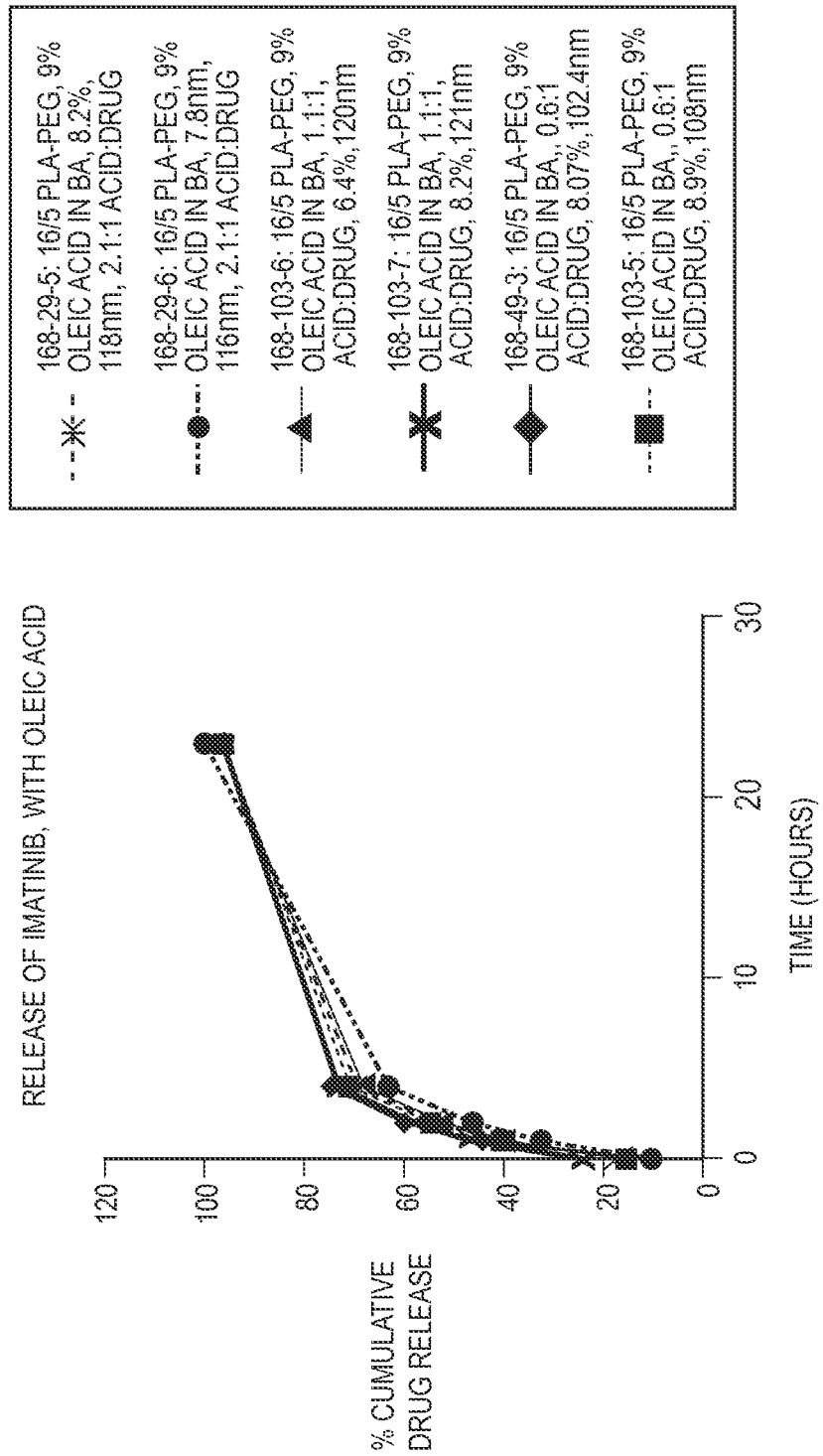
FIG. 5 depicts in vitro release profiles for imatinib-containing nanoparticle formulations.

FIG. 5 shows in vitro release profiles for imatinib formulations prepared with oleic acid. The in vitro release profiles are similar and range from about 68-75% drug released by 4 hours.

Figure 6:
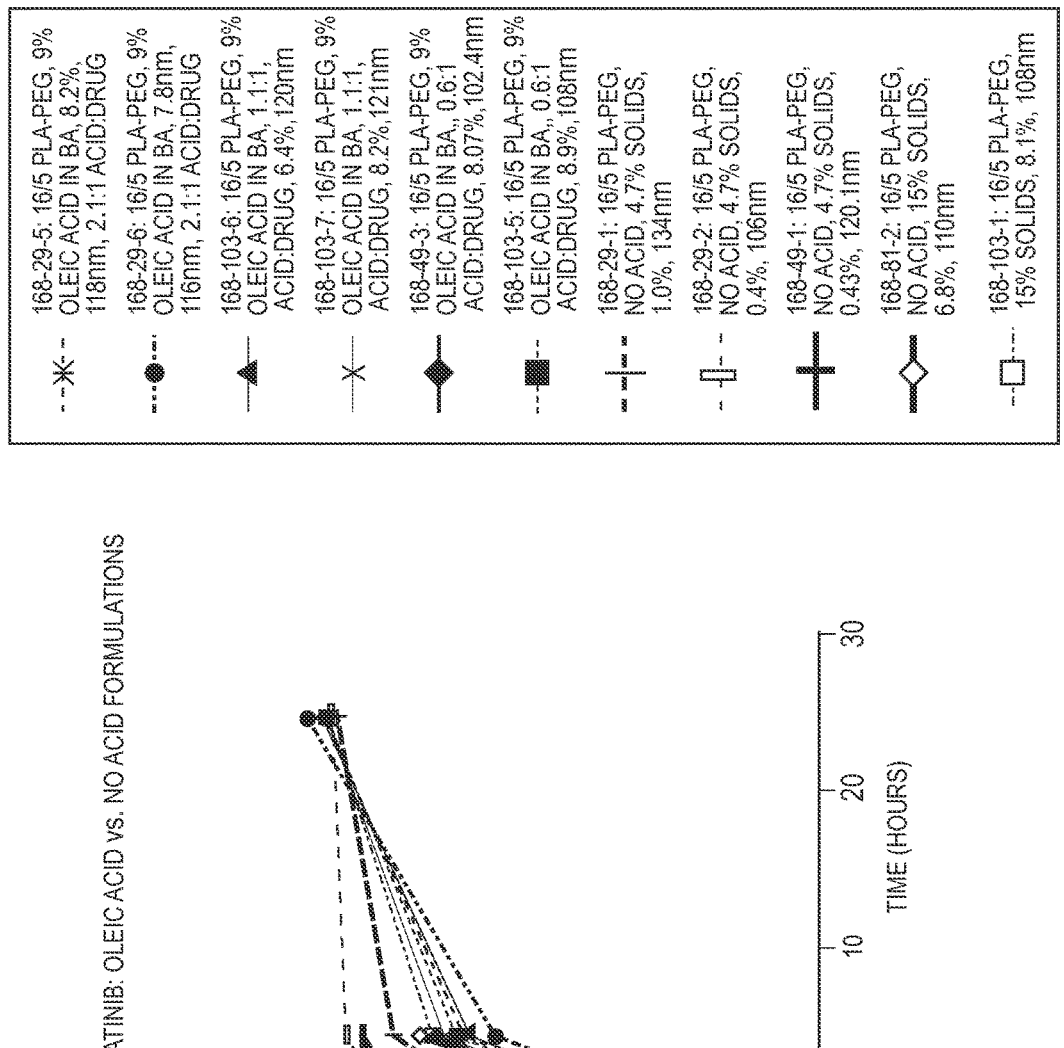
FIG. 6 depicts in vitro release profiles for imatinib-containing nanoparticle formulations.

As shown in FIG. 6, when the release profiles for formulations without acid are compared to the release profiles for formulations with oleic acid, it is observed that the release profiles for the formulations containing higher solids concentration (e.g., 15% solids) and without acid are similar. However, at lower solids concentrations (e.g., 4.7%), formulations with oleic acid show slower release profiles as compared to formulations without oleic acid. Thus, inclusion of oleic acid in a formulation can impact the release profile of the formulation as compared to formulations without oleic acid at a given solids concentration.

Example 3: Preparation of Dasatinib-Containing Nanoparticles—Emulsion Process 1

Preparation of organic phase. To a 20 mL glass vial are added poly(lactic acid)-poly(ethylene glycol) diblock copolymer (PLA-PEG) (950 mg) and benzyl alcohol (9 g). The mixture is vortexed overnight to give a polymer-BA solution. Prior to formulation of the nanoparticles, 50 mg of dasatinib are added to the polymer-BA solution and the mixture vortexed until the dasatinib is dissolved.

Preparation of aqueous phase. To a 1 L bottle are added sodium cholate (SC) (4.75 g) and DI water (955.25 g). The mixture is stirred on a stir plate until dissolved. To the sodium cholate/water was added benzyl alcohol (40 g) and the mixture stirred on a stir plate until dissolved.

Formation of emulsion. The ratio of aqueous phase to organic phase is 5:1. The organic phase is poured into the aqueous phase and the mixture homogenized using a hand homogenizer for 10 seconds at room temperature to form a course emulsion. The course emulsion is fed through a high pressure homogenizer (110S) with pressure set at 46 psi on gauge for 2 discrete passes to form a nanoemulsion (fine emulsion). (Note: after the first pass, 5% SC was doped to the fine emulsion to achieve a final SC concentration of 0.5%.)

Formation of nanoparticles. The nanoemulsion is poured into a quench (D.I. water) at less than 5° C. while stirring on stir plate to form a quenched phase. The ratio of quench to emulsion is 10:1. To the quenched phase is added Tween 80 in water (35% (w/w)) at a ratio of 100:1 Tween 80 to drug.

Concentration of nanoparticles through tangential flow filtration (TFF). The quenched phase is concentrated using TFF with 300 kDa Pall cassette (2 membrane) to form a nanoparticle concentrate of ~200 mL. The nanoparticle concentrate is diafiltered with ~20 diavolumes (4 L) of cold DI water. The volume of the diafiltered nanoparticle concentrate is reduced to a minimal volume. Cold water (100 mL) is added to the vessel and pumped through the membrane to rinse and form a slurry. The final slurry (~100 mL) is collected in a glass vial.

Determination of solids concentration of unfiltered final slurry. To a tared 20 mL scintillation vial is added a volume of final slurry, which is dried under vacuum on a lyophilizer/oven. The weight of nanoparticles in the volume of dried slurry is determined. To the final slurry is added concentrated sucrose (0.666 g/g) to attain 10% sucrose.

Determination of solids concentration of 0.45 μm filtered final slurry. A portion of the final slurry sample is filtered through a 0.45 μm syringe filter before addition of sucrose. To a tared 20 mL scintillation vial is added a volume of filtered sample, which is dried under vacuum using a lyophilizer/oven. The remaining sample of unfiltered final slurry with sucrose is frozen.

Example 4: Preparation of Dasatinib-Containing Nanoparticles—Emulsion Process 2

Preparation of organic phase. To a first 20 mL glass vial are added poly(lactic acid)-poly(ethylene glycol) diblock copolymer (PLA-PEG) (890 mg) and ethyl acetate (16.22 g). The mixture is vortexed overnight to give a polymer-EA solution. To a second 20 mL glass vial are added 110 mg of dasatinib and 4.06 g of freshly prepared 9% oleic acid in benzyl alcohol (BA) and the mixture vortexed overnight to give a drug-acid-BA solution. Prior to formulation of the nanoparticles, polymer-EA solution is added to the drug-acid-BA solution and the mixture vortexed to form the organic phase.

Preparation of aqueous phase. To a 1 L bottle are added sodium cholate (SC) (1.2 g) and DI water (955 g). The mixture is stirred on a stir plate until dissolved. To the sodium cholate/water was added benzyl alcohol (40 g) and the mixture stirred on a stir plate until dissolved.

Formation of emulsion. The ratio of aqueous phase to organic phase is 5:1. The organic phase is poured into the aqueous phase and the mixture homogenized using a hand homogenizer for 10 seconds at room temperature to form a course emulsion. The course emulsion is fed through a high pressure homogenizer (110S) with pressure set at 46 psi on gauge for 1 pass to form a nanoemulsion (fine emulsion).

Formation of nanoparticles. The nanoemulsion is poured into a quench (D.I. water) at less than 5° C. while stirring on stir plate to form a quenched phase. The ratio of quench to emulsion is 10:1. To the quenched phase is added Tween 80 in water (35% (w/w)) at a ratio of 100:1 Tween 80 to drug.

Concentration of nanoparticles through tangential flow filtration (TFF). The quenched phase is concentrated using TFF with 300 kDa Pall cassette (2 membrane) to form a nanoparticle concentrate of ~200 mL. The nanoparticle concentrate is diafiltered with ~20 diavolumes (4 L) of cold DI water. The volume of the diafiltered nanoparticle concentrate is reduced to a minimal volume. Cold water (100 mL) is added to the vessel and pumped through the membrane to rinse and form a slurry. The final slurry (~100 mL) is collected in a glass vial.

Determination of solids concentration of unfiltered final slurry. To a tared 20 mL scintillation vial is added a volume of final slurry, which is dried under vacuum on a lyophilizer/oven. The weight of nanoparticles in the volume of dried slurry is determined. To the final slurry is added concentrated sucrose (0.666 g/g) to attain 10% sucrose.

Determination of solids concentration of 0.45 μm filtered final slurry. A portion of the final slurry sample is filtered through a 0.45 μm syringe filter before addition of sucrose. To a tared 20 mL scintillation vial is added a volume of filtered sample, which is dried under vacuum using a lyophilizer/oven. The remaining sample of unfiltered final slurry with sucrose is frozen.

Example 5: Solubility of Dasatinib in Oleic Acid/Benzyl Alcohol Solutions

As shown in Table 5, the solubility of dasatinib can improved by about 2-3 fold when benzyl alcohol is doped with oleic acid. The solubility of dasatinib in benzyl alcohol, ethyl acetate, and mixtures of oleic acid and benzyl alcohol were quantified using HPLC.

TABLE 5

| Dasatinib solubility in selected solvents with or without oleic acid doping. | |
|---|---|
| Solvents with or without acid doping | Dasatinib solubility (mg/mL, by HPLC) |
| BA | 9.45 |
| EA | 0.32 |
| 3% Oleic Acid in BA | 16.82 |
| 6% Oleic Acid in BA | 25.18 |
| 9% Oleic Acid in BA | 29.84 |

Example 6: Dasatinib-Containing Nanoparticle Formulations Doped with Oleic Acid

Eleven dasatinib formulations were made, with or without oleic acid doping. The formulation conditions and characterization are provided in Table 6. Dasatinib formulations were made as plain nanoparticles without oleic acid doping or nanoparticles doped with oleic acid. Two solids concentrations of 4.7% and 10% were used. The plain formulation (lot 170-51-1) used BA only as organic solvent, while all oleic acid formulations used 20/80 BA/EA (w/w) mixture as organic solvent. EA was added to pre-dissolved drug solution in oleic acid-BA mixture right before emulsification.

TABLE 6

Formulation Conditions and Characterization.

| Lot # | Oleic acid Wt. % in BA | Oleic acid Molar ratio of acid/drug | Dasatinib Theo. Loading | Solid Conc. | Load-ing % | size (nm) | % SC, pass# @ psi# | NP Solids (mg/mL) |
|---|---|---|---|---|---|---|---|---|
| 170-51-1 | | NA | 5% | 10% | 0.87% | 113.3 | 0.475% SC, 1@46 psi, doped with 0.35 g 5% SC to ~0.50%, 1@46 psi | 5.43 |
| 170-100-1 | 3% | 3.48 | 6% | 4.70% | 0.20% | 127.8 | 0.10% SC, 1@46 psi | 7.08 |
| 170-65-3 | 6% | 5.706 | 7.6% | 4.58% | 0.54% | 113.6 | 0.125% SC, 1@45 psi | 6.57 |
| 170-100-2 | | 4.622 | 4% | 10% | 0.58% | 108.7 | 0.12% SC, 1@46 psi | 6.48 |
| 170-139-7 | | 4.608 | 4% | 10% | 0.61% | 111.1 | 0.10% SC, 1@46 psi | 6.20 |
| 170-100-3 | | 4.686 | 9% | 4.7% | 1.17% | 130.5 | 0.12% SC, 2@46 psi | 6.51 |
| 170-139-8 | | 4.668 | 9% | 4.7% | 1.26% | 116.5 | 0.12% SC, 2@46 psi | 6.30 |
| 170-100-4 | 9% | 5.565 | 5% | 10% | 1.90% | 111.3 | 0.12% SC, 1@46 psi | 5.56 |
| 170-139-9 | | 5.560 | 5% | 10% | 1.43% | 109.8 | 0.12% SC, 1@46 psi | 6.01 |
| 170-100-5 | | 5.74 | 11% | 4.7% | 1.99% | 115.5 | 0.12% SC, 1@46 psi | 7.25 |
| 170-139-10 | | 5.732 | 11% | 4.7% | 1.91% | 109.6 | 0.12% SC, 1@46 psi | 6.68 |

As shown in Table 6, particle sizes of all formulations were well controlled within the range of 100-130 nm. Under similar conditions with the goal of achieving similar particle sizes, lots using oleic acid-BA as organic solvent tended to use much less sodium cholate than lots without oleic acid. Without wishing to be bound by any theory, this result may be due to a partial surfactant effect of fatty acids (e.g., oleic acid), which could help stabilize emulsion. 3% oleic acid gave 0.20% drug loading, which was not improved compared to 0.87% for the control lot (formulation without oleic acid). However, when using 6% oleic acid, >1% drug loading was achieved with 4.7% solids and 9% theoretical drug loading. When the oleic acid concentration was increased to 9% in BA, drug loading was increased to ~2%, which is about two times loading of the control lot.

Figure 7:
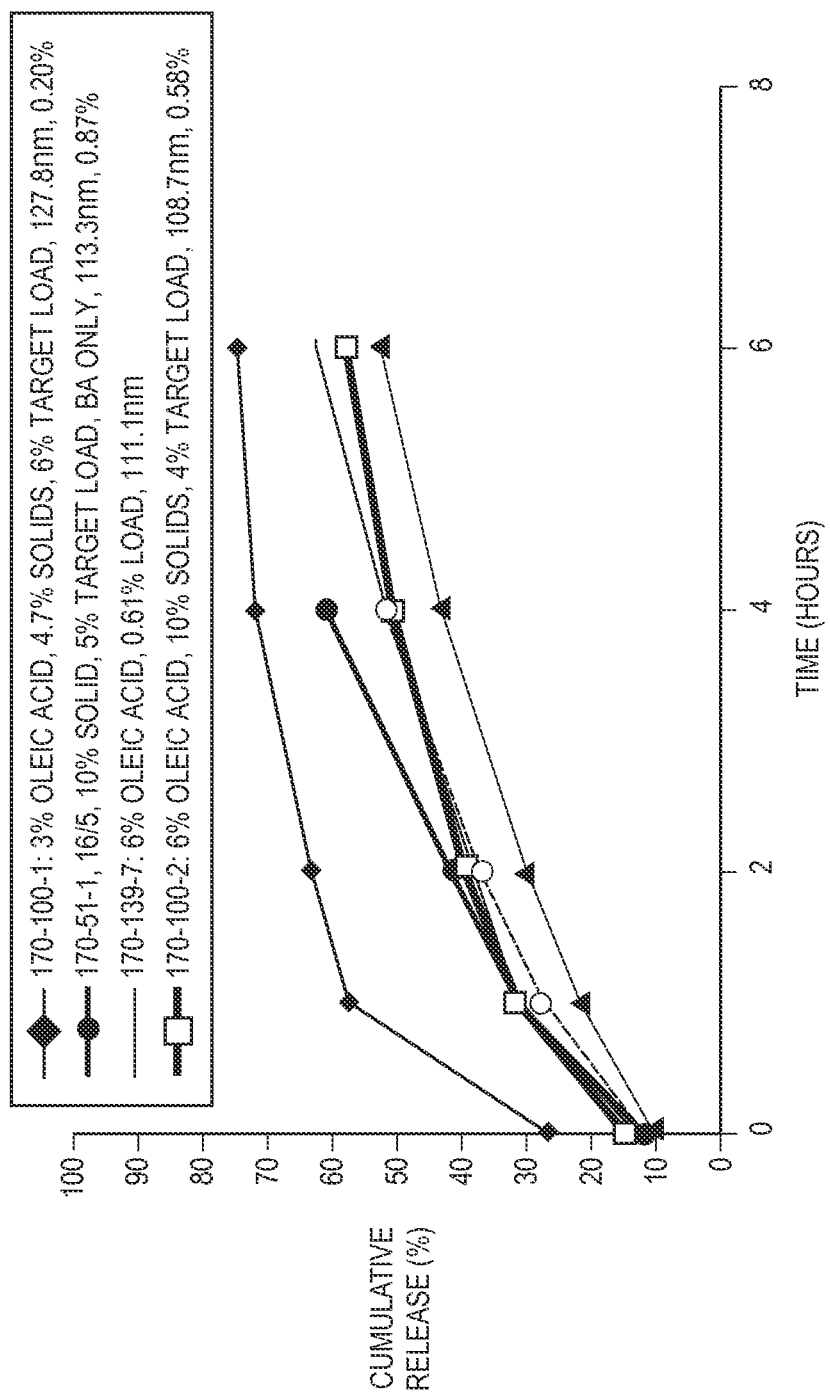
FIG. 7 depicts in vitro release profiles for dasatinib-containing nanoparticle formulations.
Figure 8:
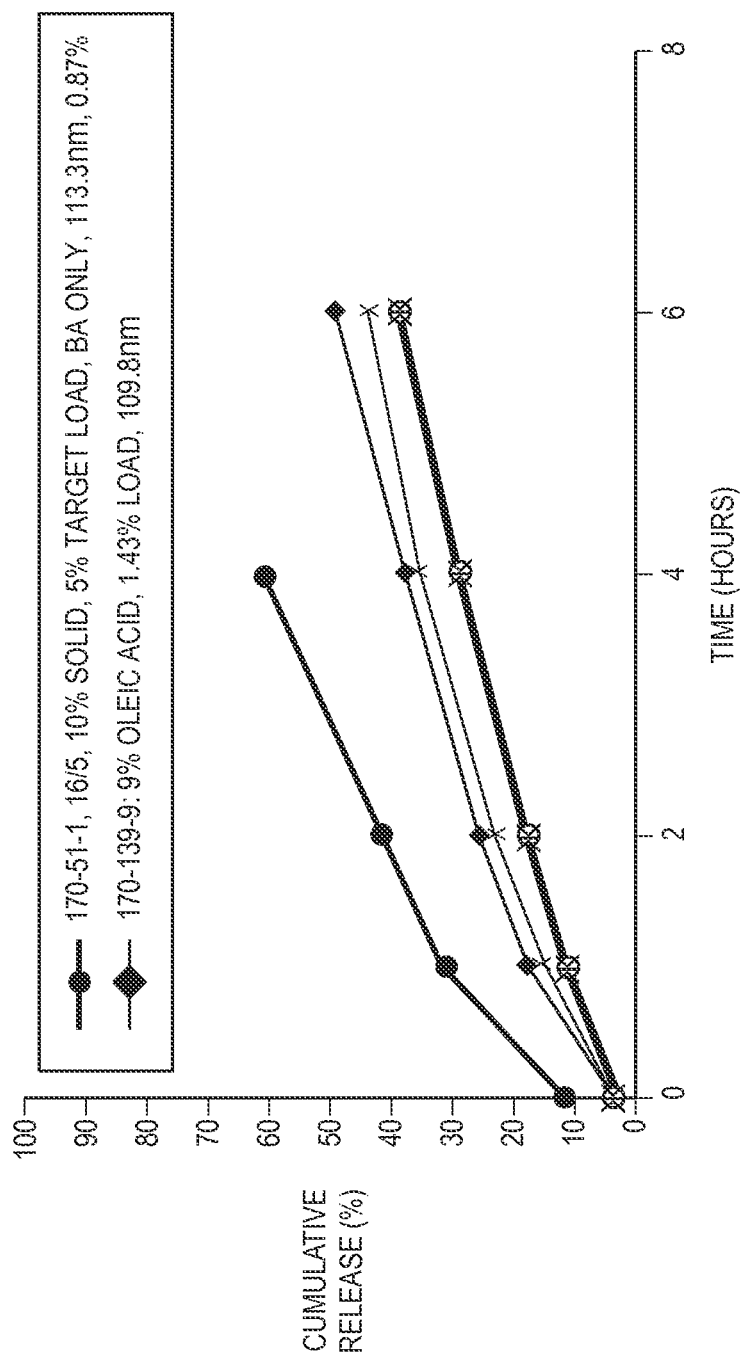
FIG. 8 depicts in vitro release profiles for dasatinib-containing nanoparticle formulations.

In vitro release profiles were shown in following FIGS. 7 and 8. (Because dasatinib degraded after 24 hours in release buffer at 37° C., only up to 6 hours of release data were reported.) As shown in FIG. 7, the 3% oleic acid lot gave the highest burst and fastest release as compared to control nanoparticles formulated without oleic acid and nanoparticles formulated with 6% oleic acid. The 6% oleic acid lots gave bursts of ~10%, which is similar to the burst of the control nanoparticles. Two lots with the highest drug loadings, lots 170-100-3 and 170-139-8, gave relatively slower release than the control lot, with 4 hr cumulative releases of 34.2% and 43.5%, respectively, versus 60.99% for the control lot.

As shown in FIG. 8, when using 9% oleic acid, burst was greatly suppressed down to <5%, and the release rate was also slowed. Drug release at 4 hrs was in the range of about 29% to about 38%, which is slightly slower than the two slow-release lots of 6% oleic acid, lots 170-100-3 and 170-139-8.

The above formulations demonstrate the ability of 9% oleic acid in BA both to improve drug loading and slow the rate of drug release.

Example 7: Dasatinib-Containing Nanoparticle Formulations Doped with Cholic Acids Nine dasatinib formulations doped with cholic acids were made. The formulation conditions and characterization are provided in Table 7. Two solids concentrations of 2.0 and 3.0% were used. The acid/drug molar ration was varied in the formulations.

TABLE 7

Formulation Conditions and Characterization.

| Lot # | Acid % in BA | Acid Molar ratio of acid/drug (feed) | Acid/drug molar ratio in NPs | Dasatinib Theo. Loading | Solid Conc. | Load-ing % | size (nm) | % SC, pass# @ psi# | NP Solids (mg/mL) |
|---|---|---|---|---|---|---|---|---|---|
| 145-54-1 | 12% cholic acid | 3.09 | 2.30 | 30% | 3.0% | 2.1% | 168.6 | 0.05% SC, 1@46 psi | 2.37 |
| 145-54-1R | | | 2.04 | 30% | 3.0% | 2.0% | 144.2 | 0.075% SC, 1@46 psi | 2.56 |
| 145-107-1 | | | 1.50 | 30% | 3.0% | 2.3% | 132.2 | 0.1% SC, 1@46 psi | 2.50 |
| 145-54-2 | 6% deoxycholic acid | 3.65 | 3.50 | 30% | 2.0% | 1.7% | 124.6 | 0.075% SC, 1@46 psi | 2.41 |
| 145-54-2R | | | 3.32 | 30% | 2.0% | 1.9% | 130 | 0.075% SC, 1@46 psi | 2.89 |
| 145-107-2 | | | 2.13 | 30% | 2.0% | 1.8% | 125.7 | 0.08% SC, 1@46 psi | 2.33 |
| 145-54-3 | 3% lithocholic | 1.91 | 2.35 | 30% | 2.0% | 3.5% | 149.9 | 0.05% SC, 1@46 psi | 2.41 |

TABLE 7-continued

Formulation Conditions and Characterization.

| Lot # | % in BA | Acid Molar ratio of acid/drug (feed) | Acid/drug molar ratio in NPs | Dasatinib Theo. Loading | Solid Conc. | Loading % | size (nm) | % SC, pass# @ psi# | NP Solids (mg/mL) |
|---|---|---|---|---|---|---|---|---|---|
| 145-54-3R | acid | | 2.28 | 30% | 2.0% | 2.1% | 124.8 | 0.075% SC, 1@46 psi | 2.82 |
| 145-107-3 | | | 1.51 | 30% | 2.0% | 2.2% | 130.5 | 0.08% SC, 1@46 psi | 2.64 |

As shown in Table 7, particle sizes of the formulations were generally well controlled within the range of 120-150 nm. Similar nanoparticle properties were obtained using each of the three cholic acids; however, use of the lithocholic acid derivative instead of cholic acid allowed four times less acid to be used obtaining similar nanoparticle properties. When using 6% deoxycholic acid, well controlled particle sizes and drug loadings were obtained under a variety of conditions.

Figure 9:
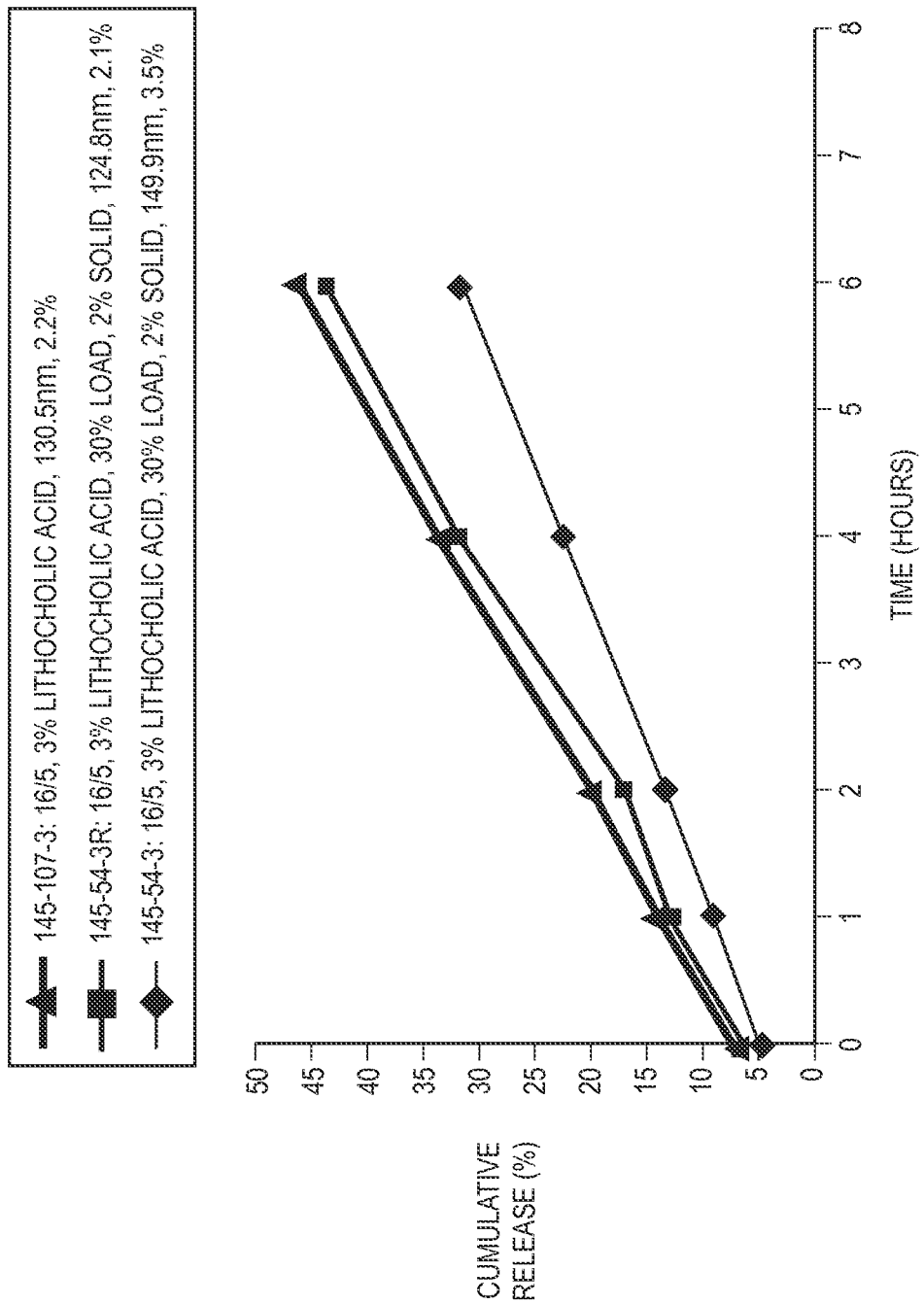
FIG. 9 depicts in vitro release profiles for dasatinib-containing nanoparticle formulations.

In vitro release profiles are shown in Table 8 and FIG. 9. (Because dasatinib degraded after 24 hours in release buffer at 37° C., only up to 6 hours of release data were reported.) As shown in Table 8 and FIG. 9, when using 3% lithocholic acid, burst was <7%, and the release rate was well-controlled. Drug release at 4 hrs was in the range of about 22% to about 34%. The 145-54-3 formulation, using the highest amount of sodium cholate in the aqueous phase, yielded the least amount of burst release (<5%). The 145-54-3R and 145-107-3 formulations had slightly higher burst release and an overall slightly faster long-term release of dasatinib.

TABLE 8

In vitro Release Properties of Dasatinib Nanoparticles Doped with Lithocholic Acid.

| Time (hours) | 145-54-3: 16/5, 3% lithocholic acid, 30% load, 2% solid, 149.9 nm, 3.5% | 145-54-3R: 16/5, 3% lithocholic acid, 30% load, 2% solid, 124.8 nm, 2.1% | 145-107-3: 16/5, 3% lithocholic acid, 130.5 nm, 2.2% |
|---|---|---|---|
| 0 | 4.77 | 6.66 | 6.62 |
| 1 | 9.31 | 12.65 | 13.91 |
| 2 | 13.59 | 17.08 | 20.03 |
| 4 | 22.63 | 31.74 | 33.32 |
| 6 | 31.52 | 43.71 | 46.00 |

The above formulations demonstrate the ability of 3% lithocholic acid in BA both to improve drug loading and slow the rate of drug release as compared to nanoparticles prepared without acid.

Example 8: Preparation of Dasatinib-Containing Nanoparticles—Emulsion Process 3

Preparation of buffer. To make 1000 mL of 0.5 M Phosphate (pKa$_2$=7.2) Buffer: pH=6.5, dissolve 68.995 g of NaH$_2$PO$_4$ H$_2$O (M$_r$=137.99) in approximately 900 mL of pure water. Titrate to pH 6.49 at the lab temperature of 25° C. with NaOH strong base as needed. Make up volume to 1000 mL with pure water. To make 1000 mL of 0.37 M Phosphate (pKa$_2$=7.2) Buffer: pH=6.5, dissolve 46.92 g of NaH$_2$PO$_4$ H$_2$O (M$_r$=137.99) in approximately 900 mL of pure water. Titrate to pH 6.49 at the lab temperature of 25° C. with NaOH strong base as needed. Make up volume to 1000 mL with pure water. To make 1000 mL of 0.17 M Phosphate (pKa$_2$=7.2) Buffer: pH=6.5, dissolve 23.46 g of NaH$_2$PO$_4$ H$_2$O (M$_r$=137.99) in approximately 900 mL of pure water. Titrate to pH 6.49 at the lab temperature of 25° C. with NaOH strong base as needed. Make up volume to 1000 mL with pure water.

Preparation of pamoic acid solution. A 29% (w/w) solution of pamoic acid in DMSO was prepared by mixing 2.9 g of pamoic acid with 7.1 g of DMSO in a container. The container was heated in a heating oven at 70-80° C. until all of the pamoic acid was dissolved.

Preparation of 8% TFA/7.5% water/84.5% benzyl alcohol (wt %) solution. Trifluoroacetic acid (TFA) (3.2 g), deionized (DI) water (3.0 g), and benzyl alcohol (BA) (33.8 g) were combined to prepare the 8% TFA/7.5% water/84.5% benzyl alcohol (wt %) solution.

Preparation of organic phase. To a first 20 mL glass vial are added poly(lactic acid)-poly(ethylene glycol) diblock copolymer (PLA-PEG) (700 mg) and ethyl acetate alcohol (7.583 g). The mixture is vortexed overnight to give a polymer-EA solution. To a second 20 mL glass vial are added 300 mg of drug (dasatinib), 1.736 g of the above 8% TFA/7.5% water/BA solution, and 792 mg of the above 29% pamoic acid/DMSO solution and the mixture vortexed until a clear drug solution is obtained to give a drug-acid-BA solution. Prior to formulation of the nanoparticles, polymer-EA solution is added to the drug-acid-BA solution and the mixture vortexed to form the organic phase.

Preparation of aqueous phase (0.09% Brij100, 4% Benzyl Alcohol in Water). To a 1 L bottle are added Brij 100 (0.9 g) and DI water (959.1 g). The mixture is stirred on a stir plate until dissolved. To the Brij/water is added benzyl alcohol (40 g) and the mixture stirred on a stir plate until dissolved.

Formation of emulsion. The ratio of aqueous phase to oil phase is 5:1. The organic phase is poured into the aqueous phase and the mixture homogenized using a hand homogenizer for 10 seconds at room temperature to form a course emulsion. The course emulsion is fed through a high pressure homogenizer (110S) with pressure set at ~11,000 psi on gauge for 1 discreet pass to form a nanoemulsion (fine emulsion).

Formation of nanoparticles. The nanoemulsion is poured into a quench (pH 6.5 phosphate buffer with appropriate mole) at less than 5° C. while stirring on a stir plate to form a quenched phase. The ratio of quench to emulsion is 10:1. To the quenched phase is added Tween 80 in water (35% (w/w)) at a ratio of 100:1 Tween 80 to drug.

Concentration of nanoparticles through tangential flow filtration (TFF). The quenched phase is concentrated using TFF with 300 kDa Pall cassette (2×0.1 m$^2$ membranes) to form a nanoparticle concentrate of ~200 mL. The nanoparticle concentrate is diafiltered with ~20 diavolumes (4 L) of cold DI water. The volume of the diafiltered nanoparticle concentrate is reduced to a minimal volume. Cold water (100 mL) is added to the vessel and pumped through the membrane to rinse and form a slurry. The final slurry (~100 mL) is collected in a glass vial.

Determination of solids concentration of unfiltered final slurry. To a tared 20 mL scintillation vial is added a volume of final slurry, which is dried under vacuum on a lyophilizer/oven. The weight of nanoparticles in the volume of dried slurry is determined. To the final slurry is added concentrated sucrose (0.666 g/g) to attain 10% sucrose.

Determination of solids concentration of 0.45 µm filtered final slurry. A portion of the final slurry sample is filtered through a 0.45 µm syringe filter before addition of sucrose. To a tared 20 mL scintillation vial is added a volume of filtered sample, which is dried under vacuum using a lyophilizer/oven. The remaining sample of unfiltered final slurry with sucrose is frozen.

Example 9: Effect of Quench pH on Drug Loading

Eight dasatinib formulations doped with pamoic acid were made using the protocol in Example 8. The formulation conditions and characterization are provided in Tables 9 and 10. Formulation conditions included either citric/phosphate buffer (pH 4.5) as the quench or DI water as the quench. Solutions were clear and stable during the formulation period, and emulsions were sufficiently stable during formulation.

As shown in Tables 9 and 10, drug loading more than doubled for formulations that included the citric/phosphate buffer quench as compared to formulations that included a DI water quench. Further, SQ holding resulted in a loss of 2~3% drug loading (e.g., a reduction from greater than 14% to approximately 11%).

Pamoic acid formulations that included a DI water quench also had a higher drug loading as compared to analogous formulations doped with oleic acid or cholic acids instead of pamoic acid (see Tables 6 and 7 above).

EQUIVALENTS

Those skilled in the art will recognize, or be able to ascertain using no more than routine experimentation, many equivalents to the specific embodiments of the invention described herein. Such equivalents are intended to be encompassed by the following claims.

INCORPORATION BY REFERENCE

The entire contents of all patents, published patent applications, websites, and other references cited herein are hereby expressly incorporated herein in their entireties by reference.

What is being claimed is:

1. A therapeutic nanoparticle comprising:
   about 0.2 to about 20 weight percent of a basic therapeutic agent having a protonatable nitrogen, wherein the basic therapeutic agent is a tyrosine kinase inhibitor selected from the group consisting of sunitinib, imatinib, nilotinib, dasatinib, bosutinib, ponatinib, bafetinib, and pharmaceutically acceptable salts thereof;
   pamoic acid, wherein the molar ratio of the pamoic acid to the basic therapeutic agent is about 0.25:1 to about 2:1; and
   about 50 to about 99.75 weight percent of a diblock poly(lactic) acid-poly(ethylene)glycol copolymer or a diblock poly(lactic acid-co-glycolic acid)-poly(ethylene)glycol copolymer, wherein the therapeutic nanoparticle comprises about 10 to about 30 weight percent poly(ethylene)glycol.

2. The therapeutic nanoparticle of claim 1, wherein the molar ratio of the pamoic acid to the basic therapeutic agent is about 0.5:1 to about 1.5:1.

3. The therapeutic nanoparticle of claim 1, wherein the molar ratio of the pamoic acid to the basic therapeutic agent is about 0.75:1 to about 1.25:1.

TABLE 9

Formulation Conditions and Characterization.

| Lot # | Quench | Drug Theo. Loading (%) | Solid Conc. | pH before Quench | pH after Quench | Loading % | size (nm) | % Brij, pass# @ psi# | NP Solids (mg/mL) | Acid/drug molar ratio |
|---|---|---|---|---|---|---|---|---|---|---|
| 212-38-1 | Buffer, no SQ hold | 22 | 10% | | | 14.50% | 100.2 | 0.06% Brij, 1@40 psi | 2.51 | 1.000 |
| 212-38-1R | Buffer, no SQ hold | 24 | 10% | 4.57 | 4.59 | 14.66% | 98.8 | 0.06% Brij, 1@46 psi | 2.48 | 1.000 |
| 212-38-2 | Buffer | 22 | 10% | 4.57 | 4.57 | 10.82% | 95 | 0.06% Brij, 1@46 psi | 2.30 | 1.000 |
| 212-38-2R | Buffer | 22 | 10% | | | 12.16% | 99.2 | 0.06% Brij, 1@46 psi | 2.27 | 1.000 |
| 212-38-3 | Water, no SQ hold | 22 | 10% | 5.9 | 3.28 | 6.15% | 101.8 | 0.06% Brij, 1@46 psi | 2.36 | 1.000 |
| 212-38-3R | Water | 22 | 10% | | | 3.98% | 97.7 | 0.06% Brij, 1@46 psi | 2.30 | 1.000 |
| 212-38-4 | Water | 22 | 10% | 5.9 | 3.19 | 4.23% | 111.2 | 0.06% Brij, 1@46 psi | 3.52 | 1.000 |
| 212-38-4R | Water, 10 min hold | 22 | 10% | | | 5.84% | 383.1 | 0.06% Brij, 1@46 psi | 2.28 | 1.000 |

TABLE 10

Formulation Conditions and Characterization.

| Lot # | Quench medium | pH of quench medium | | Drug theoretical loading (%) | Solid conc | Acid/drug feed ratio | Drug loading | size (nm) | Encapsulation efficiency |
|---|---|---|---|---|---|---|---|---|---|
| | | Before adding emulsion | After adding emulsion | | | | | | |
| 212-38-3 | Water | 5.9 | 3.28 | 22 | 10% | 1.000 | 6.15% | 101.8 | 27.93% |
| 212-38-1R | Buffer | 4.57 | 4.59 | 22 | 10% | 1.000 | 14.66% | 98.8 | 66.65% |

4. A therapeutic nanoparticle comprising:
a hydrophobic ion-pair comprising pamoic acid and a therapeutic agent having at least one ionizable amine moiety, wherein the therapeutic agent is a tyrosine kinase inhibitor selected from the group consisting of sunitinib, imatinib, nilotinib, dasatinib, bosutinib, ponatinib, bafetinib, and pharmaceutically acceptable salts thereof; and
about 50 to about 99.75 weight percent of a diblock poly(lactic) acid-poly(ethylene)glycol copolymer, wherein the poly(lactic) acid-poly(ethylene)glycol copolymer has a number average molecular weight of about 15 kDa to about 20 kDa poly(lactic acid) and a number average molecular weight of about 4 kDa to about 6 kDa poly(ethylene)glycol.

5. The therapeutic nanoparticle of claim 4, comprising about 0.05 to about 30 weight percent of the pamoic acid.

6. The therapeutic nanoparticle of claim 4, wherein the pamoic acid and the therapeutic agent form a hydrophobic ion pair in the therapeutic nanoparticle.

7. The therapeutic nanoparticle of claim 4, comprising about 2 to about 20 weight percent of the therapeutic agent.

8. The therapeutic nanoparticle of claim 4, comprising about 10 to about 20 weight percent of the therapeutic agent.

9. The therapeutic nanoparticle of claim 4, wherein the hydrodynamic diameter of the therapeutic nanoparticle is about 60 to about 150 nm.

10. The therapeutic nanoparticle of claim 4, wherein the therapeutic agent is selected from the group consisting of dasatinib and pharmaceutically acceptable salts thereof.

11. The therapeutic nanoparticle of claim 9, wherein the hydrodynamic diameter is about 90 to about 120 nm.

12. The therapeutic nanoparticle of claim 5, wherein the therapeutic nanoparticle substantially immediately releases less than about 30% of the therapeutic agent when placed in a phosphate buffer solution at 37° C.

13. The therapeutic nanoparticle of claim 5, wherein the poly(lactic) acid-poly(ethylene)glycol copolymer has a poly(lactic) acid number average molecular weight fraction of about 0.6 to about 0.8.

14. The therapeutic nanoparticle of claim 5, wherein the therapeutic nanoparticle comprises about 10 to about 25 weight percent poly(ethylene)glycol.

\* \* \* \* \*